US010624949B1

(12) United States Patent
Negrete et al.

(10) Patent No.: US 10,624,949 B1
(45) Date of Patent: Apr. 21, 2020

(54) METHODS FOR TREATING DISEASES RELATED TO THE WNT PATHWAY

(71) Applicant: Sandia Corporation, Albuquerque, NM (US)

(72) Inventors: Oscar A. Negrete, Livermore, CA (US); Brooke Nicole Harmon, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/204,804

(22) Filed: Jul. 7, 2016

Related U.S. Application Data

(60) Provisional application No. 62/197,341, filed on Jul. 27, 2015.

(51) Int. Cl.
| | | |
|---|---|---|
| *A61K 31/40* | (2006.01) | |
| *A61K 31/235* | (2006.01) | |
| *A61K 31/35* | (2006.01) | |
| *A61K 31/44* | (2006.01) | |
| *A61K 31/47* | (2006.01) | |
| *A61K 31/519* | (2006.01) | |
| *A61K 31/135* | (2006.01) | |
| *A61K 31/18* | (2006.01) | |
| *A61K 31/42* | (2006.01) | |
| *A61K 31/425* | (2006.01) | |
| *A61K 38/17* | (2006.01) | |
| *A61K 31/407* | (2006.01) | |
| *A61K 31/475* | (2006.01) | |

(Continued)

(52) U.S. Cl.
CPC ........ *A61K 38/1709* (2013.01); *A61K 31/136* (2013.01); *A61K 31/407* (2013.01); *A61K 31/4439* (2013.01); *A61K 31/475* (2013.01); *C12Q 1/6883* (2013.01); *C12Q 2600/178* (2013.01)

(58) Field of Classification Search
CPC .......................... A61K 31/404; A61K 31/216
USPC ................................................ 514/418, 532
See application file for complete search history.

(56) References Cited

U.S. PATENT DOCUMENTS 8,828,736 B2   9/2014  Perroud et al.
2004/0204477 A1  10/2004  Moll et al.
(Continued)

FOREIGN PATENT DOCUMENTS

WO    WO 2016/054225 A1    4/2016

OTHER PUBLICATIONS

Filone et al. "Rift Valley Fever virus infection of human cells and insect hosts is promoted by protein kinase C Epsilon," Plos One, 2010, vol. 5, issue 11, e 15483. (Year: 2010).*

(Continued)

*Primary Examiner* — Shengjun Wang
(74) *Attorney, Agent, or Firm* — Helen S. Baca; Samantha Updegraff

(57) ABSTRACT

The present invention relates to methods for treating a disease, in which the disease arises from dysregulation of the Wnt signaling pathway. In some instances, the disease can be treated by administering a Wnt pathway inhibitory compound. In other instances, the method optionally includes conducting a genome-wide screening to determine one or more genes resulting in a reduced disease state and then identifying the gene(s) as being involved in the Wnt signaling pathway.

14 Claims, 19 Drawing Sheets

(51) Int. Cl.
*A61K 31/4439* (2006.01)
*A61K 31/136* (2006.01)
*C12Q 1/6883* (2018.01)

(56) References Cited

U.S. PATENT DOCUMENTS

| | | | |
|---|---|---|---|
| 2011/0105423 A1* | 5/2011 | Shaw | A61K 31/00 514/34 |
| 2012/0207857 A1 | 8/2012 | Siede et al. | |
| 2012/0302733 A1* | 11/2012 | Padgett | C07K 14/555 530/351 |
| 2014/0031374 A1 | 1/2014 | Holsworth et al. | |
| 2014/0038922 A1 | 2/2014 | Lum et al. | |
| 2014/0255426 A1 | 9/2014 | Silvestri et al. | |
| 2015/0025114 A1 | 1/2015 | Ji et al. | |
| 2015/0157633 A1 | 6/2015 | Lum et al. | |
| 2015/0272885 A1 | 10/2015 | Ashley et al. | |
| 2015/0322057 A1 | 11/2015 | Holsworth et al. | |
| 2015/0374696 A1 | 12/2015 | Lum et al. | |
| 2016/0082014 A1 | 3/2016 | Cheng et al. | |
| 2017/0065587 A1* | 3/2017 | Liu | A61K 31/4709 |

OTHER PUBLICATIONS

U.S. Appl. No. 14/081,629, filed Nov. 15, 2013, Peabody et al.
Al-Harthi L, "Interplay between Wnt/β-catenin signaling and HIV: virologic and biologic consequences in the CNS," *J. Neuroimmune Pharmacol.* 2012;7(4):731-9.
Anastas JN et al., "WNT signalling pathways as therapeutic targets in cancer," *Nat. Rev. Cancer* 2013;13(1):11-26.
Angelova M et al., "Human cytomegalovirus infection dysregulates the canonical Wnt/β-catenin signaling pathway," *PLoS Pathog.* 2012;8(10):e1002959 (13 pp.).
Baer A et al., "Induction of DNA damage signaling upon Rift Valley fever virus infection results in cell cycle arrest and increased viral replication," *J. Biol. Chem.* 2012;287(10):7399-410.
Billecocq A et al., "NSs protein of Rift Valley fever virus blocks interferon production by inhibiting host gene transcription," *J. Virol.* 2004;78(18):9798-806.
Brass AL et al., "Identification of host proteins required for HIV infection through a functional genomic screen," *Science* 2008;319(5865):921-6.
Bushman FD et al., "Host cell factors in HIV replication: meta-analysis of genome-wide studies," *PLoS Pathog.* 2009;5(5):e1000437 (12 pp.).
Cha MY et al., "Hepatitis B virus X protein is essential for the activation of Wnt/β-catenin signaling in hepatoma cells," *Hepatology* 2004;39(6):1683-93.
Chen Z et al., "2,4-Diamino-quinazolines as inhibitors of beta-catenin/Tcf-4 pathway: potential treatment for colorectal cancer," *Bioorg. Med. Chem. Lett.* 2009;19(17):4980-3.
Cheng E et al., "Signatures of host mRNA 5' terminus for efficient hantavirus cap snatching," *J. Virol.* 2012;86(18):10173-85.
Cherry S, "What have RNAi screens taught us about viral-host interactions?," *Curr. Opin. Microbiol.* 2009;12(4):446-52.
Clevers H et al., "Wnt/β-catenin signaling and disease," *Cell* 2012;149(6):1192-205.
Davidson G et al., "Emerging links between CDK cell cycle regulators and Wnt signaling," *Trends Cell. Biol.* 2010;20(8):453-60.
Earl PL et al., "Development and use of a vaccinia virus neutralization assay based on flow cytometric detection of green fluorescent protein," *J. Virol.* 2003;77(19):10684-8.
Ebert O et al., "Oncolytic vesicular stomatitis virus for treatment of orthotopic hepatocellular carcinoma in immune-competent rats," *Cancer Res.* 2003;63(13):3605-11.
Elliott R, Schmaljohn CS. 2013. Bunyaviridae, p. 1244-1282. In Knipe DM, Howley PM (ed.), Fields Virology, 6 ed, vol. 1. Wolters Kluwer/Lippincott Williams and Wilkins, Philadelphia, PA.

Ewan K et al., "A useful approach to identify novel small molecule inhibitors of Wnt-dependent transcription," *Cancer Res.* 2010;70(14):5963-73.
Filone CM et al., "Development and characterization of a Rift Valley fever virus cell-cell fusion assay using alphavirus replicon vectors," *Virology* 2006;356(1-2):155-64.
Filone CM et al., "Rift Valley fever virus infection of human cells and insect hosts is promoted by protein kinase C epsilon," *PLoS One* 2010;5(11):e15483 (12 pp.).
Franceschini A et al., "String v9.1: protein-protein interaction networks, with increased coverage and integration," *Nucleic Acids Res.* 2013;41(Database issue):D808-15.
Fujii N et al., "An antagonist of Dishevelled protein-protein interaction suppresses β-catenin-dependent tumor cell growth," *Cancer Res.* 2007;67(2):573-9.
Fujimuro M et al., "Regulation of the interaction between glycogen synthase kinase 3 and the Kaposi's sarcoma-associated herpesvirus latency-associated nuclear antigen," *J. Virol.* 2005;79(16):10429-41.
Gaj T et al., "ZFN, TALEN, and CRISPR/Cas-based methods for genome engineering," *Trends Biotechnol.* 2013;31(7):397-405.
Grandy D et al., "Discovery and characterization of a small molecule inhibitor of the PDZ domain of dishevelled," *J. Biol. Chem.* 2009;284(24):16256-63.
Guu TS et al., "Bunyavirus: structure and replication," *Adv. Exp. Med. Biol.* 2012;726:245-66.
Hadjihannas MV et al., "Conductin/axin2 and Wnt signaling regulates centrosome cohesion," *EMBO Rep.* 2010;11(4):317-24.
Halbedl S et al., "Synthesis of novel inhibitors blocking Wnt signaling downstream of β-catenin," *FEBS Lett.* 2013;587(5):522-7.
Handeli S et al., "A small-molecule inhibitor of Tcf/β-catenin signaling down-regulates PPARγ and PPARσ activities," *Mol. Cancer Ther.* 2008;7(3):521-9.
Harmon B et al., "A genome-wide RNAi screen identifies a role for Wnt/beta-catenin signaling during Rift Valley fever virus infection," *J. Virol.* doi:10.1128/JVI.00543-16 (posted online May 25, 2016, 49 pp.).
Harmon B et al., "Genome-wide RNA interference screening for host factors required in Rift Valley Fever virus infection," *International Union of Microbiological Societies Congresses*, held on Jul. 27-Aug. 1, 2014 in Montréal, Canada (Abstract VIR-WK225.04, p. 1158).
Harmon B et al., "Identification of critical amino acids within the nucleoprotein of Tacaribe virus important for anti-interferon activity," *J. Biol. Chem.* 2013;288(12):8702-11.
Harmon B et al., "Rift Valley fever virus strain MP-12 enters mammalian host cells via caveola-mediated endocytosis," *J. Virol.* 2012;86(23):12954-70.
Hayward SD et al., "Notch and Wnt signaling: mimicry and manipulation by gamma herpesviruses," *Science STKE* 2006;2006(335):re4.
Hopkins K et al., "Bunyaviral cap-snatching vs. decapping: recycling cell cycle mRNAs," *Cell Cycle* 2013;12(24):3711-2.
Hopkins KC et al., "A genome-wide RNAi screen reveals that mRNA decapping restricts bunyaviral replication by limiting the pools of Dcp2-accessible targets for cap-snatching," *Genes Dev.* 2013;27(13):1511-25.
Hsieh A et al., "Hepatitis B viral X protein interacts with tumor suppressor adenomatous polyposis coli to activate Wnt/β-catenin signaling," *Cancer Lett.* 2011;300(2):162-72.
Hua Z et al., "Development of novel dual binders as potent, selective, and orally bioavailable tankyrase inhibitors," *J. Med. Chem.* 2013;56(24):10003-15.
Huang Z et al., "Targeting the Tcf4 $G^{13}ANDE^{17}$ binding site to selectively disrupt β-catenin/T-cell factor protein-protein interactions," *ACS Chem. Biol.* 2014;9(1):193-201.
Huang da W et al., "Systematic and integrative analysis of large gene lists using DAVID bioinformatics resources," *Nat. Protoc.* 2009;4(1):44-57.
Ikegami T et al., "Dual functions of Rift Valley fever virus NSs protein: inhibition of host mRNA transcription and post-transcriptional downregulation of protein kinase PKR," *Ann. NY Acad. Sci.* 2009;1171 Suppl 1:E75-85.

(56) References Cited

OTHER PUBLICATIONS

Ikegami T et al., "Rescue of infectious rift valley fever virus entirely from cDNA, analysis of virus lacking the NSs gene, and expression of a foreign gene," *J. Virol.* 2006;80(6):2933-40.
Ikegami T et al., "Rift Valley fever virus NSs mRNA is transcribed from an incoming anti-viral-sense S RNA segment," *J. Virol.* 2005;79(18):12106-11.
Ikegami T et al., "Rift Valley fever virus NSs protein promotes post-transcriptional downregulation of protein kinase PKR and inhibits eIF2α phosphorylation," *PLoS Pathog.* 2009;5(2):e1000287 (17 pp.).
Ikegami T et al., "The pathogenesis of Rift Valley fever," *Viruses* 2011;3(5):493-519.
Islam MK et al., "High-throughput screening using a whole-cell virus replication reporter gene assay to identify inhibitory compounds against Rift Valley fever virus infection," *J. Biomol. Screen.* 2016;21(4):354-62.
Kahn M, "Can we safely target the WNT pathway?," *Nat. Rev. Drug Disc.* 2014;13(7):513-32.
Kalveram B et al., "NSs protein of rift valley fever virus promotes posttranslational downregulation of the TFIIH subunit p62," *J. Virol.* 2011;85(13):6234-43.
Kapoor A et al., "Wnt modulating agents inhibit human cytomegalovirus replication," *Antimicrob. Agents Chemother.* 2013;57(6):2761-7.
Karlas A et al., "Genome-wide RNAi screen identifies human host factors crucial for influenza virus replication," *Nature* 2010;463(7282):818-22.
Klaus A et al., "Wnt signalling and its impact on development and cancer," *Nat. Rev. Cancer* 2008;8(5):387-98.
Krishnan MN et al., "RNA interference screen for human genes associated with West Nile virus infection," *Nature* 2008;455(7210):242-5.
Kuri T et al., "Species-independent bioassay for sensitive quantification of antiviral type I interferons," *Virol. J.* 2010;7:50 (6 pp.).
Le May N et al., "The N terminus of Rift Valley fever virus nucleoprotein is essential for dimerization," *J. Virol.* 2005;79(18)11974-80.
Le PN et al., "Targeting the Wnt pathway in human cancers: therapeutic targeting with a focus on OMP-54F28," *Pharmacol. Ther.* 2015;146:1-11.
Lenz HJ et al., "Safely targeting cancer stem cells via selective catenin coactivator antagonism," *Cancer Sci.* 2014;105(9):1087-92.
Li VS et al., "Wnt signaling through inhibition of β-catenin degradation in an intact Axin1 complex," *Cell* 2012;1 49(6)1 245-56.
Liu J et al., "Enhancement of canonical Wnt/β-catenin signaling activity by HCV core protein promotes cell growth of hepatocellular carcinoma cells," *PLoS One* 2011;6(11):e27496 (10 pp.).
Liu J et al., "Hepatitis C virus core protein activates Wnt/β-catenin signaling through multiple regulation of upstream molecules in the SMMC-7721 cell line," *Arch. Virol.* 2011;156(6):1013-23.
MacDonald BT et al., "Wnt/beta-catenin signaling: components, mechanisms, and diseases," *Dev. Cell.* 2009;17(1):9-26.

Mansuroglu Z et al., "Nonstructural NSs protein of rift valley fever virus interacts with pericentromeric DNA sequences of the host cell, inducing chromosome cohesion and segregation defects," *J. Virol.* 2010;84(2):928-39.
Marcato V et al., "β-catenin upregulates the constitutive and virus-induced transcriptional capacity of the interferon beta promoter through T-cell factor binding sites," *Mol. Cell. Biol.* 2015;36(1)13-29.
Meier R et al., "Genome-wide small interfering RNA screens reveal VAMP3 as a novel host factor required for Uukuniemi virus late penetration," *J. Virol.* 2014;88(15):8565-78.
Mercer J et al., "RNAi screening reveals proteasome- and Cullin3-dependent stages in vaccinia virus infection," *Cell Rep.* 2012;2(4):1036-47.
Mohr SE et al., "RNAi screening comes of age: improved techniques and complementary approaches," *Nat. Rev. Molec. Cell. Biol.* 2014;15:591-600.
Nikolsky Y et al., "Protein networks and pathway analysis: preface," *Methods Mol. Biol.* 2009;563:v-vii.
Pepin M et al., "Rift Valley fever virus (*Bunyaviridae*: Phlebovirus): an update on pathogenesis, molecular epidemiology, vectors, diagnostics and prevention," *Vet. Res.* 2010;41(6):61 (40 pp.).
Rolin AI et al., "The risk of Rift Valley fever virus introduction and establishment in the United States and European Union," *Emerg. Microbes Infect.* 2013;2(12):e81 (8 pp.).
Ross TM et al., "Animal models of Rift Valley fever virus infection," *Virus Res.* 2012;163(2):417-23.
Schudel BR et al., "Microfluidic platforms for RNA interference screening of virus-host interactions," *Lab Chip* 2013;13(5):811-7.
Shalem O et al., "High-throughput functional genomics using CRISPR-Cas9," *Nat. Rev. Genet.* 2015;16(5):299-311.
Teferi WM et al., "A whole-genome RNA interference screen for human cell factors affecting myxoma virus replication," *J. Virol.* 2013;87(8):4623-41.
Voronkov A et al., "Wnt/beta-catenin signaling and small molecule inhibitors," *Curr. Pharm. Des.* 2013;19(4):634-64.
Waaler J et al., "A novel tankyrase inhibitor decreases canonical Wnt signaling in colon carcinoma cells and reduces tumor growth in conditional APC mutant mice," *Cancer Res.* 2012;72(11):2822-32.
Walpita P et al., "Reverse genetics of negative-stranded RNA viruses: a global perspective," *FEMS Microbiol. Lett.* 2005;244:9-18.
Zhang W et al., "Fluorinated N,N-dialkylaminostilbenes for Wnt pathway inhibition and colon cancer repression," *J. Med. Chem.* 2011;54(5):1288-97.
Zhang XD et al., "Hepatitis B virus X protein accelerates the development of hepatoma," *Cancer Biol. Med.* 2014;11(3):182-90.
Zhang XD, "Illustration of SSMD, z score, SSMD*, z* score, and t statistic for hit selection in RNAi high-throughput screens," *J. Biomol. Screen.* 2011;16(7):775-85.
Zhou Y et al., "High-throughput screening of a CRISPR/Cas9 library for functional genomics in human cells," *Nature* 2014;509:487-91.

* cited by examiner

Primary Hepatocytes

FIG. 4G

Wild-type RVFV

California encephalitis virus

FIG. 10B

LaCrosse virus

METHODS FOR TREATING DISEASES RELATED TO THE WNT PATHWAY

CROSS-REFERENCE TO RELATED APPLICATION

This application claims the benefit of U.S. Provisional Application No. 62/197,341, filed Jul. 27, 2015, which is hereby incorporated by reference in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to methods for treating a disease, in which the disease arises from dysregulation of the Wnt signaling pathway. In some instances, the disease can be treated by administering a Wnt pathway inhibitory compound. In other instances, the method optionally further includes conducting a genome-wide screening to determine one or more genes resulting in a reduced disease state and then identifying the gene(s) as being involved in the Wnt signaling pathway.

BACKGROUND OF THE INVENTION

Emerging diseases, such as those arising from infectious pathogens, represent a critical threat. Yet, tools to understand such pathogens and countermeasures to combat such diseases remain lacking. For instance, the Rift Valley fever virus (RVFV) is a mosquito-borne virus that is endemic to Africa. Nonetheless, the U.S. National Institute of Allergy and Infectious Diseases (NIAID) deems RVFV to be a Category A pathogen that poses some of the highest risk to U.S. national security and public health due to ease of transmission and high risk of human death. Furthermore, no treatments exist for RVFV disease. Accordingly, there is a need for additional modalities to further genomic and functional understanding of emerging pathogens, thereby facilitating the discovery of countermeasures and clinically relevant treatments for such pathogens.

SUMMARY OF THE INVENTION

The present invention relates to methods for understanding and identifying dysregulation of a host's cellular regulatory pathway upon being exposed to a causative agent for a disease (e.g., upon being exposed to a pathogen). In particular embodiments, the method herein includes conducting a genome-wide screening on a cell obtained from a subject, thereby determining one or more genes resulting in a reduced disease state of the cell; identifying the one or more genes as being involved in a Wnt signaling pathway; and exposing the cell to one of a plurality of Wnt pathway inhibitory compounds, or a salt thereof, thereby determining a class of Wnt pathway inhibitory compounds that results in a reduced disease state. In other embodiments, the method includes administering a medication to the subject, where the medication is administered in an effective amount to treat the disease. In further embodiments, the medication includes a Wnt pathway inhibitory compound, or the medication is within the class of Wnt pathway inhibitory compounds that results in a reduced disease state. In certain embodiments, the cell is in a patient. Additional details follow.

DEFINITIONS

As used herein, the term "about" means +/−10% of any recited value. As used herein, this term modifies any recited value, range of values, or endpoints of one or more ranges.

By "salt" is meant an ionic form of a compound or structure (e.g., any formulas, compounds, or compositions described herein), which includes a cation or anion compound to form an electrically neutral compound or structure. Salts are well known in the art. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth. The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, gluconate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

By "pharmaceutically acceptable salt" is meant a salt that is, within the scope of sound medical judgment, suitable for use in contact with the tissues of humans and animals without undue toxicity, irritation, allergic response and the like and are commensurate with a reasonable benefit/risk ratio.

By "isomer" is meant a molecule having the same molecular formula as the reference molecule. Exemplary isomers include stereoisomers, diastereomers, enantiomers, geometric isomers, tautomers, as well as mixtures thereof.

By an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an inhibitor of β-catenin, an effective amount of an agent is, for example, an amount sufficient to achieve a reduction in β-catenin or its activity, as compared to the response obtained without administration of the agent.

By "subject" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and/or remission (whether partial or total), whether detectable or undetectable.

Other features and advantages of the invention will be apparent from the following description and the claims.

BRIEF DESCRIPTION OF THE DRAWINGS

FIG. 4A-4H shows that RVFV infection induces Wnt/β-catenin signaling and that pre-activation of the canonical Wnt pathway enhances RVFV replication. Provided are data for 293T cells that were transfected with the TCF-LEF-1 luc reporter construct TF and pcDNA3.1-GFP or pcDNA3.1-mKate reporter plasmids (FIGS. 4A-4B). At 18 hpt, cells were treated with positive control Wnt3A (100 ng/ml) or virus (MP12 or MP12-GFP at MOI=3) for the indicated time periods (FIG. 4A). At 18 hpt, cells were infected with virus at the indicated MOIs; and all viruses (MP12, MP12-GFP, VacV, or VSV) were used at the same MOIs as determined by plaque assay (FIG. 4B). At 5 hpi, luciferase activity was measured, normalized to expression of GFP (RVFV MP12) or mKate (RVFV MP12-GFP, VacV, or VSV); and fold activation was calculated by dividing the relative luciferase activity of treated/infected cells with that of untreated cells. Data are presented as mean±S.D. Also provided are Western blots for whole cell lysates of 293T cells (FIG. 4C), which were infected with RVFV at indicated MOIs and analyzed by Western blotting at 4.5 hpi. The top membrane was probed with activated β-catenin antibody, and the bottom membrane was probed with anti-actin antibodies. Representative results are shown (n=3). Gene expression analysis was performed using quantitative RT-PCR for the β-catenin (CTNNB1), cyclin D1 (CCND1), DVL1, LRP5, or matrix metalloproteinase-7 (MMP7) genes after 20 h of treatment with 50 ng/ml of Wnt3A or 4.5 h of infection with virus (MOI=1) in A549 cells (FIG. 4D). Each experimental condition was run in triplicate, and the fold change was determined by dividing the average of the infected samples by the average of uninfected samples. Further data are provided for HeLa cells (FIG. 4E), A549 cells (FIG. 4F), and primary hepatocytes cells (FIG. 4G), which were pre-treated with indicated concentrations of Wnt3A for 20 h and then infected with MOI=0.1, 0.3, or 1 of RVFV MP12-GFP (dashed lines) or VSV (solid lines). Levels of virus infection enhancement are indicated by fold changes compared to untreated/infected controls. Data are also provided for HeLa cells (FIG. 4H), which were pre-incubated with no inhibitor (NI) or 50 ng/ml of Wnt3A for 20 h followed by infection with wild-type (WT) RVFV at an MOI of 0.1. Wnt3A was also present during the infection. Supernatants were collected at 36 hpi, and viral titers were measured by plaque assay on Vero cells. Three independent experiments were performed in triplicate. Data are presented as mean±S.D. (**, P<0.01; *, P<0.05).

FIG. 5A-5E shows that inhibitors that block Wnt signaling downstream of the membrane receptor complex inhibit RVFV infection. Provided are data for relative percent infection of HeLa cells that were pretreated with the indicated inhibitors for 1 h (FIG. 5A-5C). BAF (100 nM) was used as control for inhibition of RVFV infection. The inhibitors were also present during 3 h incubation with GFP reporter viruses (MOI=1) and during overnight incubation. Also provided are data for primary human hepatocytes (FIG. 5D), which were pretreated with no inhibitor (NI)/50 µM DMSO, 100 nM BAF, 5 µM FH535, 10 µM Wnt XII, 10 µM iCRT-14, 10 µM JW67, 10 µM Endo-IWR-1, 10 µM Exo-IWR-1, 50 µM Dvl-PDZ II, 300 ng/ml of DKK-1, or 500 ng/ml of WIF for 1 h prior to and during 3 h infection with RVFV-GFP (MOI 1), and during overnight incubation. The percentage of infection was determined by taking untreated (NI) or DMSO-treated and infected samples as 100% infected (0 µM). Thee independent experiments were performed in triplicate. Data are presented as mean±S.D. (**, P<0.01; *, P<0.05). Also, HeLa cells were pre-incubated for 1 h (FIG. 5E) with 50 µM DMSO (black), Dvl-PDZ II (dark gray), JW67 (medium gray), or iCRT-14 (light gray) followed by infection with RVFV MP12 or WT RVFV (MOI=0.1). The inhibitors were also present during the infection. Supernatants were collected at 36 hpi, and viral titers were measured by plaque assay on Vero cells. Data are presented as mean±S.D. (n=3) (**, P<0.0001; *, P<0.001; **, P<0.01).

FIG. 6A-6C shows that inhibitors that block Wnt signaling downstream of the membrane receptor complex inhibit RVFV infection in A549 cells, as well as reduce the percentage of RVFV infected cells measured by flow cytometry. Provided are average levels of infection detected by GFP fluorescence (±S.D.), compared to those for untreated (no inhibitor, i.e., 50 µM DMSO) controls. As seen in FIG. 6A, A549 cells were pretreated for 1 h with inhibitors that block at the Wnt receptor complex using Dvl-PDZ Domain Inhibitor II ("DVL-PDZ II," at concentrations of 0, 12.5, 25, or 50 µM), recombinant DKK-1 ("DKK-1" at concentrations of 100, 200 or 300 mg/ml), or recombinant WIF-1 ("WIF-1" at concentrations of 100, 300 or 500 mg/ml). As also seen in FIG. 6B, A549 cells were treated with inhibitors of the β-catenin destruction complex (DC) using Endo-IWR-1 and JW67 small molecules. Exo-IWR-1 is an inactive stereoisomer of Endo IWR. Finally, as seen in FIG. 6C, A549 cells were treated with inhibitors of activated β-catenin and nuclear import using FH535, Wnt XII, or iCRT-14. Bafilomycin (BAF) is an inhibitor of pH-dependent endocytosis and was used as control. The inhibitors were also present during the 3 h of incubation with GFP reporter viruses RVFV-GFP, VacV, or VSV (MOI=1). GFP expression was normalized to cell titers measured by alamarBlue® fluorescence. The percentage of infection was determined by taking untreated or DMSO-treated and infected samples as 100% infected. Shown are the means for three independent experiments performed in triplicate (**, P<0.01; *, P<0.05).

FIG. 7A-7C shows the effect of inhibitors on RVFV-infected cells. Provided are data for HeLa cells (FIG. 7A) and 293T cells (FIG. 7B-7C), which were pre-incubated for 1 h with 100 nM BAF, 5 µM FH535, 10 µM Wnt XII, 10 µM iCRT-14, 10 µM JW67, 10 µM Endo-IWR-1, 10 µM Exo-IWR-1 (an inactive stereoisomer), 50 µM Dvl-PDZ II, 300 µg/ml of DKK-1, or 500 µg/ml of WIF-1. The cells were then infected with RVFV MP12 or RVFV MP12-GFP (MOI=3) for 16 h in the presence of inhibitors. Infection was measured by flow cytometry using anti-RVFV polyclonal antibodies or GFP expression for RVFV MP12-GFP. Provided are histograms (FIG. 7C) representing uninfected 293T cells (gray bars) that were left untreated or were treated with DMSO or RVFV-infected 293T cells (black bars) treated with the indicated inhibitors. The data shown are representative results from four similar experiments. In FIG. 7A-7B, data are presented as the mean±S.D. of four independent experiments for each cell type (**, P<0.01; *, P<0.05).

FIG. 10A-10C shows that distantly related bunyaviruses induce Wnt/β-catenin signaling upon infection and are impeded by Wnt signaling inhibitors. As seen in FIG. 10A, 293T cells were transfected with TF and pcDNA3.1-GFP or pcDNA3.1-mKate reporter plasmids and then infected with the following viruses at indicated MOIs, including LCV (dashed line), RVFV MP12 (dotted line), CEV (black solid line), VSV (light gray solid line), or VacV (dark gray solid line). After 5 h, luciferase activity was measured and normalized to expression of GFP (for RVFV MP12, LCV, or CEV) or mKate (for VacV or VSV). Fold activation was calculated by dividing the relative luciferase activity of treated/infected cells with that of untreated cells. Three independent experiments were performed in triplicate. Data are presented as mean±S.D. Representative results are shown. Also provided are data for HeLa cells that were pre-incubated for 1 h with 50 µM DMSO, Dvl-PDZ II (dark gray), JW67 (medium gray), or iCRT-14 (light gray) followed by infection with CEV (FIG. 10B) or LCV (FIG. 10C) (MOI=0.1). The inhibitors were also present during the infection. Supernatants were collected at the indicated time points, and viral titers were measured by plaque assay on Vero cells. Data are presented as mean±S.D. (n=3) (**, $P<0.0001$; *, $P<0.001$; **, $P<0.01$;*, $P<0.05$).

FIG. 11 shows a schematic model of bunyavirus-induced Wnt/β-catenin signaling. In the OFF state, β-catenin is sequentially phosphorylated by the destruction complex (DC) and targeted for degradation (right side of FIG. 11). When the DC is disrupted by regulation of the scaffolding protein axin (via recruitment to the plasma membrane by Dvl after Wnt ligand triggered signaling, or by tankyrase mediated ADP-ribosylation of axin resulting in its ubiquitination and degradation), the signaling pathway is in the ON state (left side of FIG. 11). In the ON state, β-catenin accumulates in the cytoplasm and translocates to the nucleus, where it causes activation of TCF/LEF transcription factor and subsequent transcription of β-catenin responsive genes: cyclin D1, c-Jun and c-Myc. Without wishing to be limited by mechanism, results from this study described herein suggest that RVFV and other bunyaviruses may induce Wnt signaling during replication by circumventing the Wnt membrane receptor complex after virus entry. In particular, this study employed selective inhibitors to probe and target different stages of the Wnt/β-catenin signaling pathway to understand the effect of each stage on viral infectiousness. The proposed mechanism of virus induction of the ON state is indicated by solid gray arrow-headed lines, dashed gray lines, and solid gray bar-headed lines. Inhibitors that decreased RVFV infection are indicated within boxes that lead to solid black bar-headed lines. The ON state then proceeds to activation of TCF/LEF dependent Wnt/β-catenin transcription. Bunyaviral replication is dependent on a cap snatching mechanism, in which host-derived 5'-ends of mRNAs are used to prime viral gene transcription. Previous studies indicate host-derived 5'-ends on bunyaviral mRNAs contain mostly sequences related to cell cycle genes. Wnt/β-catenin signaling may therefore be induced during viral replication in order to provide pools of mRNAs, particularly cell cycle genes including cyclin D1, necessary for viral gene transcription initiation by cap snatching (double arrow-headed black line to represent hypothesis). Solid black bar-headed lines represent conditions that result in the OFF state (no stimulation, stabilized DC and inhibitor treatment), and gray lines (solid gray arrow-headed, dashed gray, and solid gray bar-headed lines) represent conditions that result in the ON state of Wnt/β-catenin signaling (tankyrase activity and virus-mediated induction). For the purposes of clarity, Wnt ligand-mediated activation of canonical Wnt signaling is not depicted in this figure.

DETAILED DESCRIPTION OF THE INVENTION

The present invention relates to methods for identifying dysregulation of a host's cellular regulatory pathway and then determining whether an agent that modulates that pathway can treat that dysregulation. In particular embodiments, the methods herein pertain to the Wnt pathway (e.g., the canonical Wnt pathway), in which exposure to a causative agent (e.g., a pathogen) results in dysregulation of the Wnt pathway and treatment with a therapeutic agent (e.g., a Wnt pathway inhibitory agent, such as any described herein) results in treating a disease associated with that dysregulation.

Described herein is a therapeutic method for treating (e.g., prophylactically treating) a viral infection by administering an effective amount of a Wnt pathway inhibitory compound. In one non-limiting instance, we understand that a class of viruses targets and modulates the Wnt pathway to propagate the viral infection. In addition, modulating certain portions of the pathway provided maximal protection against infection. For instance, the RVFV activates Wnt signaling during infection, yet only certain Wnt pathway inhibitory compounds decreased the percentage of infected cells. In this way, we propose methods of treating viral infections by administering certain inhibitors that target certain components of the Wnt pathway.

Also described herein is a generalized method for treating a disease, which includes conducting a screening methodology to identify one or more genes resulting in a reduced disease state of a cell (e.g., in which inhibition of that gene results in the reduced disease state, as compared to the state of a diseased cell). Once the gene(s) are identified, one or more agents to modulate that gene (e.g., one or more inhibitors) are delivered to the cell, thereby determining a class of agents that produces a reduced disease state in the cell. Then, a medication within that class can be administered to a subject to treat the disease. Exemplary screening and identifying methodologies are described herein.

Screening and Identifying Methodologies

Any of the methods herein can include conducting a screening methodology on a cell, thereby determining one or more genes resulting in a reduced disease state. The screening methodology can include genomic, transcriptomic, proteomic, and/or metabolomic screens. In particular, high-throughput screens can be employed, which can further include use of mass-spectrometry, microarray, fluorescence, and/or matrix-assisted laser desorption ionization detection schemes.

The role of each gene can be deduced by employing a genomic editing scheme to selectively insert, delete, silence, activate, or replace a certain gene within the host cell, such as by using RNA interference (RNAi), zinc finger nucleases (ZFNs), transcription activator-like effector nucleases (TALENs), the clustered regularly interspaced short palindromic repeats/CRISPR-associated system (CRISPR/Cas system), site-directed endonucleases, adeno-associated virus-mediated genome engineering, or meganucleases, as well as combinations thereof; and then by measuring the effect of that genomic editing on the disease state of the cell. For instance, a host cell can be genomically edited to delete or silence gene A, treated with a causative agent (e.g., any herein) to impose a diseased state, and then the extent of the diseased state can be measured and compared to a control, non-diseased cell. If silencing of gene A results in a reduced disease state, then treatment of the disease can include administering a gene A inhibitor to the cell or to the subject.

Figure 1A:
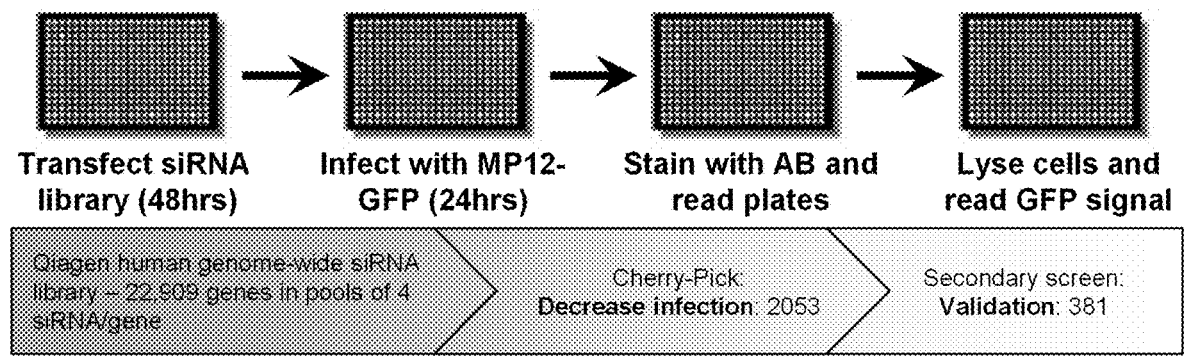
FIG. 1A-1C shows use of genome-wide RNAi screening to identify a role for Wnt/β-catenin signaling in RVFV infection. Provided is a schematic of the RNAi screen (FIG. 1A). Hit selection was based on strictly standardized mean difference (SSMD) statistics (FIG. 1B). The SSMD threshold was set to −1.30, which accounted for 381 gene hits that reduced infection upon their knockdown. The 381 gene hit list was analyzed through a bioinformatics online resource termed PANTHER (FIG. 1C), and 89 of those genes were clustered into one of 56 cellular pathways represented by pie sections in chart. Nine percent of the 89 genes clustered to the Wnt signaling pathway.

Prior to screening, the cell can be any useful cell type having any useful state. In one instance, the cell is obtained from a subject having the target disease to be treated. In another instance, the cell is obtained from a cell culture and then treated with a causative agent that causes or mimics the target disease. In yet another instance, the cell is obtained from a subject having a propensity or a higher risk for having or contracting the target disease. Exemplary causative agents include one or more pathogens (e.g., one or more viruses, such as a segmented RNA virus).

During screening, a gene of interest within the cell can be activated or inhibited, and then the effect of that activation or inhibition on the disease state can be measured in any useful manner. If a plurality of genes are identified, then these genes can be further analyzed by its functional clusters to determine commonalities (e.g., using any useful bioinformatics analytical tool, such as PANTHER, DAVID, and/or STRING databases). In one instance, the gene(s) relate to the Wnt pathway, and the gene(s) of interest affect entry into a host cell, cytoplasmic stability of a destruction complex in the Wnt signaling pathway, and/or transcription within the host cell. In some non-limiting embodiments, the one or more genes of interest are selected from the group of DVL2, WNT7B, NKD2, SOSTDC1, LRP6, FRAT2, TLE1, WWOX, BCL9, and CCND2.

Other screening methodologies are described in Mohr S E et al., "RNAi screening comes of age: improved techniques and complementary approaches," *Nat. Rev. Molec. Cell. Biol.* 2014; 15:591-600; Gaj T et al., "ZFN, TALEN, and CRISPR/Cas-based methods for genome engineering," *Trends Biotechnol.* 2013; 31(7):397-405; Shalem O et al., "High-throughput functional genomics using CRISPR-Cas9," *Nat. Rev. Genet.* 2015; 16:299-311; and Zhou Y et al., "High-throughput screening of a CRISPR/Cas9 library for functional genomics in human cells," Nature 2014; 509:487-91, each of which is incorporated herein by reference in its entirety.

Diseases Related to the Wnt Pathway, Including Viral Infections

The methods herein can be employed to treat any disease related to the Wnt pathway. Exemplary, non-limiting diseases include a viral infection, cancer (e.g., colon cancer, colorectal cancer, melanoma, thyroid cancer, ovarian cancer, hepatocellular carcinoma, breast cancer, prostate cancer, or lung cancer), neurological disease (e.g., Alzheimer's disease), osteoporosis, fibrosis, myocardial infarction, autoimmune disease (e.g., rheumatoid arthritis or colitis), and endocrine disease.

In particular embodiment, the disease is a viral infection. The infection can arise from a particular group of viruses (e.g., a negative-stranded, single-stranded RNA virus), family of viruses (e.g., a bunyavirus, an arenavirus, or an orthomyxovirus), and/or structure of viruses (e.g., a segmented RNA virus). Exemplary, non-limiting viruses include Rift Valley fever virus, hantavirus, California encephalitis virus, Crimean-Congo hemorrhagic fever virus, La Crosse virus, Lassa virus, Junin virus, Machupo virus, Guanarito virus, Chapare virus, Lujo virus, influenza A virus, or influenza B virus, as well as cancer-causing viruses (e.g., human papillomavirus, which can cause various types of cancers, including cervical cancer). Additional diseases are described in Kahn M, "Can we safely target the WNT pathway?," *Nat. Rev. Drug Discov.* 2014; 13(7):513-32, which is incorporated herein by reference in its entirety.

Wnt Pathway Inhibitory Compounds

The methods herein include the use of one of more Wnt pathway inhibitory compounds (e.g., one or more compounds having an inhibitory, activator, antagonist, or agonist activity on one or more proteins in the Wnt pathway). Exemplary Wnt pathway inhibitory compounds include a tankyrase inhibitor, a porcupine inhibitor, a destruction complex stabilizer, a β-catenin binder, a transcriptional activity inhibitor, an antibody (e.g., targeting a protein or receptor in the Wnt inhibitory pathway, such as vantictumab, OMP-18R5, or a Wnt3A-neutralizing antibody), a peptide or peptide mimetic, a decoy receptor (e.g., OMP-54F28), an RNAi inhibitor (e.g., a siRNA, shRNA, or microRNA targeting a protein or a gene encoding a protein in the Wnt pathway, such as the β-catenin protein or a gene encoding the β-catenin protein), a non-specific inhibitor, a Dishevelled (DVL) domain binder, as well as derivatives, isomers, analogues, fragments, and salts thereof. In some embodiments, one or more Wnt pathway inhibitory compounds are formulation as a medication (e.g., a vaccine optionally including any useful adjuvant).

Exemplary tankyrase inhibitors include JW67 (trispiro [3H-indole-3,2'-[1,3]dioxane-5',5"-[1,3]dioxane-2",3'''-[3H] indole]-2,2'''(1H,1'''H)-dione); JW55 (N-[4-[[4-(4-methoxyphenyl)oxan-4-yl]methylcarbamoyl]phenyl]furan-2-carboxamide); JW74 (4-[4-(4-methoxyphenyl)-5-[[[3-(4-methylphenyl)-1,2,4-oxadiazol-5-yl]methyl]thio]-4H-1,2,4-triazol-3-yl]-pyridine); Endo-IWR-1 (4-[(3aR,4S,7R,7aS)-1,3-dioxo-1,3,3a,4,7,7a-hexahydro-2H-4,7-methanoisoindol-2-yl]-N-(quinolin-8-yl)benzamide); XAV939 (2-[4-(trifluoromethyl)phenyl]-1,5,7,8-tetrahydro-thiopyrano[4,3-d]pyrimidin-4-one); PJ34 (2-(dimethylamino)-N-(6-oxo-5H-phenanthridin-2-yl)acetamide); WIKI4 (2-[3-[[4-(4-methoxyphenyl)-5-pyridin-4-yl-1,2,4-triazol-3-yl]sulfanyl]propyl]benzo[de]isoquinoline-1,3-dione); G007-LK (4-[5-[(E)-2-[4-(2-chlorophenyl)-5-(5-methylsulfonylpyridin-2-yl)-1,2,4-triazol-3-yl]ethenyl]-1,3,4-oxadiazol-2-yl]benzonitrile); G244-LM (2-[4-(2-methylsulfonylphenyl)piperazin-1-yl]-1,5,7,8-tetrahydrothiopyrano[4,3-d]pyrimidin-4-one); 2-[4-(4-fluorophenyl)piperazin-1-yl]-6-methylpyrimidin-4(3H)-one; NVP-TNKS656 (N-(cyclopropylmethyl)-2-[4-(4-methoxybenzoyl)piperidin-1-yl]-N-[(4-oxo-1,5,7,8-tetrahydropyrano[4,3-d]pyrimidin-2-yl)methyl]acetamide); tankyrase 1/2 inhibitor III (3-(4-methoxyphenyl)-5-((4-(4-methoxyphenyl)-5-methyl-4H-1,2,4-triazol-3-ylthio) methyl)-1,2,4-oxadiazole); N-(2-methoxyphenyl)-4-(3-(4-oxo-3,4-dihydroquinazolin-2-yl)propanamido)benzamide; 3-((4-oxo-3,4-dihydroquinazolin-2-yl)thio)-N-(trans-4-(5-phenyl-1,3,4-oxadiazol-2-yl)cyclohexyl)propanamide; and N-(trans-4-(4-cyanophenoxy)cyclohexyl)-3-((4-oxo-3,4-dihydroquinazolin-2-yl)thio)propanamide), as well as salts, isomers, analogues, and derivatives thereof.

Exemplary porcupine inhibitors include LGK974 (2-[5-methyl-6-(2-methylpyridin-4-yl)pyridin-3-yl]-N-(5-pyrazin-2-ylpyridin-2-yl)acetamide); IWP-2 (N-(6-methyl-1,3-benzothiazol-2-yl)-2-[(4-oxo-3-phenyl-6,7-dihydrothieno[3,2-d]pyrimidin-2-yl)sulfanyl]acetamide); and Wnt-C59 (2-[4-(2-methylpyridin-4-yl)phenyl]-N-(4-pyridin-3-ylphenyl)acetamide), as well as salts, isomers, analogues, and derivatives thereof.

Exemplary destruction complex stabilizers include JW67, JW74, and Endo-IWR-1, as well as salts, isomers, analogues, and derivatives thereof.

Exemplary β-catenin binders include PNU-74654 (N-[(5-methylfuran-2-yl)methylideneamino]-2-phenoxybenzamide); PKF115-584 ((1R)-2-[12-[(2R)-2-(benzoyloxy)propyl]-3,10-dihydro-4,9-dihydroxy-2,6,7,11-tetramethoxy-3,10-dioxo-1-perylenyl]-1-methylethylcarbonic acid 4-hydroxyphenyl ester or 1-[4,9-dihydroxy-12-[2-(4-hydroxyphenoxy)carbonyloxypropyl]-2,6,7,11-tetramethoxy-3,10-dioxoperylen-1-yl]propan-2-yl benzoate); PKF118-744 (3-butanoyl-1,8-dihydroxy-2-methylphenanthrene-9,10-dione); PKF222-815 (1-[4,9-dihydroxy-12-[2-(2,4-dihydroxy-6-methylbenzoyloxy)propyl]-2,6,7,11-tetramethoxy-3,10-dioxoperylen-1-yl]propan-2-yl 2,4-dihydroxy-3-methyl-benzoate); CGP049090 (5,12-dihydroxy-8,9-bis[(2s)-2-hydroxypropyl]-7,10-dimethoxyperylo[1,12-def][1,3]dioxepine-6,11-dione); PKF118-310 (1,6-dimethylpyrimido[5,4-e][1,2,4]triazine-5,7-dione); ZTM000990 (methyl 1,6,8,14a-tetrahydroxy-11-[(4-hydroxy-3,5-dimethoxy-6-methyloxan-2-yl)amino]-6a-methoxy-3-methyl-7,9,12,14-tetraoxo-5,6-dihydrobenzo[a]tetracene-2-carboxylate); BC21 (NCI-109268 or di-p-chlorobis[1-[(1-piperidinyl-κN)methyl]-2-naphthalenolato-κO]di-(9CI) copper); and CCT031374 (2-(1,2-dihydroimidazo[1,2-a]benzimidazol-4-yl)-1-(4-phenylphenyl)ethanone, including a hydrobromide salt thereof), as well as salts, isomers (e.g., stereoisomers), analogues, and derivatives thereof.

Exemplary transcriptional activity inhibitors (e.g., a β-catenin-TCF antagonist) include Wnt Pathway Inhibitor XII ((E)-4-(2,6-difluorostyryl)-N,N-dimethylaniline); FH535 (2,5-dichloro-N-(2-methyl-4-nitrophenyl)benzenesulfonamide); PKF115-584; PKF118-310; PKF118-744; PKF222-815; CGP049090; ZTM000990; PNU-74654; BC21; UU-T01 (1-hydroxy-5-[2-(2H-tetrazol-5-yl)ethyl]indazole); UU-T02 ((S)-4-((S)-3-carboxy-2-((S)-2-(2-(5-chloro-1H-indol-2-yl) acetamido)-3-(naphthalen-2-yl) propanamido) propanamido)-5-methoxy-5-oxopentanoic acid); UU-T03 ((S)-5-ethyl 1-methyl 2-((S)-2-((S)-2-(2-(5-chloro-1H-indol-2-yl) acetamido)-3-(naphthalen-2-yl) propanamido)-4-ethoxy-4-oxobutanamido) pentanedioate); curcumin ((1E,6E)-1,7-bis(4-hydroxy-3-methoxyphenyl)-1,6-heptadiene-3,5-dione); NC043 (15-oxospiramilactione); iCRT3 (2-[[[2-(4-ethylphenyl)-5-methyl-4-oxazolyl]methyl]thio]-N-(2-phenylethyl)acetamide); iCRT5 (4-[(5Z)-5-[(3,4-dimethoxyphenyl)methylidene]-4-oxo-2-sulfanylidene-1,3-thiazolidin-3-yl]butanoic acid); iCRT14 (iCRT-14 or (5Z)-5-[(2,5-dimethyl-1-pyridin-3-ylpyrrol-3-yl)methylidene]-3-phenyl-1,3-thiazolidine-2,4-dione); ICG-001 (PRI-724 or (6S,9aS)—N-benzyl-6-[(4-hydroxyphenyl)methyl]-8-(naphthalen-1-ylmethyl)-4,7-dioxo-3,6,9,9a-tetrahydro-2H-pyrazino[1,2-a]pyrimidine-1-carboxamide); a 2,4-diamino-quinazoline series compound (e.g., methyl 2-[4-[[[2-(methylamino)quinazolin-4-yl]amino]methyl]phenyl]benzoate; or N-[4-[[[2-(dimethylamino)-7-methylquinazolin-4-yl]amino]methyl]phenyl]-1-[(4-fluorophenyl)methyl]piperidine-4-carboxamide); calphostin C (1-[3,10-dihydroxy-12-[2-(4-hydroxyphenoxy)carbonyloxypropyl]-2,6,7,11-tetramethoxy-4,9-dioxoperylen-1-yl]propan-2-yl benzoate); OSU03012 (2-amino-N-[4-[5-phenanthren-2-yl-3-(trifluoromethyl)pyrazol-1-yl]phenyl]acetamide); 3,6-dihydroxyflavone; CCT031374; CCT036477 (N-[(4-chlorophenyl)-(2-methyl-1H-indol-3-yl)methyl]pyridin-2-amine); CCT070535 (3-benzyl-7-chloro-1-(4-chlorophenyl)-4-hydroxypyrimido[1,2-b]pyridazin-5-ium-2-one); ZTM000990; RFD (5,9-dimethoxy-1aH-phenanthrene-1,2-dione); and RFD-HY (5,9-hydroxy-1aH-phenanthrene-1,2-dione), as well as salts, isomers (e.g., stereoisomers), analogues, and derivatives thereof.

Exemplary DVL domain binders include NSC668036 (Boc-DL-Ala-DL-OVal-DL-Ala-DL-OVal-OHor 3-methyl-2-[2-[[3-methyl-2-[2-[(2-methylpropan-2-yl)oxycarbonylamino]propanoyloxy]butanoyl]amino]propanoyloxy]butanoic acid); FJ9 (2-[(1-hydroxypentyl]-6-methyl-3-(2-phenylethyl)-1H-indole-5-carboxylic acid); 3289-8625 (2-((3-(2-phenylacetyl)amino)benzoyl)amino)benzoic acid); and 3289-5066 (2-((3-(2-acetyl)amino)benzoyl)amino)benzoic acid), as well as salts, isomers (e.g., stereoisomers), analogues, and derivatives thereof.

Additional compounds and methods of synthesizing and testing such compounds are described in Harmon B et al., "A genome-wide RNAi screen identifies a role for Wnt/beta-catenin signaling during Rift Valley fever virus infection," *J. Virol.* doi:10.1128/JVI.00543-16 (posted online May 25, 2016, 49 pp.); Handeli S et al., "A small-molecule inhibitor of Tcf/β-catenin signaling down-regulates PPARγ and PPARδ activities," *Mol. Cancer Ther.* 2008; 7(3):521-9; Kahn M, "Can we safely target the WNT pathway?," *Nat. Rev. Drug Discov.* 2014; 13(7):513-32; Anastas J N et al., "WNT signalling pathways as therapeutic targets in cancer," *Nat. Rev. Cancer* 2013; 13(1):11-26; Voronkov A et al., "Wnt/beta-catenin signaling and small molecule inhibitors," *Curr. Pharm. Des.* 2012; 19(4):634-64; Halbedl S et al., "Synthesis of novel inhibitors blocking Wnt signaling downstream of β-catenin," *FEBS Lett.* 2013; 587(5):522-7; Hua Z et al., "Development of novel dual binders as potent, selective, and orally bioavailable tankyrase inhibitors," *J. Med. Chem.* 2013; 56(24):10003-15; Zhang W et al., "Fluorinated N,N-dialkylaminostilbenes for Wnt pathway inhibition and colon cancer repression," *J. Med. Chem.* 2011; 54(5):1288-97; Chen Z et al., "2,4-Diamino-quinazolines as inhibitors of beta-catenin/Tcf-4 pathway: potential treatment for colorectal cancer," *Bioorg. Med. Chem. Lett.* 2009; 19(17):4980-3; Huang Z et al., "Targeting the Tcf4 $G^{13}ANDE^{17}$ binding site to selectively disrupt β-catenin/T-cell factor protein-protein interactions," *ACS Chem. Biol.* 2014; 9(1):193-201; Ewan K et al., "A useful approach to identify novel small molecule inhibitors of Wnt-dependent transcription," *Cancer Res.* 2010; 70(14):5963-73; Fujii N et al., "An antagonist of Dishevelled protein-protein interaction suppresses β-catenin-dependent tumor cell growth," *Cancer Res.* 2007; 67(2):573-9; and Grandy D et al., "Discovery and characterization of a small molecule inhibitor of the PDZ domain of Dishevelled," *J. Biol. Chem.* 2009; 284(24): 16256-63, as well as U.S. Pat. Pub. Nos. US2016/0082014, US2015/0374696, US2015/0322057, US2015/0157633, US2015/0025114, US2014/0038922, US2014/0031374, US2014/0255426, US2012/0207857, and US2004/0204477, each of which is incorporated herein by reference in its entirety.

EXAMPLES

Example 1: A Genome-Wide RNAi Screen Identifies a Role for Wnt/β-Catenin Signaling During Rift Valley Fever Virus Infection Bunyaviruses constitute a diverse group of predominantly arthropod-vectored viruses of medical and agricultural importance with global distribution. Rift Valley fever virus (RVFV) is a particularly important bunyavirus due to its capacity to cause severe disease in humans, including retinal vasculitis, encephalitis, and fatal hepatitis with hemorrhagic fever, as well as lethal disease in economically valuable livestock species (see, e.g., Pepin M et al., "Rift Valley fever virus (Bunyaviridae: Phlebovirus): an update on pathogenesis, molecular epidemiology, vectors, diagnostics and prevention," *Vet. Res.* 2010; 41(6):61 (40 pp.)). Although currently endemic to the African continent and Arabian Peninsula, there is a growing concern for the spread of RVFV into geographic locations outside endemic regions (see, e.g., Rolin A I et al., "The risk of Rift Valley fever virus introduction and establishment in the United States and European Union," *Emerg. Microbes Infect.* 2013; 2(12):e81 (8 pp.)).

RVFV is also an agent of biodefense and agro-terrorism concern with the potential to cause social disruption requiring public health preparedness. For this reason, RVFV is classified as a Category A priority pathogen by the National Institute of Allergy and Infectious Diseases, a high-consequence pathogen by the World Organization for Animal Health, and the third most dangerous animal threat by the United States Department of Agriculture Animal and Plant Health Inspection Service after avian influenza and foot-and-mouth disease. Currently, there are no FDA-approved therapies or fully-licensed vaccines in the United States for use against RVFV or other pathogenic bunyaviruses. Lack of countermeasures against pathogenic bunyaviruses is partially due to gaps in knowledge of fundamental infection mechanisms and interactions between bunyaviruses and their host cells.

RVFV is an arthropod-borne virus that belongs to the *Phlebovirus* genera of the Bunyaviridae family. It is a spherical enveloped virus with three single-stranded RNA segments (L, M, and S segments) of negative or ambisense polarity that are encapsidated by the viral nucleocapsid (N) to form the ribonucleocapsid (RNP). The L segment encodes the viral RNA dependent RNA polymerase (RdRp), which is packaged with the viral RNA genome in the virus particle. The M segment encodes two structural glycoproteins (Gn and Gc) and two nonstructural proteins (NSm1 and NSm2). The S segment is ambisense; it encodes the structural nucleoprotein N in the antisense orientation and encodes the nonstructural protein NSs in the sense orientation (see, e.g., Hadjihannas M V et al., "Conductin/axin2 and Wnt signaling regulates centrosome cohesion," *EMBO Rep.* 2010; 11(4):317-24).

In particular, RVFV nonstructural proteins (NSs) plays an important role in RVFV pathogenesis as it interferes with the cellular antiviral immune response by inhibiting host transcription (e.g., inhibiting synthesis of alpha/beta interferon mRNAs) and by promoting degradation of the double-stranded RNA-dependent protein kinase (PKR) and TFIIH p62 (see, e.g., Ikegami T et al., "Rift Valley fever virus NSs mRNA is transcribed from an incoming anti-viral-sense S RNA segment," *J. Virol.* 2005; 79(18):12106-11; Billecocq A et al., "NSs protein of Rift Valley fever virus blocks interferon production by inhibiting host gene transcription," *J. Virol.* 2004; 78(18):9798-806; Ikegami T et al., "Dual functions of Rift Valley fever virus NSs protein: inhibition of host mRNA transcription and post-transcriptional down-regulation of protein kinase PKR," *Ann. NY Acad. Sci.* 2009; 1171 Suppl 1:E75-85; Ikegami T et al., "Rift Valley fever virus NSs protein promotes post-transcriptional downregulation of protein kinase PKR and inhibits eIF2α phosphorylation," *PLoS Pathog.* 2009; 5(2):e1000287 (17 pp.); Kalveram B et al., "NSs protein of Rift Valley fever virus promotes posttranslational downregulation of the TFIIH subunit p62," *J. Virol.* 2011; 85(13):6234-43; and Mansuroglu Z et al., "Nonstructural NSs protein of Rift Valley fever virus interacts with pericentromeric DNA sequences of the host cell, inducing chromosome cohesion and segregation defects," *J. Virol.* 2010; 84(2):928-39).

Various interactions between the virus and the host cell are known. For instance, the RVFV virions bind to cells and enter via pH-dependent caveolae-mediated endocytosis (see, e.g., Harmon B et al., "Rift Valley fever virus strain MP-12 enters mammalian host cells via caveola-mediated endocytosis," *J. Virol.* 2012; 86(23):12954-70). After viral uncoating, the viral RNP is released into the cytoplasm, where primary transcription occurs.

Primary transcription of bunyaviral mRNA is primed by host-derived mRNA methylated cap structures that are obtained by a cap-snatching mechanism similar to that used by the influenza A virus. Bunyaviral cap snatching involves two viral proteins: the N protein that recognizes the 5'-cap and 10-18 nucleotides of cellular mRNAs, as well as the RdRp that cleaves this fragment of mRNA and uses it to prime viral mRNA synthesis (see, e.g., Hopkins K C et al., "A genome-wide RNAi screen reveals that mRNA decapping restricts bunyaviral replication by limiting the pools of Dcp2-accessible targets for cap-snatching," *Genes Dev.* 2013; 27(13):1511-25; and Baer A et al., "Induction of DNA damage signaling upon Rift Valley fever virus infection results in cell cycle arrest and increased viral replication," *J. Biol. Chem.* 2012; 287(10):7399-410).

The 5'-cap on viral mRNA not only primes viral transcription but also protects the viral mRNA from host-mediated degradation and recruits host ribosomes for translation. Subversion of the host cell translation machinery and subsequent translation of these viral transcripts provide the protein products necessary for viral replication of the genome and further mRNA synthesis (secondary transcription).

Because viruses are obligate intracellular pathogens that rely on host cell machinery and pathways to complete their infection cycles, key cell signaling pathways regulating proliferation and differentiation responses are often prime targets of virus interaction and manipulation. A greater understanding of these interactions and how they relate to viral replication is useful for development of effective targeted antiviral therapeutics.

Various host cell cycle pathways will likely play a role in viral entry, replication, and propagation. One such pathway (the Wnt pathway) has been a reported target of a variety of viruses including human cytomegalovirus (HCMV) (see, e.g., Angelova M et al., "Human cytomegalovirus infection dysregulates the canonical Wnt/β-catenin signaling pathway," *PLoS Pathog.* 2012; 8(10):e1002959 (13 pp.)), hepatitis B virus (HBV) (see, e.g., Hsieh A et al., "Hepatitis B viral X protein interacts with tumor suppressor adenomatous polyposis coli to activate Wnt/β-catenin signaling," *Cancer Lett.* 2011; 300(2):162-72; and Cha M Y et al., "Hepatitis B virus X protein is essential for the activation of Wnt/beta-catenin signaling in hepatoma cells," *Hepatology* 2004; 39(6):1683-93), hepatitis C virus (HCV) (see, e.g., Liu J et al., "Enhancement of canonical Wnt/β-catenin signaling activity by HCV core protein promotes cell growth of hepatocellular carcinoma cells," *PLoS One* 2011; 6(11): e27496 (10 pp.)), human immunodeficiency virus (HIV) (see, e.g., Al-Harthi L, "Interplay between Wnt/β-catenin signaling and HIV: virologic and biologic consequences in the CNS," *J. Neuroimmune Pharmacol.* 2012; 7(4):731-9), as well as Epstein-Barr virus (EBV) and Kaposi's sarcoma-associated herpesvirus (KSHV) (see, e.g., Hayward S D et al., "Notch and Wnt signaling: mimicry and manipulation by gamma herpesviruses," *Science STKE* 2006; 2006(335): re4). In particular, HBV and HCV proteins activate Wnt signaling, and over-activation of Wnt signaling may contribute to hepatocellular carcinogenesis in chronic HBV/

HCV infections (see, e.g., Zhang X D et al., "Hepatitis B virus X protein accelerates the development of hepatoma," *Cancer Biol. Med.* 2014; 11(3):182-90; and Liu J et al., "Hepatitis C virus core protein activates Wnt/β-catenin signaling through multiple regulation of upstream molecules in the SMMC-7721 cell line," *Arch. Virol.* 2011; 156(6): 1013-23).

The Wnt/β-catenin pathway, or canonical Wnt pathway, is an evolutionarily conserved signaling cascade that involves activation of the transcriptional coactivator β-catenin (see, e.g., MacDonald B T et al., "Wnt/beta-catenin signaling: components, mechanisms, and diseases," *Dev. Cell.* 2009; 17(1):9-26). The Wnt/β-catenin signaling pathway is implicated in major physiologic cellular functions, such as proliferation, differentiation, and maintenance of pluripotency, while perturbations in this signaling cascade are associated with multiple types of cancer (see, e.g., Klaus A et al., "Wnt signalling and its impact on development and cancer," *Nat. Rev. Cancer* 2008; 8(5):387-98).

The canonical Wnt pathway is best described in the OFF and ON state. In the OFF state, or in the absence of extracellular Wnt ligands, cytoplasmic β-catenin is sequentially phosphorylated by the β-catenin destruction complex (DC), which in turn is composed of casein kinase 1α (CK1), glycogen synthase kinase 3 (GSK-3), the scaffold protein axin, and the tumor suppressor adenomatous polyposis coli (APC). Phosphorylated β-catenin is then targeted for ubiquitination and proteasomal degradation. In the ON state, Wnt ligands bind to the Frizzed (FZD) receptor, thereby resulting in recruitment of the co-receptor low density lipoprotein receptor-related proteins 5 or 6 (LRP5/6). Phosphorylation of LRP5/6 on its cytoplasmic tail then promotes binding and polymerization of dishevelled protein (Dvl) and sequestration of a component of the DC, i.e., axin. This in turn results in inactivation of the DC, a critical control element in promoting degradation of β-catenin. By inactivating the DC, β-catenin accumulates within the host cell's cytoplasm and then translocates to the nucleus.

In the nucleus, β-catenin promotes transcription of genes related to proliferation and survival by acting as a coactivator for the T cell factor/lymphoid enhancer factor (Tcf/Lef) family of transcription factors (see, e.g., MacDonald B T et al., *Dev. Cell.* 2009; 17(1):9-26; Klaus A et al., *Nat. Rev. Cancer* 2008; 8(5):387-98; Voronkov A et al., "Wnt/beta-catenin signaling and small molecule inhibitors," *Curr. Pharm. Des.* 2013; 19(4):634-64; Clevers H et al., "Wnt/β-catenin signaling and disease," *Cell* 2012; 149(6):1192-205; and Li V S et al., "Wnt signaling through inhibition of β-catenin degradation in an intact Axin1 complex," *Cell* 2012; 149(6):1245-56). Due to the importance of the Wnt/β-catenin pathway in diseases such as cancer, several preclinical therapeutic agents specifically targeting the Wnt pathway have been described, and some have recently entered clinical trials (see, e.g., Voronkov A et al., *Curr. Pharm. Des.* 2013; 19(4):634-64; and Kahn M, "Can we safely target the WNT pathway?," *Nat. Rev. Drug* Disc. 2014; 13(7):513-32).

The findings that pathogenic viruses manipulate the Wnt pathway for productive infection, together with the progress in the development of Wnt inhibitors for cancer treatments, suggests a new avenue for targeting these viruses by designing therapeutics that are host-directed. This approach is illustrated in a recent study that showed that Wnt inhibitors can effectively block HCMV replication (see, e.g., Kapoor A et al., "Wnt modulating agents inhibit human cytomegalovirus replication," *Antimicrob. Agents Chemother.* 2013; 57(6):2761-7).

As described herein, we validated the role of canonical Wnt signaling in RVFV infection using a number of different assays, including high-throughput genome-wide RNA interference (RNAi) screening. Genome-wide RNAi screening is a powerful tool for functional genomics with the capacity to systematically perturb cellular pathways and comprehensively analyze host-pathogen interactions. Genome-wide RNAi screening has uncovered several previously uncharacterized cellular host factors involved in the infection of HIV, West Nile virus, and influenza A virus (see, e.g., Brass A L et al., "Identification of host proteins required for HIV infection through a functional genomic screen," *Science* 2008; 319(5865):921-6; Karlas A et al., "Genome-wide RNAi screen identifies human host factors crucial for influenza virus replication," *Nature* 2010; 463(7282):818-22; and Krishnan M N et al., "RNA interference screen for human genes associated with West Nile virus infection," *Nature* 2008; 455(7210):242-5).

More recently, RNAi screening against the bunyaviruses Uukuniemi virus and RVFV has revealed roles for host proteins VAMP3 and the decapping enzyme Dcp2, respectively, during bunyavirus infection (see, e.g., Hopkins K C et al., *Genes Dev.* 2013; 27(13):1511-25; and Meier R et al., "Genome-wide small interfering RNA screens reveal VAMP3 as a novel host factor required for Uukuniemi virus late penetration," *J. Virol.* 2014; 88(15):8565-78). However, a large-scale RNAi screen against RVFV in human cells has yet to be described.

To identify cellular factors required for RVFV infection in humans, we completed a genome-wide small interfering RNA (siRNA)-based screen, silencing ~22,909 human genes in HeLa cells, and identified 381 genes whose knockdown reduced RVFV infection. After grouping these 381 gene hits into functional clusters along cellular pathways, the Wnt signaling pathway was the most represented. In particular, we demonstrated activation of Wnt signaling by RVFV infection, enhancement of RVFV infection in cells pre-stimulated with Wnt ligands, and inhibition of RVFV infection using perturbations of Wnt signaling components at or downstream of the DC.

Furthermore, we obtained similar results using wild-type RVFV and the distantly related bunyaviruses La Crosse virus (LCV) and California encephalitis virus (CEV), which indicates a conserved bunyaviral replication mechanism involving Wnt signaling. In the context of current literature and without wishing to be limited by mechanism, we postulate that bunyaviruses activate Wnt responsive genes to regulate optimal cell cycle conditions for efficient viral replication (see, e.g., Hopkins K C et al., Genes Dev. 2013; 27(13):1511-25; and Baer A et al., *J. Biol. Chem.* 2012; 287(10):7399-410). We anticipate this new understanding of the fundamental mechanisms of bunyavirus infection will aid in the design of efficacious broad-spectrum host-directed antiviral therapeutics. Details of this study are provided in the following Examples.

Example 2: Experimental Materials and Methods

Cells, Viruses, and Reagents:

All cell lines were maintained in culture medium supplemented with 10% fetal bovine serum (FBS), 100 pig/ml of penicillin, and 100 units/ml of streptomycin (Life Technologies, Thermo Fisher Scientific Inc., Waltham, Mass.) at 37° C. under 5% $CO_2$. HeLa (human cervix carcinoma), 293T (human embryonic kidney), and A549 (human lung epithelial) cells were cultured in Dulbecco's Modified Eagle Medium; Vero (African green monkey kidney) cells were cultured in Minimum Essential Medium alpha. Primary human hepatocytes were obtained from ScienCell Research Laboratories, Inc. (Carlsbad, Calif.) and cultured using hepatocyte medium according to company's instructions.

Wild-type Rift Valley Fever virus strain ZH501, NR-37378, (wild-type RVFV), recombinant Vaccinia virus expressing GFP, derived from the Western Reserve strain NR-624 (VacV) (see, e.g., Earl P L et al., "Development and use of a vaccinia virus neutralization assay based on flow cytometric detection of green fluorescent protein," *J. Virol.* 2003; 77(19):10684-8), La Crosse Virus NR-540 (LCV), and California Encephalitis Virus, BFS-283, NR-89 (CEV), were obtained through NIH Biodefense and Emerging Infections Research Resources Repository, NIAID, NIH. The recombinant RVFV vaccine strain MP12 generated to carry a green fluorescent protein (GFP) gene (RVFV MP12-GFP) in place of the NSs gene has been described previously (see, e.g., Ikegami T et al., "Rescue of infectious Rift Valley fever virus entirely from cDNA, analysis of virus lacking the NSs gene, and expression of a foreign gene," *J. Virol.* 2006; 80(6):2933-40). Authentic non-recombinant RVFV strain MP12 was obtained from C. J. Peters (University of Texas Medical Branch). The recombinant Vesicular Stomatitis virus expressing GFP (VSV), derived from the Indiana serotype 1 strain (see, e.g., MacDonald B T et al., *Dev. Cell.* 2009; 17(1):9-26; Klaus A et al., *Nat. Rev. Cancer* 2008; 8(5):387-98; Kahn M, *Nat. Rev. Drug Disc.* 2014; 13(7):513-32; and Ebert O et al., "Oncolytic vesicular stomatitis virus for treatment of orthotopic hepatocellular carcinoma in immune-competent rats," *Cancer Res.* 2003; 63(13):3605-11) was obtained from A. Garcia-Sastre (Mount Sinai School of Medicine). Studies using RVFV ZH-501 were conducted under Biosafety Level 3 containment using established standard operating procedures.

Wild-type RVFV, RVFV MP12, RVFV MP12-GFP, LCV, CEV, and VSV-GFP were propagated in Vero cells, while VacV-GFP was grown in BSC-40 cells. The viral titers for wild-type RVFV, RVFV MP12, RVFV MP12-GFP, VSV-GFP, CEV, and LCV were quantified in Vero cells by using a standard plaque assay consisting of an agarose overlay with crystal violet staining. VacV-GFP plaque forming units (PFUs) were obtained by dilution of the virus and infection of BSC-40 cells without an agarose overlay (see, e.g., Harmon B et al., *J. Virol.* 2012; 86(23):12954-70). For qRT-PCR, RVFV MP12 and RVFV MP12-GFP stocks were first purified over a 20% sucrose cushion through ultracentrifugation.

Recombinant DKK-1, WIF-1, and purified Wnt3A (R&D Systems) were reconstituted in phosphate buffered saline (PBS) containing 0.1% bovine serum albumin (BSA). All other inhibitors were from EMD Millipore Corp. (Billerica, Mass.) and were initially resuspended in dimethyl sulfoxide (DMSO) followed by dilution in complete medium to obtain the final concentrations indicated. As a control for the DMSO-based inhibitors, cells were incubated with 50 µM DMSO alone, representing the highest concentration of DMSO used. Unless otherwise indicated, all experimental conditions were performed in triplicate, three or more times.

High-Throughput siRNA Screening:

The primary screen was performed using the Qiagen® human whole genome set (Qiagen N.V., Hilden, Germany), the Agilent V11 Bravo Automated Liquid Handler (Agilent Technologies Inc., Santa Clara, Calif.), and the Thermo Scientific™ Combidrop (Thermo Fisher Scientific, Inc.). Pooled siRNAs (4 per target, 50 nM final concentration) were complexed with Lipofectamine® RNAiMAX™ (Catalog no.: 13778500, 0.1 µl/well in 0.5 µl of Opti-MEM™, Life Technologies, Thermo Fisher Scientific Inc.). After 20 minutes, HeLa cells (about 3,000 cells/well) were added to each well. Cells were infected with RVFV MP12-GFP at a multiplicity of infection (MOI) of 1 at 48 hours post transfection (hpt) for 3 hours (h); then the cells were washed with PBS and were incubated in complete medium overnight.

At 24 hours post infection (hpi), alamarBlue® (AB) and GFP fluorescence were measured to calculate normalized infection values as previously described (see, e.g., Harmon B et al., *J. Virol.* 2012; 86(23):12954-70). In all of our assays, we used a fluorescence-based readout of AB that have been demonstrated to be highly sensitive (as few as 50 cells in a 96-well plate could be detected with relatively short incubations) and linear with a signal that is proportional to cell number. To verify manufacturer claims, cell titration experiments with the AB reagent were performed during screen optimization, and a linear increase in signal with increasing concentrations of seeded cells in 384-well and 96-well plates was demonstrated. For every plate in the initial screen, secondary screen, and follow-up analysis, AB cell viability tests were performed. Any siRNA-containing wells that demonstrated toxicity (1.25× reduction in 560/590 fluorescence, as compared to wells without siRNA) were removed/eliminated from the hit list and not included in the presented analysis. Sample means and standard deviation (S.D.) of negative controls were calculated plate-wise and used to set a z-score threshold value of −3. To be considered a hit, each replicate needed to be 3 S.D. from the mean.

Secondary Screen and Final Hit Selection:

To test the hits identified from the primary screen, the siRNA hits from the master plates were picked and spotted on three new daughter plates using the Beckman-Coulter BioMek® NX with Span-8 system. The screen was performed at Sandia National Laboratories using the BioTek EL406™ microplate washer and dispenser using the reverse transfection, infection, and analysis assays described above.

Final Hit Selection Data Analysis:

Final hit selection was based on a uniformly minimal variance unbiased estimate (UMVUE) of strictly standardized mean differences (SSMD) using the paired method formula:

$$\frac{\Gamma\left(\frac{n-1}{2}\right)}{\Gamma\left(\frac{n-2}{2}\right)}\sqrt{\frac{2}{n-1}}\frac{d_i}{s_i},$$

where n is the number of replicates, $d_i$ is the sample mean, and si is the S.D. for the ith siRNA. A meaningful and interpretable SSMD-based criterion for classifying the size of siRNA effects is as follows: |SSMD|≥5 for extremely strong, 5>|SSMD|≥3 for very strong, 3>|SSMD|≥2 for strong, 2>|SSMD|≥1.645 for fairly strong, 1.645>|SSMD|≥1.28 for moderate, 1.28>|SSMD|≥1 for fairly moderate, 1>|SSMD|≥0.75 for fairly weak, 0.75>|SSMD|≥0.5 for weak, 0.5>|SSMD|≥0.25 for very weak, and |SSMD|>0.25 for extremely weak effects (see, e.g., Zhang XD, "Illustration of SSMD, z score, SSMD*, z* score, and t statistic for hit selection in RNAi high-throughput screens," *J. Biomol. Screen.* 2011; 16(7):775-85). Therefore, a threshold of −1.30 was set as a cutoff value to identify moderate to extremely strong siRNA hits that reduced RVFV MP12-GFP infection.

β-Catenin siRNA Treatment:

Silencer® Select siRNAs (Catalog number: AM16708) targeting the β-catenin gene (Life Technologies) and scrambled control siRNA (AllStars negative-control siRNA, Qiagen N.V.) were transfected into HeLa or 293T cells using Lipofectamine® RNAiMAX™. At 60 hpt, cells were infected with indicated viruses (MOI=1) for 3 h, followed by a PBS wash and incubation in complete medium overnight. AB and GFP fluorescence signals were then measured to calculate normalized infection values.

Western Blot Analysis:

Samples were lysed and analyzed by Western blot as previously described (see, e.g., Harmon B et al., *J. Virol.* 2012; 86(23):12954-70). Primary antibody for β-catenin knockdown experiments was rabbit polyclonal anti-β-catenin (H-102, Santa Cruz Biotechnology, Inc., Dallas, Tex.). Primary antibody to measure levels of β-catenin activation was non-phospho (Active) β-catenin (Ser33/37/Thr41) (D13A1) rabbit monoclonal antibody (Cell Signaling Technology, Inc., Danvers, Mass.). All blots were re-probed with rabbit anti-actin polyclonal antibody (Novus Biologicals LLC, Littleton, Colo.). The relative reduction index (RI) was calculated as the quotient of the densitometry signal for the target protein band divided by that for actin, which was then normalized by the ratio obtained with scrambled siRNA or no ligand controls (considered to be 1).

β-Catenin Transcriptional Reporter Assay:

TOPflash (TCF/LEF-1 reporter plasmid) or FOPFlash (contains mutated TCF/LEF-1 binding sites) were co-transfected with pcDNA3.1-GFP or pcDNA3.1-mKate (used with GFP expressing viruses, Thermo Fisher Scientific, Inc.) to serve as an internal transfection control and to control for effects on overall gene expression, using TransIT®-LT1 transfection reagent (Mirus Bio LLC, Madison, Wis.) according to manufacturer's protocol. Luciferase activity was assayed using Bright-Glo™ luciferase reporter assay kit (Promega Corp., Madison, Wis.) according to manufacturer's protocol. Intensity is shown as relative light units (RLU). Cells were treated with Wnt3A or with the indicated virus at 18 hpt. For cells co-transfected with TOPflash/pcDNA3.1-GFP/mKate and treated with 100 ng/ml of Wnt3A or indicated virus concentrations, the measured luciferase activity was normalized to the GFP (488/510) or mKate (588/633) expression signal. Fold activation was calculated by dividing the relative luciferase activity of treated/infected cells with that of untreated cells. The relative percentage of luciferase activity was determined by subtracting the uninfected/unstimulated cells as background and taking NI/DMSO condition and infected/Wnt3A stimulated samples as 100%. For TOPflash-expressing 293T cells treated with inhibitors, all conditions included treatment of cells with each inhibitor concentration as indicated, prior to and during treatment with Wnt3A, no virus (mock infection), and with indicated viruses. Inhibitors had no effect on luciferase activity in the mock-infected wells, and the luciferase activity from these wells was subtracted as background.

Quantitative Real-Time RT-PCR:

Total RNA was isolated and purified with ZR RNA MiniPrep™ extraction kit (Zymo Research Corp., Irvine, Calif.), and cDNA was made using the SuperScript® VILO™ cDNA Synthesis Kit (Life Technologies). The primer sets, probe sets, and TaqMan Gene Expression Master Mix were purchased from Applied Biosystems® (Thermo Fisher Scientific Inc.), and gene expression measurements were analyzed on a Bio-Rad CFX96™. Each experimental condition was run in triplicate, and the relative amount of target gene mRNA was normalized to GAPDH mRNA.

Infection Assays in Wnt Ligand Stimulated Cells:

Cells were incubated in medium alone or at increasing concentrations of Wnt3A for 20 h and then treated for 3 h with virus. Cells were then washed with PBS and incubated in complete medium at 37° C. for 14 to 16 h. AB and GFP fluorescence signals were then measured to calculate normalized infection values. Levels of virus infection enhancement were measured by fold changes between Wnt-simulated/infected conditions, as compared to unstimulated/infected controls. These experiments were performed in triplicate for each cell type for three or more times. For pre-treatment of HeLa cells with Wnt3A prior to infection with wild-type RVFV, HeLa cells were untreated or treated with 50 ng/ml of Wnt3A for 20 h prior to and during either a period of a 36 h mock infection or a period of infection with wild-type RVFV (MOI=0.1). After 36 h, supernatants were collected, and virus titers were quantified by a standard plaque assay on Vero cells.

Inhibitor Treatment, Time-of-Addition Experiments, Plaque Assays, and Flow Cytometry:

For most experiments, cells were incubated with medium alone (no inhibitor=NI), DMSO, or individual inhibitors for 1 h prior to and during incubation with viruses or Wnt3A. If an infection continued overnight, virus was removed, cells were washed with PBS, and inhibitors were added back in complete medium for 16 h before relative percent infection was measured.

For time-of-addition experiments, pre-treatment samples (pre-treat condition) were incubated with indicated concentrations of inhibitors for 1 h prior to and during 3 h infection. Virus and inhibitors were then removed by washing once with PBS, and cells were incubated in compete medium alone overnight (no inhibitor added back). Alternatively, untreated cells (post-treat condition) were incubated with virus for 1 h, washed with PBS to remove unbound virus, and then incubated with inhibitors in complete medium for 16 h before relative percent infection was measured. To measure viral titers of wild-type RVFV, RVFV MP12, CEV, and LCV, supernatants were removed at the indicated times post-infection and titered by a standard plaque assay on Vero cells.

Figures 7A, 7B:
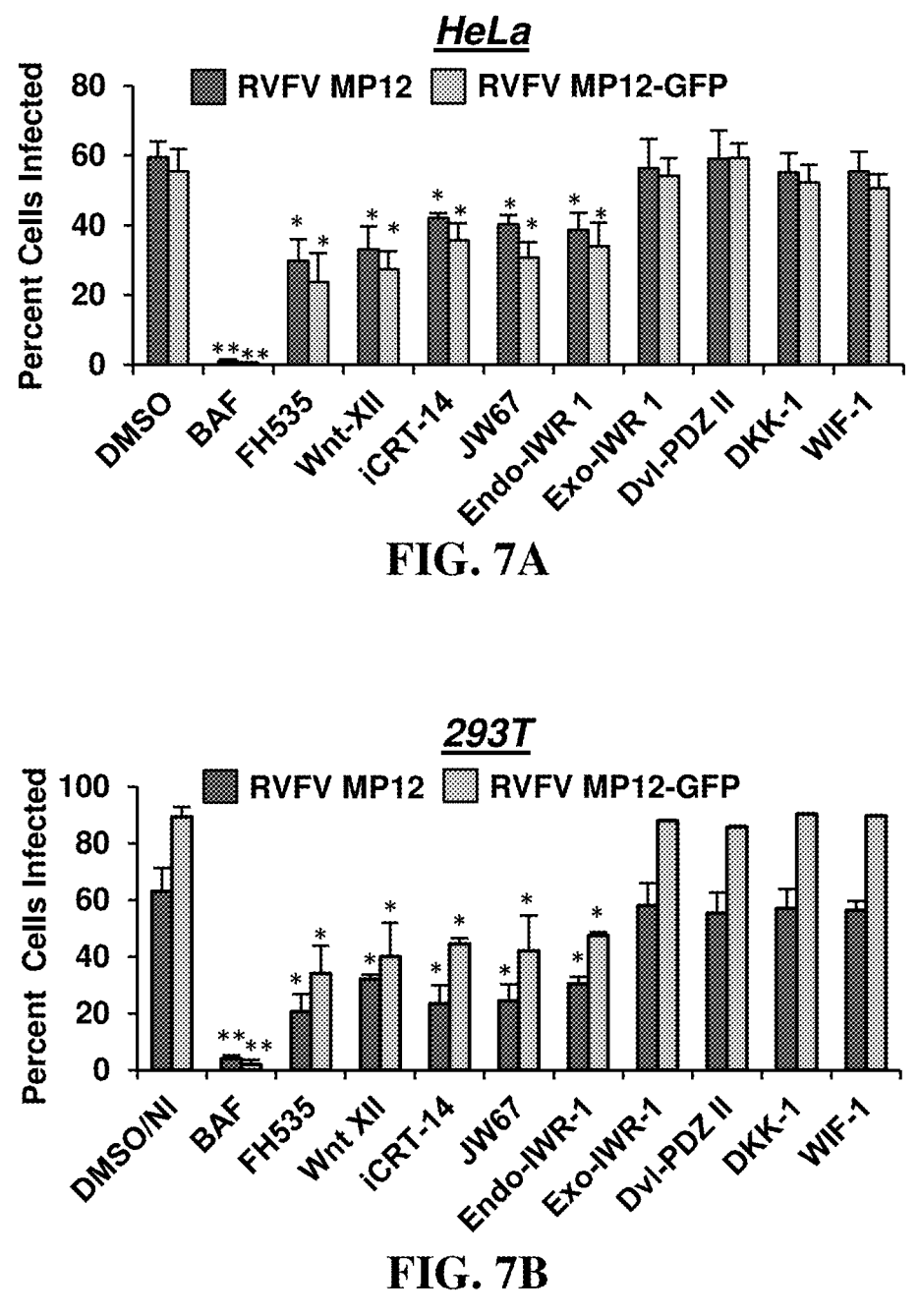
Figure 7C:
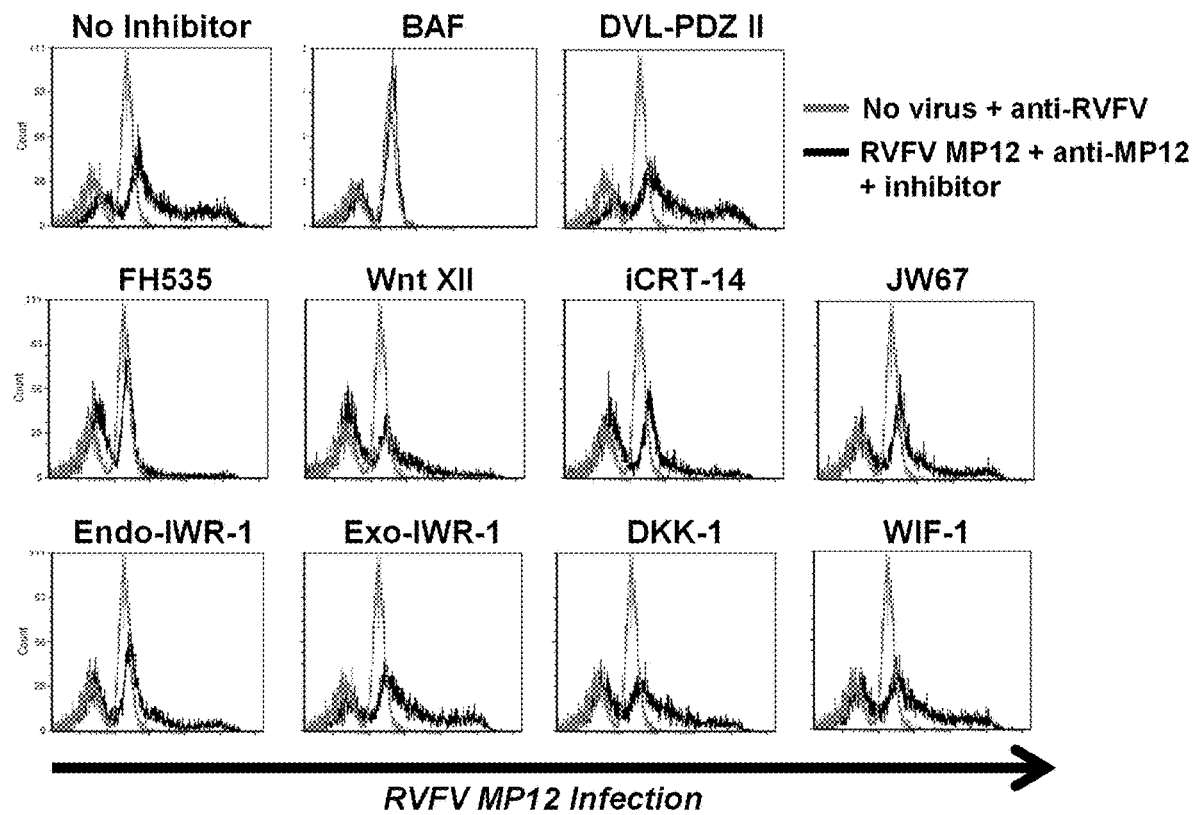

For flow cytometry experiments, 293T cells were incubated with indicated concentrations of inhibitors for 1 h prior to and during the 16 h infection with virus (MOI=3). Viral antigens were detected by immunofluorescence as previously described (see, e.g., Harmon B et al., *J. Virol.* 2012; 86(23):12954-70). For RVFV MP12 infected samples, anti-RVFV mouse polyclonal antibody (provided by R. Tesh of UTMB) was used as the primary antibody, and Alexa Fluor® 488 goat anti-mouse IgG (Invitrogen™, Thermo Fisher Scientific Inc.) was used as a secondary antibody. Cells were analyzed using an Accuri™ C6 flow cytometer with FCS Express software (De Novo Software, Los Angeles, Calif.). Cells were counted as infected if their FL-1 fluorescence was greater than that of the untreated or DMSO-treated, uninfected cells (FIG. 7C, gray histograms). The quantity of cells infected is given as percent cells infected. The average (+S.D.) of four independent experiments is shown. Uninfected cells were similarly probed with primary and secondary antibody to control for any nonspecific binding.

Statistical Analysis:

Raw data for infection assays measured by GFP fluorescence were compared using a two-tailed t-test for each individual experiment. Values obtained with inhibitors suspended in DMSO were compared to DMSO-treated samples; and values obtained with inhibitors suspended in water were compared to infected, untreated samples. For siRNA treated samples, values obtained from wells transfected with indicated siRNA constructs were compared to values obtained with wells transfected with scrambled siRNA on the same plate. For plate assays, untreated and DMSO-treated controls, or scrambled siRNA and GFP siRNA, were included on every plate, with no virus, RVFV MP12-GFP, VacV and VSV. Inhibitor-treated or siRNA-transfected cells that were infected with wild-type RVFV, RVFV MP12, or RVFV MP12-GFP were compared to control samples infected with the same virus, as was the case for VacV and VSV.

For qRT-PCR, the $C_t$ values obtained with virus-infected samples were compared to $C_t$ values of mock-infected samples using a two-tailed t-test for each individual experiment. P values were considered significant when they were <0.05 (*) and very significant when they were <0.01 (), <(*), or <0.0001 (****). The P values shown in the figures and text were based on the highest P values obtained from three independent experiments.

Example 3: Genome-Wide RNAi Screening Reveals a Role for Wnt/β-Catenin Signaling in RVFV Infection Rift Valley fever virus (RVFV) is an arbovirus within the Bunyaviridae family capable of causing serious morbidity and mortality in humans and livestock. To identify host factors involved in bunyavirus replication, we employed genome-wide RNA interference (RNAi) screening and identified 381 genes whose knockdown reduced infection. The Wnt pathway was the most represented pathway when gene hits were functionally clustered. With further investigation, we found that RVFV infection-activated Wnt signaling was enhanced when Wnt signaling was pre-activated, reduced with knockdown of β-catenin, and blocked using Wnt signaling inhibitors.

Similar results were found using distantly related bunyaviruses La Crosse virus and California encephalitis virus, suggesting a conserved role for Wnt signaling in bunyaviral infection. We propose a model in which bunyaviruses activate Wnt responsive genes to regulate optimal cell cycle conditions needed to promote efficient viral replication. The findings in this study should aid in the design of efficacious host-directed anti-viral therapeutics, as described herein.

To identify novel cellular factors involved in RVFV infection, we conducted a comprehensive high-throughput screen using genome-wide RNAi (FIG. 1A, as detailed in Example 2). The screen was performed in HeLa cells by targeting human genes with pools of four different siRNAs against each gene. To easily characterize the percentage of cells infected in a population, we used the recombinant GFP reporter virus of the attenuated RVFV strain MP12 (RVFV MP12-GFP) for the screen (see, e.g., Harmon B et al., *J. Virol.* 2012; 86(23):12954-70; and Ikegami T et al., *J. Virol.* 2006; 80(6):2933-40). The GFP gene in the RVFV MP12-GFP reporter virus replaced the nonstructural protein NSs, and GFP expression served as a sensitive readout of viral infection (see, e.g., Ikegami T et al., *J. Virol.* 2006; 80(6): 2933-40; and Kuri T et al., "Species-independent bioassay for sensitive quantification of antiviral type I interferons," *Virol. J.* 2010; 7:50 (6 pp.)). In brief, HeLa cells were seeded into 384-well plates, reverse transfected with siRNA in triplicate for two days, and then infected with RVFV MP12-GFP (MOI=1). One day later, the cells were analyzed with a quantitative cell viability reagent (alamarBlue®, AB) and then were lysed and assayed for GFP expression as a marker of virus replication (see, e.g., Kuri T et al., *Virol. J.* 2010; 7:50 (6 pp.)). GFP signals were normalized to cell number values, and control experiments were set to 100% infection.

For this primary screen, hit selection was based on Z-score statistics; this method was used because the large number of siRNAs typically produces a frequency distribution with an approximate Gaussian curve, albeit with a slight skew (see, e.g., Teferi W M et al., "A whole-genome RNA interference screen for human cell factors affecting myxoma virus replication," *J. Virol.* 2013; 87(8):4623-41). Using a Z-score threshold set at −3, or 3 standard deviations (SD) from the mean, we focused our genes of interest to only those that decreased RVFV MP12-GFP infection and identified 2,053 gene targets.

Figure 1B:
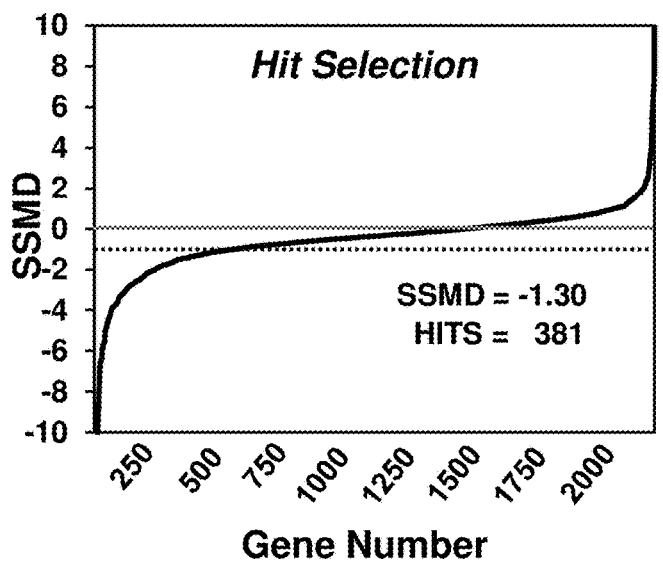

To validate the primary hits, the 2,053 siRNAs were re-plated and re-screened using the same transfection and infection protocol described above. Hit selection for the secondary screen was based on strictly standardized mean differences (SSMD), which minimizes the rates of false discovery and false non-discovery in siRNA-based screens and is calculated based on controls and replicates rather than a large sample size needed for Z-score statistics (see, e.g., Zhang XD, *J. Biomol. Screen.* 2011; 16(7):775-85). A SSMD score was calculated for each gene in the secondary screen using the means of the replicates after prior normalization using plate means. The SSMD threshold was set to −1.30, which resulted in 381 gene hits that reduced infection upon their knockdown (FIG. 1B). The final hit list is shown in Table I, and bolded genes are hits in Wnt pathway when analyzed by PANTHER (pantherdb.org).

TABLE I

RNAi screening dataset and pathway analysis

| Gene No. | SSMD value | Gene Symbol | Gene name |
| --- | --- | --- | --- |
| 1 | −13.647098 | GCNT2 | glucosaminyl (N-acetyl) transferase 2, I-branching enzyme (I blood group) |
| 2 | −12.981596 | F13B | coagulation factor XIII, B polypeptide |
| 3 | −12.794716 | COL13A1 | collagen, type XIII, alpha 1 |
| 4 | −12.639579 | USP36 | ubiquitin specific peptidase 36 |
| 5 | −12.048617 | MPV17 | MpV17 mitochondrial inner membrane protein |
| 6 | −11.5859 | BAT3 | HLA-B associated transcript 3 |
| 7 | −11.16801 | TIMM8B | translocase of inner mitochondrial membrane 8 homolog B (yeast) |
| 8 | −10.924384 | CD82 | CD82 molecule |
| 9 | −10.788172 | B4GALT2 | UDP-Gal:betaGlcNAc beta 1,4-galactosyltransferase, polypeptide 2 |

TABLE I-continued

RNAi screening dataset and pathway analysis

| Gene No. | SSMD value | Gene Symbol | Gene name |
|---|---|---|---|
| 10 | −10.734738 | HSP90AA1 | heat shock protein 90 kDa alpha (cytosolic), class A member 1 |
| 11 | −10.27683 | SLC7A6OS | solute carrier family 7, member 6 opposite strand |
| 12 | −10.090171 | CRISPLD1 | cysteine-rich secretory protein LCCL domain containing 1 |
| 13 | −9.937251 | NQO2 | NAD(P)H dehydrogenase, quinone 2 |
| 14 | −9.3960618 | RNF151 | ring finger protein 151 |
| 15 | −9.0085345 | ABCF3 | ATP-binding cassette, sub-family F (GCN20), member 3 |
| 16 | −8.8497987 | AHNAK | AHNAK nucleoprotein |
| 17 | −8.2738826 | ZFAND5 | zinc finger, AN1-type domain 5 |
| 18 | −7.7833484 | WNT7B | wingless-type MMTV integration site family, member 7B |
| 19 | −7.2680477 | TGM1 | transglutaminase 1 (K polypeptide epidermal type I, protein-glutamine-gamma-glutamyltransferase) |
| 20 | −6.9752098 | PLAGL2 | pleiomorphic adenoma gene-like 2 |
| 21 | −6.7470609 | RAPH1 | Ras association (RalGDS/AF-6) and pleckstrin homology domains 1 |
| 22 | −6.6289882 | PILRB | paired immunoglobin-like type 2 receptor beta |
| 23 | −6.5817388 | KRT6B | keratin 6B |
| 24 | −6.4408221 | OR5D16 | olfactory receptor, family 5, subfamily D, member 16 |
| 25 | −6.4272662 | C19orf55 | chromosome 19 open reading frame 55 |
| 26 | −6.4171588 | ZCCHC5 | zinc finger, CCHC domain containing 5 |
| 27 | −6.3937532 | FBLN7 | fibulin 7 |
| 28 | −6.2780553 | PPAPDC2 | phosphatidic acid phosphatase type 2 domain containing 2 |
| 29 | −5.8896278 | TLE1 | transducin-like enhancer of split 1 (E(sp1) homolog, Drosophila) |
| 30 | −5.8514364 | ZNF160 | zinc finger protein 160 |
| 31 | −5.8450349 | VAV1 | vav 1 guanine nucleotide exchange factor |
| 32 | −5.7349075 | TEKT4 | tektin 4 |
| 33 | −5.7222699 | AUTS2 | autism susceptibility candidate 2 |
| 34 | −5.7188418 | FKBP2 | FK506 binding protein 2, 13 kDa |
| 35 | −5.6658474 | NFRKB | nuclear factor related to kappaB binding protein |
| 36 | −5.6240082 | RHBDD3 | rhomboid domain containing 3 |
| 37 | −5.5963892 | WWOX | WW domain containing oxidoreductase |
| 38 | −5.5525774 | NLRP4 | NLR family, pyrin domain containing 4 |
| 39 | −5.26969 | IGF1 | insulin-like growth factor 1 (somatomedin C) |
| 40 | −5.0401363 | LRCH2 | leucine-rich repeats and calponin homology (CH) domain containing 2 |
| 41 | −5.008961 | VDAC1 | voltage-dependent anion channel 1 |
| 42 | −4.9534945 | HEYL | hairy/enhancer-of-split related with YRPW motif-like |
| 43 | −4.8978417 | OR10G8 | olfactory receptor, family 10, subfamily G, member 8 |
| 44 | −4.8739219 | SULT1B1 | sulfotransferase family, cytosolic, 1B, member 1 |
| 45 | −4.8169057 | UBASH3A | ubiquitin associated and SH3 domain containing, A |
| 46 | −4.8003857 | SCN4B | sodium channel, voltage-gated, type IV, beta |
| 47 | −4.7843685 | LALBA | lactalbumin, alpha- |
| 48 | −4.5767519 | NDUFA2 | NADH dehydrogenase (ubiquinone) 1 alpha subcomplex, 2, 8 kDa |
| 49 | −4.5546259 | CCT6B | chaperonin containing TCP1, subunit 6B (zeta 2) |
| 50 | −4.5536652 | LRRC39 | leucine rich repeat containing 39 |
| 51 | −4.5435549 | UBE2C | ubiquitin-conjugating enzyme E2C |
| 52 | −4.4671726 | NDUFB5 | NADH dehydrogenase (ubiquinone) 1 beta subcomplex, 5, 16 kDa |
| 53 | −4.4381912 | GSTA3 | glutathione S-transferase A3 |
| 54 | −4.3720231 | RFC2 | replication factor C (activator 1) 2, 40 kDa |
| 55 | −4.3705947 | TARP | TCR gamma alternate reading frame protein |
| 56 | −4.3705893 | NSF | N-ethylmaleimide-sensitive factor |
| 57 | −4.3627677 | ZNF700 | zinc finger protein 700 |
| 58 | −4.246365 | PTMA | prothymosin, alpha (gene sequence 28) |
| 59 | −4.1518114 | PRAM1 | PML-RARA regulated adaptor molecule 1 |
| 60 | −4.1480465 | NKD2 | naked cuticle homolog 2 (Drosophila) |
| 61 | −4.139888 | ADAT2 | adenosine deaminase, tRNA-specific 2, TAD2 homolog (S. cerevisiae) |
| 62 | −4.0354898 | NCBP1 | nuclear cap binding protein subunit 1, 80 kDa |
| 63 | −3.9828251 | KLHL20 | kelch-like 20 (Drosophila) |
| 64 | −3.9658862 | MRS2 | MRS2 magnesium homeostasis factor homolog (S. cerevisiae) |
| 65 | −3.9338081 | CST3 | cystatin C (amyloid angiopathy and cerebral hemorrhage) |
| 66 | −3.878439 | FRAT2 | frequently rearranged in advanced T-cell lymphomas 2 |
| 67 | −3.8745775 | UBL4B | ubiquitin-like 4B |
| 68 | −3.8460546 | SLC14A2 | solute carrier family 14 (urea transporter), member 2 |
| 69 | −3.8419068 | ANKRD32 | ankyrin repeat domain 32 |

TABLE I-continued

RNAi screening dataset and pathway analysis

| Gene No. | SSMD value | Gene Symbol | Gene name |
|---|---|---|---|
| 70 | −3.8374495 | PDGFB | platelet-derived growth factor beta polypeptide (simian sarcoma viral (v-sis) oncogene homolog) |
| 71 | −3.8289719 | PZP | pregnancy-zone protein |
| 72 | −3.8184934 | MT3 | metallothionein 3 |
| 73 | −3.792868 | CCL5 | chemokine (C-C motif) ligand 5 |
| 74 | −3.7854289 | MYO10 | myosin X |
| 75 | −3.7836493 | UBE2C | ubiquitin-conjugating enzyme E2C |
| 76 | −3.7539061 | STAM | signal transducing adaptor molecule (SH3 domain and ITAM motif) 1 |
| 77 | −3.7439903 | CFI | complement factor I |
| 78 | −3.734487 | CCNG1 | cyclin G1 |
| 79 | −3.7281283 | F12 | coagulation factor XII (Hageman factor) |
| 80 | −3.7274613 | LY6H | lymphocyte antigen 6 complex, locus H |
| 81 | −3.6620612 | LAMP1 | lysosomal-associated membrane protein 1 |
| 82 | −3.6395535 | HOM-TES-103 | hypothetical protein LOC25900 |
| 83 | −3.6268598 | C3orf63 | chromosome 3 open reading frame 63 |
| 84 | −3.6245164 | PDZRN3 | PDZ domain containing RING finger 3 |
| 85 | −3.6111722 | XDH | xanthine dehydrogenase |
| 86 | −3.5942736 | EDARADD | EDAR-associated death domain |
| 87 | −3.5276085 | FLJ45803 | FLJ45803 protein |
| 88 | −3.5155378 | ZNF471 | zinc finger protein 471 |
| 89 | −3.4746673 | CSTF2T | cleavage stimulation factor, 3' pre-RNA, subunit 2, 64 kDa, tau variant |
| 90 | −3.4209931 | TNRC15 | trinucleotide repeat containing 15 |
| 91 | −3.3787593 | KPNA5 | karyopherin alpha 5 (importin alpha 6) |
| 92 | −3.3680628 | KIF21A | kinesin family member 21A |
| 93 | −3.3452173 | PUS7L | pseudouridylate synthase 7 homolog (*S. cerevisiae*)-like |
| 94 | −3.3451301 | SARS | seryl-tRNA synthetase |
| 95 | −3.341299 | DPH1 | DPH1 homolog (*S. cerevisiae*) |
| 96 | −3.3357243 | CD200R1 | CD200 receptor 1 |
| 97 | −3.3063122 | UQCRQ | ubiquinol-cytochrome c reductase, complex III subunit VII, 9.5 kDa |
| 98 | −3.3019946 | PABPC3 | poly(A) binding protein, cytoplasmic 3 |
| 99 | −3.2695814 | RABGGTB | Rab geranylgeranyltransferase, beta subunit |
| 100 | −3.2559803 | UNC119 | unc-119 homolog (*C. elegans*) |
| 101 | −3.2545106 | TEF | thyrotrophic embryonic factor |
| 102 | −3.2226705 | NOV | nephroblastoma overexpressed gene |
| 103 | −3.2098851 | UCHL3 | ubiquitin carboxyl-terminal esterase L3 (ubiquitin thiolesterase) |
| 104 | −3.2023439 | ATG9A | ATG9 autophagy related 9 homolog A (*S. cerevisiae*) |
| 105 | −3.2014754 | RANGAP1 | Ran GTPase activating protein 1 |
| 106 | −3.1980978 | CALN1 | calneuron 1 |
| 107 | −3.1963827 | NARS | asparaginyl-tRNA synthetase |
| 108 | −3.1943166 | KRT14 | keratin 14 (epidermolysis bullosa simplex, Dowling-Meara, Koebner) |
| 109 | −3.148778 | C20orf160 | chromosome 20 open reading frame 160 |
| 110 | −3.1295196 | WDR24 | WD repeat domain 24 |
| 111 | −3.1291412 | HSPBAP1 | HSPBAP1 |
| 112 | −3.1111004 | RAB33A | RAB33A, member RAS oncogene family |
| 113 | −3.0745488 | PRDM7 | PR domain containing 7 |
| 114 | −3.0578356 | DIS3L2 | DIS3 mitotic control homolog (*S. cerevisiae*)-like 2 |
| 115 | −3.01931 | LOC648245 | hypothetical LOC648245 |
| 116 | −3.0145409 | CMTM2 | CKLF-like MARVEL transmembrane domain containing 2 |
| 117 | −2.9990908 | FLAD1 | FAD1 flavin adenine dinucleotide synthetase homolog (*S. cerevisiae*) |
| 118 | −2.9907691 | TNXB | tenascin XB |
| 119 | −2.9470716 | HEXA | hexosaminidase A (alpha polypeptide) |
| 120 | −2.9454804 | N6AMT1 | N-6 adenine-specific DNA methyltransferase 1 (putative) |
| 121 | −2.9378442 | UPRT | uracil phosphoribosyltransferase (FUR1) homolog (*S. cerevisiae*) |
| 122 | −2.9341038 | ACOX2 | acyl-Coenzyme A oxidase 2, branched chain |
| 123 | −2.9083204 | VARS | valyl-tRNA synthetase |
| 124 | −2.8881904 | CPAMD8 | C3 and PZP-like, alpha-2-macroglobulin domain containing 8 |
| 125 | −2.8843723 | MEA1 | male-enhanced antigen 1 |
| 126 | −2.8723149 | ASB7 | ankyrin repeat and SOCS box-containing 7 |
| 127 | −2.8477684 | FAT2 | FAT tumor suppressor homolog 2 (Drosophila) |
| 128 | −2.8369687 | RAPSN | receptor-associated protein of the synapse |
| 129 | −2.799245 | SPRYD5 | SPRY domain containing 5 |
| 130 | −2.7949389 | MLH3 | mutL homolog 3 (*E. coli*) |

TABLE I-continued

RNAi screening dataset and pathway analysis

| Gene No. | SSMD value | Gene Symbol | Gene name |
|---|---|---|---|
| 131 | −2.7901506 | FBXW7 | F-box and WD repeat domain containing 7 |
| 132 | −2.7874021 | SPSB2 | splA/ryanodine receptor domain and SOCS box containing 2 |
| 133 | −2.7854298 | AMPD1 | adenosine monophosphate deaminase 1 (isoform M) |
| 134 | −2.7834861 | MLLT3 | myeloid/lymphoid or mixed-lineage leukemia (trithorax homolog, *Drosophila*); translocated to, 3 |
| 135 | −2.7787695 | C10orf12 | chromosome 10 open reading frame 12 |
| 136 | −2.769805 | TSC22D4 | TSC22 domain family, member 4 |
| 137 | −2.7666121 | C14orf93 | chromosome 14 open reading frame 93 |
| 138 | −2.7611242 | CCNA1 | cyclin A1 |
| 139 | −2.7497171 | CXCL2 | chemokine (C-X-C motif) ligand 2 |
| 140 | −2.7460054 | PRF1 | perforin 1 (pore forming protein) |
| 141 | −2.7440268 | ACOX1 | acyl-Coenzyme A oxidase 1, palmitoyl |
| 142 | −2.729416 | CFC1 | cripto, FRL-1, cryptic family 1 |
| 143 | −2.7177655 | SC4MOL | sterol-C4-methyl oxidase-like |
| 144 | −2.7040988 | ACAD9 | acyl-Coenzyme A dehydrogenase family, member 9 |
| 145 | −2.6830011 | FAM57B | family with sequence similarity 57, member B |
| 146 | −2.6741981 | HINT1 | histidine triad nucleotide binding protein 1 |
| 147 | −2.6678936 | NDUFS5 | NADH dehydrogenase (ubiquinone) Fe-S protein 5, 15 kDa (NADH-coenzyme Q reductase) |
| 148 | −2.6593858 | TRPS1 | trichorhinophalangeal syndrome I |
| 149 | −2.6487549 | CHST14 | carbohydrate (N-acetylgalactosamine 4-0) sulfotransferase 14 |
| 150 | −2.6442317 | HCST | hematopoietic cell signal transducer |
| 151 | −2.6310474 | C1orf184 | chromosome 1 open reading frame 184 |
| 152 | −2.5969352 | COMMD3 | COMM domain containing 3 |
| 153 | −2.5801224 | B3GAT2 | beta-1,3-glucuronyltransferase 2 (glucuronosyltransferase S) |
| 154 | −2.5775984 | SLC41A2 | solute carrier family 41, member 2 |
| 155 | −2.5767866 | MAGEH1 | melanoma antigen family H, 1 |
| 156 | −2.5652802 | C12orf60 | chromosome 12 open reading frame 60 |
| 157 | −2.5613829 | IFNA8 | interferon, alpha 8 |
| 158 | −2.5543536 | SNTB1 | syntrophin, beta 1 (dystrophin-associated protein A1, 59 kDa, basic component 1) |
| 159 | −2.5511163 | YIPF4 | Yip1 domain family, member 4 |
| 160 | −2.5499357 | PREX1 | phosphatidylinositol 3,4,5-trisphosphate-dependent RAC exchanger 1 |
| 161 | −2.5371764 | ZNF232 | zinc finger protein 232 |
| 162 | −2.5299921 | CEACAM7 | carcinoembryonic antigen-related cell adhesion molecule 7 |
| 163 | −2.5247214 | SOX12 | SRY (sex determining region Y)-box 12 |
| 164 | −2.5241002 | PDPN | podoplanin |
| 165 | −2.5080828 | ENSA | endosulfine alpha |
| 166 | −2.4988284 | C19orf12 | chromosome 19 open reading frame 12 |
| 167 | −2.489459 | KRT33B | keratin 33B |
| 168 | −2.4867585 | OR4A47 | olfactory receptor, family 4, subfamily A, member 47 |
| 169 | −2.4673083 | DNHD1 | dynein heavy chain domain 1 |
| 170 | −2.4663961 | LPP | LIM domain containing preferred translocation partner in lipoma |
| 171 | −2.4256039 | MFAP3 | microfibrillar-associated protein 3 |
| 172 | −2.420265 | METTL6 | methyltransferase like 6 |
| 173 | −2.417579 | PFDN2 | prefoldin subunit 2 |
| 174 | −2.4109604 | KCNN3 | potassium intermediate/small conductance calcium-activated channel, subfamily N, member 3 |
| 175 | −2.4038566 | CCDC3 | coiled-coil domain containing 3 |
| 176 | −2.3822156 | ELP4 | elongation protein 4 homolog (*S. cerevisiae*) |
| 177 | −2.3745863 | NFIA | nuclear factor I/A |
| 178 | −2.3659721 | HPDL | 4-hydroxyphenylpyruvate dioxygenase-like |
| 179 | −2.3522936 | PIGQ | phosphatidylinositol glycan anchor biosynthesis, class Q |
| 180 | −2.3308218 | CFH | complement factor H |
| 181 | −2.3251913 | INDO | indoleamine-pyrrole 2,3 dioxygenase |
| 182 | −2.3097462 | GNG4 | guanine nucleotide binding protein (G protein), gamma 4 |
| 183 | −2.3090617 | SCGB2A2 | secretoglobin, family 2A, member 2 |
| 184 | −2.2962081 | ABCA13 | ATP-binding cassette, sub-family A (ABC1), member 13 |
| 185 | −2.2894951 | ATXN2 | ataxin 2 |
| 186 | −2.2783461 | AFF1 | AF4/FMR2 family, member 1 |
| 187 | −2.2686635 | FLRT1 | fibronectin leucine rich transmembrane protein 1 |
| 188 | −2.235555 | KIAA1012 | KIAA1012 |
| 189 | −2.2251917 | DKFZp761E198 | DKFZp761E198 protein |
| 190 | −2.2232003 | ACOT9 | acyl-CoA thioesterase 9 |
| 191 | −2.1987256 | ASAH1 | N-acylsphingosine amidohydrolase (acid ceramidase) 1 |

TABLE I-continued

RNAi screening dataset and pathway analysis

| Gene No. | SSMD value | Gene Symbol | Gene name |
|---|---|---|---|
| 192 | −2.1954145 | IFNA4 | interferon, alpha 4 |
| 193 | −2.1809081 | TFAP2D | transcription factor AP-2 delta (activating enhancer binding protein 2 delta) |
| 194 | −2.1700328 | RAE1 | RAE1 RNA export 1 homolog (S. pombe) |
| 195 | −2.1698369 | PROC | protein C (inactivator of coagulation factors Va and VIIIa) |
| 196 | −2.165263 | SNCG | synuclein, gamma (breast cancer-specific protein 1) |
| 197 | −2.1625038 | FAM150A | family with sequence similarity 150, member A |
| 198 | −2.1614844 | FAU | Finkel-Biskis-Reilly murine sarcoma virus (FBR-MuSV) ubiquitously expressed |
| 199 | −2.1580046 | SLC22A23 | solute carrier family 22, member 23 |
| 200 | −2.1574259 | POLDIP2 | polymerase (DNA-directed), delta interacting protein 2 |
| 201 | −2.1407089 | MOCS2 | molybdenum cofactor synthesis 2 |
| 202 | −2.1384918 | FAM83A | family with sequence similarity 83, member A |
| 203 | −2.1380471 | OR2J3 | olfactory receptor, family 2, subfamily J, member 3 |
| 204 | −2.1318114 | PLEK2 | pleckstrin 2 |
| 205 | −2.1206274 | PREPL | prolyl endopeptidase-like |
| 206 | −2.1123968 | UNC5B | unc-5 homolog B (*C. elegans*) |
| 207 | −2.1099896 | HTATIP2 | HIV-1 Tat interactive protein 2, 30 kDa |
| 208 | −2.0920994 | GAD2 | glutamate decarboxylase 2 (pancreatic islets and brain, 65 kDa) |
| 209 | −2.088495 | OR10J5 | olfactory receptor, family 10, subfamily J, member 5 |
| 210 | −2.0817465 | KLF14 | Kruppel-like factor 14 |
| 211 | −2.071829 | APOC3 | apolipoprotein C-III |
| 212 | −2.0667778 | LRFN5 | leucine rich repeat and fibronectin type III domain containing 5 |
| 213 | −2.0628905 | OR11H1 | olfactory receptor, family 11, subfamily H, member 1 |
| 214 | −2.0577797 | BCL9 | B-cell CLL/lymphoma 9 |
| 215 | −2.0576639 | ZNF30 | zinc finger protein 30 |
| 216 | −2.048178 | TMEM128 | transmembrane protein 128 |
| 217 | −2.0458274 | MAN1A1 | mannosidase, alpha, class 1A, member 1 |
| 218 | −2.0338681 | FAIM2 | Fas apoptotic inhibitory molecule 2 |
| 219 | −2.0237102 | PLEKHH3 | PLEKHH3 |
| 220 | −2.0171959 | PKD1L2 | polycystic kidney disease 1-like 2 |
| 221 | −2.0156979 | hCG_1790950 | hCG1790950 |
| 222 | −1.9936177 | C2CD2 | C2 calcium-dependent domain containing 2 |
| 223 | −1.9930307 | MTHFR | 5,10-methylenetetrahydrofolate reductase (NADPH) |
| 224 | −1.9794613 | C2orf15 | chromosome 2 open reading frame 15 |
| 225 | −1.9637576 | SIAH2 | seven in absentia homolog 2 (*Drosophila*) |
| 226 | −1.9450083 | SH2B1 | SH2B adaptor protein 1 |
| 227 | −1.9434181 | CHD6 | chromodomain helicase DNA binding protein 6 |
| 228 | −1.9420799 | FAM105B | family with sequence similarity 105, member B |
| 229 | −1.9401491 | PBRM1 | polybromo 1 |
| 230 | −1.9324534 | SLC18A1 | solute carrier family 18 (vesicular monoamine), member 1 |
| 231 | −1.9310065 | LOC646851 | hypothetical LOC646851 |
| 232 | −1.9242151 | TRAF2 | TNF receptor-associated factor 2 |
| 233 | −1.9232435 | TMEM77 | transmembrane protein 77 |
| 234 | −1.9212875 | CCL4 | chemokine (C-C motif) ligand 4 |
| 235 | −1.9144899 | SIX6 | SIX homeobox 6 |
| 236 | −1.9106753 | GSTM3 | glutathione S-transferase M3 (brain) |
| 237 | −1.8894099 | FAM81A | family with sequence similarity 81, member A |
| 238 | −1.8811314 | LY6G6E | lymphocyte antigen 6 complex, locus G6E |
| 239 | −1.8787867 | TMEFF2 | transmembrane protein with EGF-like and two follistatin-like domains 2 |
| 240 | −1.8753798 | ZNF285A | zinc finger protein 285A |
| 241 | −1.8753392 | DHX35 | DHX35 |
| 242 | −1.8751799 | DCI | dodecenoyl-Coenzyme A delta isomerase (3,2 trans-enoyl-Coenzyme A isomerase) |
| 243 | −1.8446807 | CEBPE | CCAAT/enhancer binding protein (C/EBP), epsilon |
| 244 | −1.8426186 | USP4 | ubiquitin specific peptidase 4 (proto-oncogene) |
| 245 | −1.8391966 | EDAR | ectodysplasin A receptor |
| 246 | −1.8344474 | DUOXA2 | dual oxidase maturation factor 2 |
| 247 | −1.8318214 | C17orf68 | C17orf68 |
| 248 | −1.8290784 | ATXN1 | ataxin 1 |
| 249 | −1.8283931 | KRTAP1-1 | keratin associated protein 1-1 |
| 250 | −1.8239981 | DKFZP434B0335 | DKFZP434B0335 protein |
| 251 | −1.8020112 | MICAL2 | microtubule associated monoxygenase, calponin and LIM domain containing 2 |
| 252 | −1.7924913 | KPNA3 | karyopherin alpha 3 (importin alpha 4) |
| 253 | −1.7872999 | SRM | spermidine synthase |
| 254 | −1.7736672 | CCDC74B | coiled-coil domain containing 74B |
| 255 | −1.7731942 | CPSF4 | cleavage and polyadenylation specific factor 4, 30 kDa |
| 256 | −1.7710113 | CCDC70 | coiled-coil domain containing 70 |

TABLE I-continued

RNAi screening dataset and pathway analysis

| Gene No. | SSMD value | Gene Symbol | Gene name |
|---|---|---|---|
| 257 | −1.7708434 | LDB3 | LIM domain binding 3 |
| 258 | −1.7701503 | SBNO2 | strawberry notch homolog 2 (*Drosophila*) |
| 259 | −1.7686092 | E2F3 | E2F transcription factor 3 |
| 260 | −1.7648984 | SOCS6 | suppressor of cytokine signaling 6 |
| 261 | −1.7622297 | ZNF563 | zinc finger protein 563 |
| 262 | −1.761026 | PEBP1 | phosphatidylethanolamine binding protein 1 |
| 263 | −1.7565446 | DENND2A | DENN/MADD domain containing 2A |
| 264 | −1.7542676 | TRIM16L | tripartite motif-containing 16-like |
| 265 | −1.75106 | NNMT | nicotinamide N-methyltransferase |
| 266 | −1.7498752 | FAM58B | family with sequence similarity 58, member B |
| 267 | −1.7466437 | UGT2B28 | UDP glucuronosyltransferase 2 family, polypeptide B28 |
| 268 | −1.7455847 | KCTD2 | potassium channel tetramerisation domain containing 2 |
| 269 | −1.7437943 | PRRX1 | paired related homeobox 1 |
| 270 | −1.741886 | UBC | ubiquitin C |
| 271 | −1.7358353 | NKX2-2 | NK2 homeobox 2 |
| 272 | −1.7284565 | LOC146325 | similar to hypothetical protein F1113841 |
| 273 | −1.7186891 | PRPF40B | PRP40 pre-mRNA processing factor 40 homolog B (*S. cerevisiae*) |
| 274 | −1.7128125 | IFNG | interferon, gamma |
| 275 | −1.7113483 | STAMM | StAR-related lipid transfer (START) domain containing 6 |
| 276 | −1.6947777 | KIAA1407 | KIAA1407 |
| 277 | −1.6905819 | TIMM50 | translocase of inner mitochondrial membrane 50 homolog (*S. cerevisiae*) |
| 278 | −1.6896399 | KCNJ16 | potassium inwardly-rectifying channel, subfamily J, member 16 |
| 279 | −1.6880606 | RBM17 | RNA binding motif protein 17 |
| 280 | −1.6843206 | CCND2 | cyclin D2 |
| 281 | −1.6823255 | C10orf11 | chromosome 10 open reading frame 11 |
| 282 | −1.6733114 | FLJ45717 | FLJ45717 protein |
| 283 | −1.6723514 | CDC42EP4 | CDC42 effector protein (Rho GTPase binding) 4 |
| 284 | −1.667956 | NIT1 | nitrilase 1 |
| 285 | −1.6667056 | ACAD8 | acyl-Coenzyme A dehydrogenase family, member 8 |
| 286 | −1.6566013 | SLCO4A1 | solute carrier organic anion transporter family, member 4A1 |
| 287 | −1.6353608 | TOMM20 | TOMM20 |
| 288 | −1.6334009 | NHEDC2 | Na+/H+ exchanger domain containing 2 |
| 289 | −1.6332066 | FOXI2 | forkhead box I2 |
| 290 | −1.6311566 | DVL2 | dishevelled, dsh homolog 2 (*Drosophila*) |
| 291 | −1.6024628 | SKIV2L2 | superkiller viralicidic activity 2-like 2 (*S. cerevisiae*) |
| 292 | −1.599534 | DUT | deoxyuridine triphosphatase |
| 293 | −1.5980335 | PIN1 | protein (peptidylprolyl cis/trans isomerase) NIMA-interacting 1 |
| 294 | −1.5888359 | RAB11FIP1 | RAB11 family interacting protein 1 (class I) |
| 295 | −1.58562 | C20orf191 | chromosome 20 open reading frame 191 |
| 296 | −1.5705278 | CRB1 | crumbs homolog 1 (*Drosophila*) |
| 297 | −1.5703923 | HERC5 | hect domain and RLD 5 |
| 298 | −1.5697466 | HOXD12 | homeobox D12 |
| 299 | −1.5671741 | OGG1 | 8-oxoguanine DNA glycosylase |
| 300 | −1.5599221 | LOC283804 | similar to a disintegrin and metallopeptidase domain 6 |
| 301 | −1.5516378 | NUDT15 | nudix (nucleoside diphosphate linked moiety X)-type motif 15 |
| 302 | −1.539982 | C6orf128 | chromosome 6 open reading frame 128 |
| 303 | −1.5388222 | BTN3A3 | butyrophilin, subfamily 3, member A3 |
| 304 | −1.531419 | ADAMTS6 | ADAM metallopeptidase with thrombospondin type 1 motif, 6 |
| 305 | −1.5308875 | UBE2U | ubiquitin-conjugating enzyme E2U (putative) |
| 306 | −1.528943 | C20orf174 | chromosome 20 open reading frame 174 |
| 307 | −1.5206189 | HTR3C | 5-hydroxytryptamine (serotonin) receptor 3, family member C |
| 308 | −1.5141922 | IFNE1 | interferon epsilon 1 |
| 309 | −1.5135672 | SHROOM2 | shroom family member 2 |
| 310 | −1.5131067 | LOC158345 | similar to ribosomal protein L4 |
| 311 | −1.5110219 | STRN3 | striatin, calmodulin binding protein 3 |
| 312 | −1.5093142 | LHX9 | LIM homeobox 9 |
| 313 | −1.5085966 | LIG3 | ligase III, DNA, ATP-dependent |
| 314 | −1.5004124 | ZNF688 | zinc finger protein 688 |
| 315 | −1.4907284 | KRT2 | keratin 2 (epidermal ichthyosis bullosa of Siemens) |
| 316 | −1.4902236 | GJB6 | gap junction protein, beta 6, 30 kDa |
| 317 | −1.4847171 | SEMA3F | sema domain, immunoglobulin domain (Ig), short basic domain, secreted, (semaphorin) 3F |
| 318 | −1.4823505 | NDUFA3 | NADH dehydrogenase (ubiquinone) 1 alpha subcomplex, 3, 9 kDa |

TABLE I-continued

RNAi screening dataset and pathway analysis

| Gene No. | SSMD value | Gene Symbol | Gene name |
|---|---|---|---|
| 319 | −1.4820184 | CCNL1 | cyclin L1 |
| 320 | −1.4817085 | VPS4A | vacuolar protein sorting 4 homolog A (S. cerevisiae) |
| 321 | −1.4785172 | THRA | thyroid hormone receptor, alpha (erythroblastic leukemia viral (v-erb-a) oncogene homolog, avian) |
| 322 | −1.4768031 | LOC729747 | similar to zinc finger protein 709 |
| 323 | −1.4694163 | RNPEPL1 | arginyl aminopeptidase (aminopeptidase B)-like 1 |
| 324 | −1.4648548 | SRCRB4D | scavenger receptor cysteine rich domain containing, group B (4 domains) |
| 325 | −1.4594768 | ZNF583 | zinc finger protein 583 |
| 326 | −1.4579192 | ABCA10 | ATP-binding cassette, sub-family A (ABC1), member 10 |
| 327 | −1.4574003 | RUSC1 | RUN and SH3 domain containing 1 |
| 328 | −1.4556341 | PUS10 | pseudouridylate synthase 10 |
| 329 | −1.454968 | ACTRT1 | actin-related protein T1 |
| 330 | −1.4534222 | SLC20A1 | solute carrier family 20 (phosphate transporter), member 1 |
| 331 | −1.4528362 | APCDD1 | adenomatosis polyposis coli down-regulated 1 |
| 332 | −1.4517923 | OR5T1 | olfactory receptor, family 5, subfamily T, member 1 |
| 333 | −1.4513226 | TNFSF4 | tumor necrosis factor (ligand) superfamily, member 4 (tax-transcriptionally activated glycoprotein 1, 34 kDa) |
| 334 | −1.4507166 | FAM40B | family with sequence similarity 40, member B |
| 335 | −1.4507084 | SOSTDC1 | sclerostin domain containing 1 |
| 336 | −1.4479293 | SIN3B | SIN3 homolog B, transcription regulator (yeast) |
| 337 | −1.4448519 | NAE1 | NEDD8 activating enzyme E1 subunit 1 |
| 338 | −1.4444931 | ATP6V0A2 | ATPase, H+ transporting, lysosomal V0 subunit a2 |
| 339 | −1.4389504 | OR52N1 | olfactory receptor, family 52, subfamily N, member 1 |
| 340 | −1.4379584 | KRTAP1-1 | keratin associated protein 1-1 |
| 341 | −1.4357455 | CACNB4 | calcium channel, voltage-dependent, beta 4 subunit |
| 342 | −1.4344684 | TMEM166 | transmembrane protein 166 |
| 343 | −1.4343287 | SEPP1 | selenoprotein P, plasma, 1 |
| 344 | −1.4247328 | CPNE8 | copine VIII |
| 345 | −1.4217619 | LYPLA3 | lysophospholipase 3 (lysosomal phospholipase A2) |
| 346 | −1.4199602 | SPOCD1 | SPOC domain containing 1 |
| 347 | −1.4105046 | C1orf26 | chromosome 1 open reading frame 26 |
| 348 | −1.4045891 | NELL1 | NEL-like 1 (chicken) |
| 349 | −1.3910379 | NPY6R | neuropeptide Y receptor Y6 (pseudogene) |
| 350 | −1.3909844 | NFKBIL2 | nuclear factor of kappa light polypeptide gene enhancer in B-cells inhibitor-like 2 |
| 351 | −1.3862547 | RAB11FIP2 | RAB11 family interacting protein 2 (class I) |
| 352 | −1.3838073 | C19orf53 | chromosome 19 open reading frame 53 |
| 353 | −1.3809126 | PCK2 | phosphoenolpyruvate carboxykinase 2 (mitochondrial) |
| 354 | −1.3798572 | GLI2 | GLI-Kruppel family member GLI2 |
| 355 | −1.3767028 | PRSS2 | protease, serine, 2 (trypsin 2) |
| 356 | −1.3755838 | LOC145814 | hypothetical protein LOC145814 |
| 357 | −1.3755072 | NPPA | natriuretic peptide precursor A |
| 358 | −1.3750957 | NMT2 | N-myristoyltransferase 2 |
| 359 | −1.3728588 | KCTD15 | KCTD15 |
| 360 | −1.3713774 | ASNS | asparagine synthetase |
| 361 | −1.3695476 | PKD1 | polycystic kidney disease 1 (autosomal dominant) |
| 362 | −1.3615194 | SPATA1 | spermatogenesis associated 1 |
| 363 | −1.3507685 | DUX1 | double homeobox, 1 |
| 364 | −1.3491583 | LOC283116 | similar to Tripartite motif protein 49 (RING finger protein 18) (Testis-specific ring-finger protein) |
| 365 | −1.3463833 | SLC41A2 | solute carrier family 41, member 2 |
| 366 | −1.3404022 | OR51M1 | olfactory receptor, family 51, subfamily M, member 1 |
| 367 | −1.3396235 | PLP1 | proteolipid protein 1 (Pelizaeus-Merzbacher disease, spastic paraplegia 2, uncomplicated) |
| 368 | −1.3388042 | RHBDF1 | rhomboid 5 homolog 1 (Drosophila) |
| 369 | −1.3330637 | MIS12 | MIS12, MIND kinetochore complex component, homolog (yeast) |
| 370 | −1.3328425 | OR4M2 | olfactory receptor, family 4, subfamily M, member 2 |
| 371 | −1.3283486 | NDUFA6 | NADH dehydrogenase (ubiquinone) 1 alpha subcomplex, 6, 14 kDa |
| 372 | −1.3280268 | ACRC | acidic repeat containing |
| 373 | −1.3251516 | MAD2L1 | MAD2 mitotic arrest deficient-like 1 (yeast) |
| 374 | −1.3244852 | FAM134A | family with sequence similarity 134, member A |
| 375 | −1.3240723 | CWF19L2 | CWF19-like 2, cell cycle control (S. pombe) |
| 376 | −1.3226761 | LYZL1 | lysozyme-like 1 |
| 377 | −1.3201714 | LRP6 | low density lipoprotein receptor-related protein 6 |
| 378 | −1.3194011 | MS4A5 | membrane-spanning 4-domains, subfamily A, member 5 |
| 379 | −1.3172909 | ZNF433 | zinc finger protein 433 |
| 380 | −1.3132902 | SERP1 | stress-associated endoplasmic reticulum protein 1 |
| 381 | −1.3055891 | METRN | meteorin, glial cell differentiation regulator |

Figure 1C:
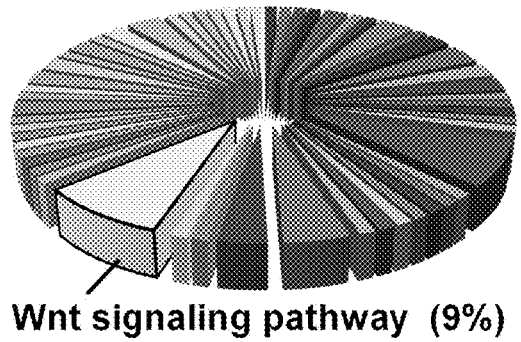
Figure 2A:
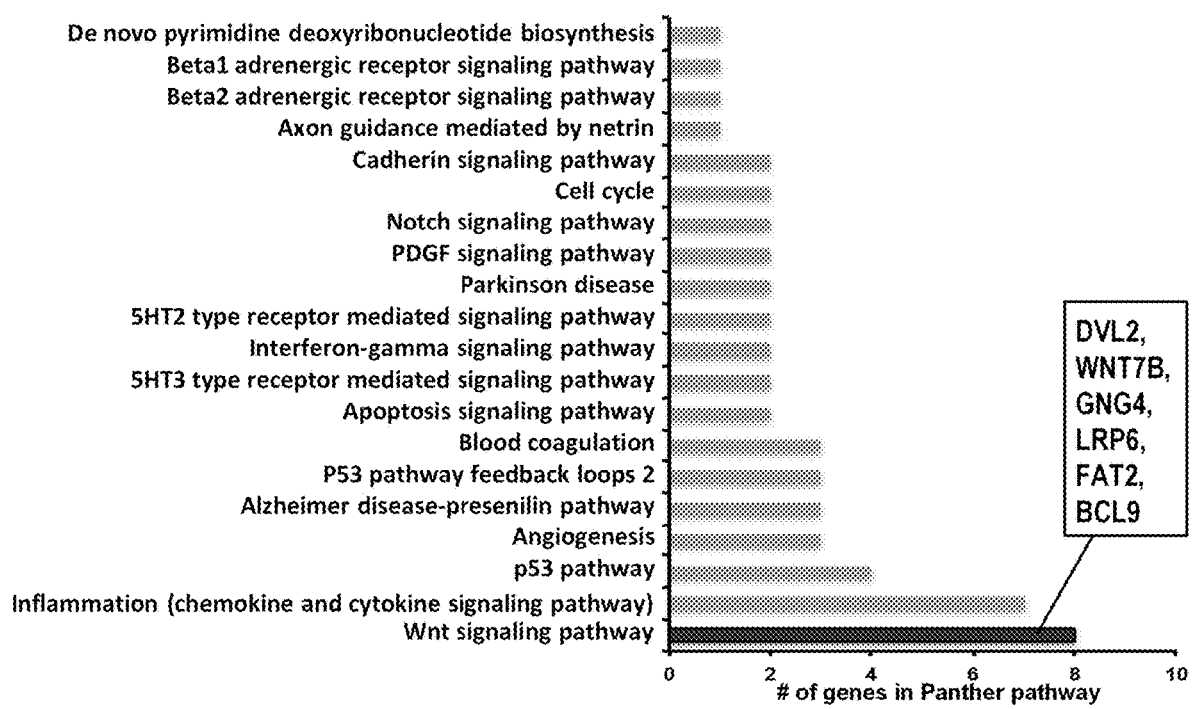
FIG. 2A-2C shows bioinformatics analysis of genome-wide RNAi screening data. The PANTHER pathways bioinformatics tool was used to group genes from the hit list into cellular pathways from a curated database (FIG. 2A). Eighty nine of 381 genes were placed into 56 cellular pathways, and the top 20 pathways are shown. The DAVID bioinformatics resource provided a comprehensive set of functional annotation tools to understand biological meaning behind a large list of genes (FIG. 2B). The DAVID functional annotation clustering tool was used to group genes in the hit list into sets of proteins that share common annotations. The top 20 annotation clusters are shown and ranked based on enrichment score. The RNAi screening hit list was also subjected to STRING bioinformatics (FIG. 2C), a search tool for retrieval of interacting genes/proteins from a database of known and predicted protein interactions and networks. Cytoscape data visualization software was used to display STRING results. Proteins without interactions and UBC node were removed and not shown in radial graph. Wnt signaling genes/proteins and interactions identified by these bioinformatics tools are provided in the lower left (i.e., WWOX, NKD2, DVL2, FRAT2, LRP6, and WNT7B). Other numbered genes and proteins include 1: GLI2, 2:MT3, 3: IFNG, 4: CCL4, 5: CXCL2, 6: CCL5, 7: PRF1, 8: RAE1, 9: small nuclear ribonucleoprotein Sm D3 (SNRPD3), 10: PRPF40B, 11: NCBP1, 12: KPNA3, 13: RANGAP1, 14: IGF1, 15: NPPA, 16: CST3, 17: ATXN1, 18: VDAC1, 19: TRAF2, 20: SIAH2, 21: AFF1, 22: MLLT3, 23: VAV1, 24: LPP, 25: NARS, 26: SARS, 27: AHNAK, 28: FKBP2, 29: TOMM20, 30: CCNG1, 31: RFC2, 32: UBE2C, 33: CCNA1, 34: DUT, 35: MAD2L1, 36: NAE1, 37: RABG-GTB, 38: NDUFB5, 39: NDUFA2, 40: NDUFA3, 41: NDUFA6, 42: TIMM8B, 43: UQCRQ, 44: NDUFS5, 45: HINT1, 46: FAU, 47: PIN1, 48: E2F3, 49: CCND2, 50: NKX2-2, A1: IDO1 (or INDO), A2: IFNA8, A3: LAMP1, A4: VPS4A, A5: STAM, A6: WDR24, A7: KPNA5, A8: C10orf11, B1: MIS12, B2: PIGQ, B3: PDGFB, B4: NOV, B5: HEYL, C1: ATXN2, C2: BAT3, C3: SC4MOL, C4: RBM17, C5: USP4, C6: EDAR, C7: EDARADD, C8: TNFSF4, C9: C20orf191, D1: HCST, D2: TRGC1 (T Cell Receptor Gamma Constant 1), D3: TRAPPC8 (trafficking protein particle complex 8), D4: TECPR1 (tectonin beta-propeller repeat containing 1), D5: CCT6B, D6: ASNS, D7: GAD2, D8: VARS, E1: HSP90AA1, E2: NLRP4, E3: TIMM50, E4: LIG3, E5: OGG1, E6: THRA, E7: CPSF4, E8: GJB6, E9: CSTF2T, E10: RAD9B (RAD9 checkpoint clamp component B), F1: PFDN2, F2: CWF19L2, F3: ANKRD32, F4: GSTA3, F5: GSTM3, G1: SPOCD1, G2: FBXW7, H1: NNMT, H2: PROC, H3: MTHFR, I1: SH2B1, I2: KCTD15, I3: FAIM2, J1: OR10J5, J2: OR51M1, J3: OR5D16, J4: OR10G8, J5: OR5T1, and J6: OR52N1.

To extract information regarding critical processes in infection, we performed bioinformatics analysis on the hit list. Final hits were functionally clustered using the PANTHER pathway classification system (see, e.g., Nikolsky Y et al., "Protein networks and pathway analysis: preface," *Methods Mol. Biol.* 2009; 563:v-vii). Using this method, 89 of the total 381 genes were grouped into 56 separate pathways (Table II), and the Wnt signaling pathway was the most represented pathway with 9% (8 of 89) of the genes (FIG. 1C and FIG. 2A).

TABLE II

PANTHER pathway analysis

| No. | PANTHER pathway | No. of genes in pathway[a] | % of total hits (360) analyzed by PANTHER | % of total genes (89) in pathways[b] |
|---|---|---|---|---|
| 1 | Wnt signaling pathway (P00057) | 8 | 2.20% | 9.00% |
| 2 | Inflammation mediated by chemokine and cytokine signaling pathway (P00031) | 7 | 1.90% | 7.90% |
| 3 | p53 pathway (P00059) | 4 | 1.10% | 4.50% |
| 4 | Angiogenesis (P00005) | 3 | 0.80% | 3.40% |
| 5 | Alzheimer disease-presenilin pathway (P00004) | 3 | 0.80% | 3.40% |
| 6 | p53 pathway feedback loops 2 (P04398) | 3 | 0.80% | 3.40% |
| 7 | Blood coagulation (P00011) | 3 | 0.80% | 3.40% |
| 8 | Apoptosis signaling pathway (P00006) | 2 | 0.60% | 2.20% |
| 9 | 5HT3 type receptor mediated signaling pathway (P04375) | 2 | 0.60% | 2.20% |
| 10 | Interferon-gamma signaling pathway (P00035) | 2 | 0.60% | 2.20% |
| 11 | 5HT2 type receptor mediated signaling pathway (P04374) | 2 | 0.60% | 2.20% |
| 12 | Parkinson disease (P00049) | 2 | 0.60% | 2.20% |
| 13 | PDGF signaling pathway (P00047) | 2 | 0.60% | 2.20% |
| 14 | Notch signaling pathway (P00045) | 2 | 0.60% | 2.20% |
| 15 | Cell cycle (P00013) | 2 | 0.60% | 2.20% |
| 16 | Cadherin signaling pathway (P00012) | 2 | 0.60% | 2.20% |
| 17 | Axon guidance mediated by netrin (P00009) | 1 | 0.30% | 1.10% |
| 18 | Beta2 adrenergic receptor signaling pathway (P04378) | 1 | 0.30% | 1.10% |
| 19 | Beta1 adrenergic receptor signaling pathway (P04377) | 1 | 0.30% | 1.10% |
| 20 | De novo pyrimidine deoxyribonucleotide biosynthesis (P02739) | 1 | 0.30% | 1.10% |
| 21 | Ionotropic glutamate receptor pathway (P00037) | 1 | 0.30% | 1.10% |
| 22 | 5HT4 type receptor mediated signaling pathway (P04376) | 1 | 0.30% | 1.10% |
| 23 | Purine metabolism (P02769) | 1 | 0.30% | 1.10% |
| 24 | Integrin signaling pathway (P00034) | 1 | 0.30% | 1.10% |
| 25 | 5HT1 type receptor mediated signaling pathway (P04373) | 1 | 0.30% | 1.10% |
| 26 | Insulin/IGF pathway-protein kinase B signaling cascade (P00033) | 1 | 0.30% | 1.10% |
| 27 | Adrenaline and noradrenaline biosynthesis (P00001) | 1 | 0.30% | 1.10% |
| 28 | Insulin/IGF pathway-mitogen activated protein kinase kinase/MAP kinase cascade (P00032) | 1 | 0.30% | 1.10% |
| 29 | Asparagine and aspartate biosynthesis (P02730) | 1 | 0.30% | 1.10% |
| 30 | Ubiquitin proteasome pathway (P00060) | 1 | 0.30% | 1.10% |
| 31 | Synaptic vesicle trafficking (P05734) | 1 | 0.30% | 1.10% |
| 32 | GABA-B receptor II signaling (P05731) | 1 | 0.30% | 1.10% |
| 33 | Huntington disease (P00029) | 1 | 0.30% | 1.10% |
| 34 | Endogenous cannabinoid signaling (P05730) | 1 | 0.30% | 1.10% |
| 35 | Heterotrimeric G-protein signaling pathway-rod outer segment phototransduction (P00028) | 1 | 0.30% | 1.10% |
| 36 | Heterotrimeric G-protein signaling pathway-Gq alpha and Go alpha mediated pathway (P00027) | 1 | 0.30% | 1.10% |
| 37 | Heterotrimeric G-protein signaling pathway-Gi alpha and Gs alpha mediated pathway (P00026) | 1 | 0.30% | 1.10% |
| 38 | Hedgehog signaling pathway (P00025) | 1 | 0.30% | 1.10% |
| 39 | Vasopressin synthesis (P04395) | 1 | 0.30% | 1.10% |
| 40 | Thyrotropin-releasing hormone receptor signaling pathway (P04394) | 1 | 0.30% | 1.10% |
| 41 | Adenine and hypoxanthine salvage pathway (P02723) | 1 | 0.30% | 1.10% |
| 42 | T cell activation (P00053) | 1 | 0.30% | 1.10% |
| 43 | FGF signaling pathway (P00021) | 1 | 0.30% | 1.10% |
| 44 | Oxytocin receptor mediated signaling pathway (P04391) | 1 | 0.30% | 1.10% |

TABLE II-continued

PANTHER pathway analysis

| No. | PANTHER pathway | No. of genes in pathway[a] | % of total hits (360) analyzed by PANTHER | % of total genes (89) in pathways[b] |
|---|---|---|---|---|
| 45 | EGF receptor signaling pathway (P00018) | 1 | 0.30% | 1.10% |
| 46 | DNA replication (P00017) | 1 | 0.30% | 1.10% |
| 47 | P13 kinase pathway (P00048) | 1 | 0.30% | 1.10% |
| 48 | Heme biosynthesis (P02746) | 1 | 0.30% | 1.10% |
| 49 | Gamma-aminobutyric acid synthesis (P04384) | 1 | 0.30% | 1.10% |
| 50 | Dopamine receptor mediated signaling pathway (P05912) | 1 | 0.30% | 1.10% |
| 51 | Salvage pyrimidine ribonucleotides (P02775) | 1 | 0.30% | 1.10% |
| 52 | B cell activation (P00010) | 1 | 0.30% | 1.10% |
| 53 | Angiotensin II-stimulated signaling through G proteins and beta-arrestin (P05911) | 1 | 0.30% | 1.10% |
| 54 | Cortocotropin releasing factor receptor signaling pathway (P04380) | 1 | 0.30% | 1.10% |
| 55 | Flavin biosynthesis (P02741) | 1 | 0.30% | 1.10% |
| 56 | Gonadotropin releasing hormone receptor pathway (P06664) | 1 | 0.30% | 1.10% |

[a] represents values shown in FIG. 2A
[b] represents values shown in FIG. 1C

Figure 2B:
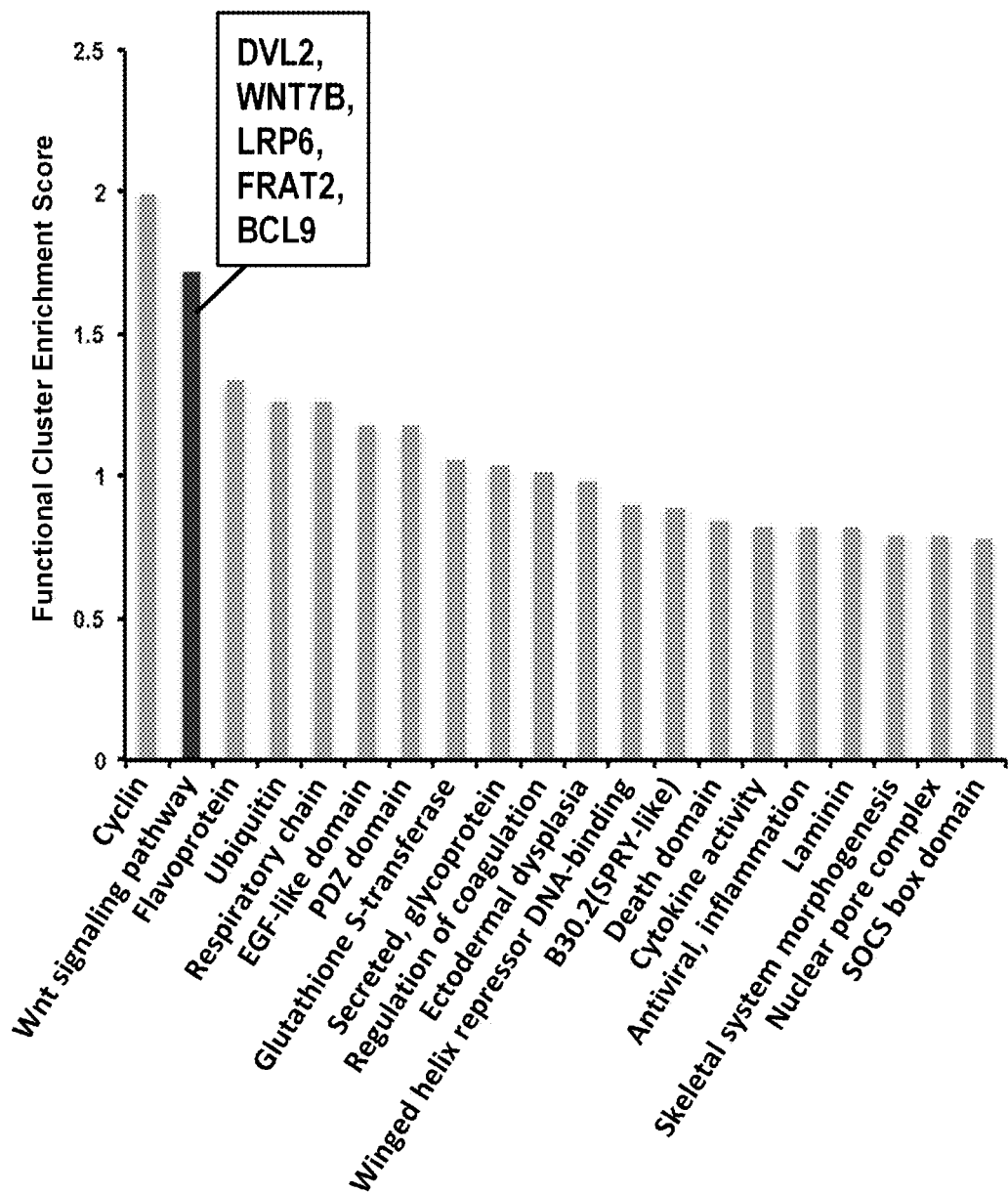

A second bioinformatics analysis was performed using DAVID, a public database that assigns hit lists to 'functional annotation clusters' or sets of proteins that share common annotations (see, e.g., Huang da W et al., "Systematic and integrative analysis of large gene lists using DAVID bioinformatics resources," Nat. Protoc. 2009; 4(1):44-57). The top 20 annotation clusters are shown in Tables IIIA-IIIT and FIG. 2B. Again, the Wnt pathway was amongst the most represented pathways in the hit list with the second best enrichment score.

TABLE IIIA

Annotation Cluster 1 (Enrichment Score: 1.998)

| Term | Count | % | P value | Genes |
|---|---|---|---|---|
| IPR006671: cyclin, N-term. | 5 | 1.397 | 0.00364 | CCND2, CCNL1, FAM58B, CCNA1, CCNG1 |
| IPR006670: cyclin | 5 | 1.397 | 0.00732 | CCND2, CCNL1, FAM58B, CCNA1, CCNG1 |
| SM00385: cyclin | 5 | 1.397 | 0.00845 | CCND2, CCNL1, FAM58B, CCNA1, CCNG1 |
| cyclin | 5 | 1.397 | 0.0131 | CCND2, CCNL1, FAM58B, CCNA1, CCNG1 |

TABLE IIIA-continued

Annotation Cluster 1 (Enrichment Score: 1.998)

| Term | Count | % | P value | Genes |
|---|---|---|---|---|
| IPR013763: cyclin-related | 4 | 1.117 | 0.0345 | CCND2, FAM58B, CCNA1, CCNG1 |

TABLE IIIB

Annotation Cluster 2 (Enrichment Score: 1.718)

| Term | Count | % | P value | Genes |
|---|---|---|---|---|
| Wnt signaling pathway | 9 | 2.514 | 0.00183 | DVL2, WNT7B, NKD2, SOSTDC1, LRP6, FRAT2, TLE1, WWOX, BCL9 |
| GO:0016055~ Wnt receptor signaling pathway | 8 | 2.235 | 0.0146 | DVL2, WNT7B, NKD2, SOSTDC1, LRP6, FRAT2, TLE1, BCL9 |
| hsa04310: Wnt signaling pathway | 6 | 1.676 | 0.261 | DVL2, WNT7B, NKD2, CCND2, LRP6, FRAT2 |

TABLE IIIC

Annotation Cluster 3 (Enrichment Score: 1.334)

| Term | Count | % | P value | Genes |
|---|---|---|---|---|
| FAD | 9 | 2.514 | 0.00119 | ACOX2, XDH, ACOX1, MTHFR, MICAL2, ACAD8, FLAD1, ACAD9, NQO2 |
| IPR013786: acyl-CoA dehydrogenase/oxidase, N-term. | 4 | 1.117 | 0.00224 | ACOX2, ACOX1, ACAD8, ACAD9 |
| GO:0003995~ acyl-CoA dehydrogenase activity | 4 | 1.117 | 0.00261 | ACOX2, ACOX1, ACAD8, ACAD9 |
| IPR013764: acyl-CoA oxidase/ dehydrogenase, type1/2, C-term. | 4 | 1.117 | 0.00276 | ACOX2, ACOX1, ACAD8, ACAD9 |
| IPR006091: acyl-CoA oxidase/ dehydrogenase, central region | 4 | 1.117 | 0.00276 | ACOX2, ACOX1, ACAD8, ACAD9 |
| Flavoprotein | 8 | 2.235 | 0.00354 | ACOX2, XDH, ACOX1, MTHFR, MICAL2, ACAD8, ACAD9, NQO2 |
| GO:0050660~ FAD binding | 5 | 1.397 | 0.0482 | ACOX2, XDH, ACOX1, ACAD8, ACAD9 |

TABLE IIIC-continued

Annotation Cluster 3 (Enrichment Score: 1.334)

| Term | Count | % | P value | Genes |
|---|---|---|---|---|
| GO:0048037~ cofactor binding | 10 | 2.793 | 0.0489 | ACOX2, XDH, ACOX1, GAD2, NELL1, ASNS, ACAD8, ACAD9, WWOX, NQO2 |
| GO:0050662~ coenzyme binding | 8 | 2.235 | 0.0586 | ACOX2, XDH, ACOX1, NELL1, ACAD8, ACAD9, WWOX, NQO2 |
| binding site: FAD | 3 | 0.838 | 0.0613 | XDH, ACOX1, NQO2 |
| nucleotide phosphate-binding region: FAD | 4 | 1.117 | 0.102 | XDH, MICAL2, ACAD8, NQO2 |
| GO:0055114~ oxidation reduction | 18 | 5.028 | 0.113 | XDH, ACOX2, ACOX1, NDUFA2, NDUFB5, NDUFA3, HTATIP2, MICAL2, NELL1, NDUFA6, UQCRQ, SC4MOL, NDUFS5, MTHFR, ACAD8, ACAD9, WWOX, NQO2 |
| GO:0046395~ carboxylic acid catabolic process | 5 | 1.397 | 0.167 | ACOX2, ACOX1, GAD2, ACAD8, DCI |
| GO:0016054~ organic acid catabolic process | 5 | 1.397 | 0.167 | ACOX2, ACOX1, GAD2, ACAD8, DCI |
| oxidoreductase | 14 | 3.911 | 0.231 | XDH, ACOX2, ACOX1, NDUFA2, NDUFB5, HTATIP2, NDUFA3, NDUFA6, SC4MOL, MTHFR, ACAD8, ACAD9, WWOX, NQO2 |
| GO:0005777~ peroxisome | 4 | 1.117 | 0.310 | ACOX2, XDH, ACOX1, MPV17 |
| GO:0042579~ microbody | 4 | 1.117 | 0.310 | ACOX2, XDH, ACOX1, MPV17 |
| GO:0009055~ electron carrier activity | 6 | 1.676 | 0.413 | ACOX2, XDH, ACOX1, ACAD8, ACAD9, NQO2 |
| peroxisome | 3 | 0.838 | 0.492 | ACOX2, XDH, ACOX1 |
| active site: proton acceptor | 9 | 2.514 | 0.921 | B3GAT2, XDH, ACOX1, HTATIP2, NIT1, SULT1B1, ACAD8, ACAD9, WWOX |

TABLE IIID

Annotation Cluster 4 (Enrichment Score: 1.265)

| Term | Count | % | P value | Genes |
|---|---|---|---|---|
| IPRO19954: ubiquitin conserved site | 4 | 1.117 | 0.0277 | UBC, UBL4B, FAU, BAT3 |
| IPR000626: ubiquitin | 4 | 1.117 | 0.0595 | UBC, UBL4B, FAU, BAT3 |
| SM00213: UBQ | 4 | 1.117 | 0.0659 | UBC, UBL4B, FAU, BAT3 |
| IPR019955: ubiquitin supergroup | 4 | 1.117 | 0.0797 | UBC, UBL4B, FAU, BAT3 |

TABLE IIIE

Annotation Cluster 5 (Enrichment Score: 1.264)

| Term | Count | % | P value | Genes |
|---|---|---|---|---|
| GO:0030964~ NADH dehydrogenase complex | 5 | 1.397 | 0.00798 | NDUFS5, NDUFB5, NDUFA2, NDUFA3, NDUFA6 |
| GO:0005747~ mitochondrial respiratory chain complex I | 5 | 1.397 | 0.00798 | NDUFS5, NDUFB5, NDUFA2, NDUFA3, NDUFA6 |
| GO:0045271~ respiratory chain complex I | 5 | 1.397 | 0.00798 | NDUFS5, NDUFB5, NDUFA2, NDUFA3, NDUFA6 |
| GO:0006120~ mitochondrial electron transport, NADH to ubiquinone | 5 | 1.397 | 0.00853 | NDUFS5, NDUFB5, NDUFA2, NDUFA3, NDUFA6 |
| GO:0003954~ NADH dehydrogenase activity | 5 | 1.397 | 0.00882 | NDUFS5, NDUFB5, NDUFA2, NDUFA3, NDUFA6 |
| GO:0008137~ NADH dehydrogenase (ubiquinone) activity | 5 | 1.397 | 0.00882 | NDUFS5, NDUFB5, NDUFA2, NDUFA3, NDUFA6 |
| GO:0050136~ NADH dehydrogenase (quinone) activity | 5 | 1.397 | 0.00882 | NDUFS5, NDUFB5, NDUFA2, NDUFA3, NDUFA6 |
| mitochondrion inner membrane | 10 | 2.793 | 0.00934 | NDUFS5, NDUFB5, NDUFA2, MRS2, NDUFA3, NDUFA6, MPV17, TIMM50, UQCRQ, TIMM8B |
| GO:0044455~ mitochondrial membrane part | 8 | 2.235 | 0.00965 | NDUFS5, NDUFB5, NDUFA2, NDUFA3, NDUFA6, TOMM20, TIMM50, TIMM8B |

TABLE IIIE-continued

Annotation Cluster 5 (Enrichment Score: 1.264)

| Term | Count | % | P value | Genes |
|---|---|---|---|---|
| respiratory chain | 6 | 1.676 | 0.00969 | NDUFS5, NDUFB5, NDUFA2, NDUFA3, NDUFA6, UQCRQ |
| GO:0070469~ respiratory chain | 6 | 1.676 | 0.0138 | NDUFS5, NDUFB5, NDUFA2, NDUFA3, NDUFA6, UQCRQ |
| GO:0016655~ oxidoreductase activity, acting on NADH or NADPH, quinone, or similar compound as acceptor | 5 | 1.397 | 0.0139 | NDUFS5, NDUFB5, NDUFA2, NDUFA3, NDUFA6 |
| GO:0016651~ oxidoreductase activity, acting on NADH or NADPH | 6 | 1.676 | 0.0209 | NDUFS5, NDUFB5, NDUFA2, NDUFA3, NDUFA6, NQO2 |
| GO:0042773~ ATP synthesis coupled electron transport | 5 | 1.397 | 0.0227 | NDUFS5, NDUFB5, NDUFA2, NDUFA3, NDUFA6 |
| GO:0042775~ mitochondrial ATP synthesis coupled electron transport | 5 | 1.397 | 0.0227 | NDUFS5, NDUFB5, NDUFA2, NDUFA3, NDUFA6 |
| hsa05012: Parkinson's disease | 8 | 2.235 | 0.0263 | NDUFS5, NDUFB5, NDUFA2, NDUFA3, NDUFA6, SLC18A1, UQCRQ, VDAC1 |
| GO:0031967~ organelle envelope | 20 | 5.587 | 0.0266 | NDUFA2, NDUFB5, NDUFA3, HTATIP2, NDUFA6, MPV17, RANGAP1, TIMM50, UQCRQ, DCI, TIMM8B, VDAC1, NDUFS5, MRS2, MAD2L1, RAE1, TOMM20, PEBP1, KPNA5, KPNA3 |
| GO:0031975~ envelope | 20 | 5.587 | 0.0276 | NDUFS5, NDUFB5, NDUFA3, HTATIP2, NDUFA6, MPV17, RANGAP1, TIMM50, UQCRQ, DCI, TIMM8B, VDAC1, NDUFS5, MRS2, MAD2L1, RAE1, TOMM20, PEBP1, KPNA5, KPNA3 |
| GO:0005743~ mitochondrial inner membrane | 12 | 3.352 | 0.0315 | NDUFS5, NDUFB5, NDUFA2, MRS2, NDUFA3, NDUFA6, MPV17, TIMM50, UQCRQ, TIMM8B, DCI, VDAC1 |
| GO:0005746~ mitochondrial respiratory chain | 5 | 1.397 | 0.0329 | NDUFS5, NDUFB5, NDUFA2, NDUFA3, NDUFA6 |
| GO:0022904~ respiratory electron transport chain | 5 | 1.397 | 0.0349 | NDUFS5, NDUFB5, NDUFA2, NDUFA3, NDUFA6 |
| electron transport | 6 | 1.676 | 0.0367 | NDUFS5, NDUFB5, NDUFA2, NDUFA3, NDUFA6, UQCRQ |
| GO:0031966~ mitochondrial membrane | 14 | 3.911 | 0.0371 | NDUFA2, NDUFB5, NDUFA3, NDUFA6, MPV17, TIMM50, UQCRQ, TIMM8B, DCI, VDAC1, MRS2, NDUFS5, TOMM20, PEBP1 |
| GO:0006119~ oxidative phosphorylation | 6 | 1.676 | 0.0411 | NDUFS5, NDUFB5, NDUFA2, NDUFA3, NDUFA6, ATP6V0A2 |
| GO:0019866~ organelle inner membrane | 12 | 3.352 | 0.0492 | NDUFS5, NDUFB5, NDUFA2, MRS2, NDUFA3, NDUFA6, MPV17, TIMM50, UQCRQ, TIMM8B, DCI, VDAC1 |
| GO:0005740~ mitochondrial envelope | 14 | 3.911 | 0.0556 | NDUFA2, NDUFB5, NDUFA3, NDUFA6, MPV17, TIMM50, UQCRQ, TIMM8B, DCI, VDAC1, MRS2, NDUFS5, TOMM20, PEBP1 |
| GO:0022900~ electron transport chain | 6 | 1.676 | 0.0697 | NDUFS5, NDUFB5, NDUFA2, NDUFA3, NDUFA6, UQCRQ |
| hsa00190: Oxidative phosphorylation | 7 | 1.955 | 0.0756 | NDUFS5, NDUFB5, NDUFA2, NDUFA3, NDUFA6, UQCRQ, ATP6V0A2 |
| mitochondrion | 22 | 6.145 | 0.0862 | NDUFA2, NDUFB5, NDUFA3, NIT1, NDUFA6, MPV17, TIMM50, PCK2, UQCRQ, DCI, TIMM8B, VDAC1, ACOT9, NDUFS5, MRS2, TOMM20, NHEDC2, ACAD8, OGG1, ACAD9, WWOX, DUT |
| ubiquinone | 3 | 0.838 | 0.104 | NDUFS5, NDUFB5, NDUFA3 |
| GO:0045333~cellular respiration | 5 | 1.397 | 0.118 | NDUFS5, NDUFB5, NDUFA2, NDUFA3, NDUFA6 |
| hsa05010: Alzheimer's disease | 7 | 1.955 | 0.167 | NDUFS5, NDUFB5, NDUFA2, NDUFA3, NDUFA6, UQCRQ, NAE1 |
| hsa05016: Huntington's disease | 7 | 1.955 | 0.227 | NDUFS5, NDUFB5, NDUFA2, NDUFA3, NDUFA6, UQCRQ, VDAC1 |
| GO:0044429~ mitochondrial part | 15 | 4.190 | 0.239 | NDUFA2, NDUFB5, NDUFA3, NDUFA6, MPV17, TIMM50, UQCRQ, TIMM8B, DCI, VDAC1, MRS2, NDUFS5, POLDIP2, TOMM20, PEBP1 |

TABLE IIIE-continued

Annotation Cluster 5 (Enrichment Score: 1.264)

| Term | Count | % | P value | Genes |
|---|---|---|---|---|
| GO:0005739~ mitochondrion | 25 | 6.983 | 0.243 | ACOX1, NDUFB5, MPV17, TIMM50, VARS, UQCRQ, DCI, ACOT9, MRS2, NDUF55, ACAD8, ACAD9, WWOX, NDUFA2, NDUFA3, NDUFA6, PCK2, TIMM8B, VDAC1, POLDIP2, TOMM20, NHEDC2, PEBP1, OGG1, DUT |
| GO:0006091~ generation of precursor metabolites and energy | 9 | 2.514 | 0.259 | ACOX1, NDUFS5, NDUFB5, NDUFA2, NDUFA3, NDUFA6, UQCRQ, ATP6V0A2, EDARADD |
| NAD | 6 | 1.676 | 0.267 | XDH, NDUFB5, NDUFA2, NDUFA3, NDUFA6, SC4MOL |
| GO:0015980~ energy derivation by oxidation of organic compounds | 5 | 1.397 | 0.302 | NDUFS5, NDUFB5, NDUFA2, NDUFA3, NDUFA6 |
| GO:0031090~ organelle membrane | 23 | 6.425 | 0.419 | ACOX1, NDUFA2, NDUFB5, NDUFA3, DUOXA2, NDUFA6, MPV17, TIMM50, MAN1A1, UQCRQ, DCI, TIMM8B, SC4MOL, VDAC1, NDUFS5, GAD2, MRS2, RAE1, TOMM20, VPS4A, PEBP1, RAB11FIP1, ATP6V0A2 |
| transit peptide: Mitochondrion | 9 | 2.514 | 0.632 | ACOT9, NDUFB5, MRS2, TIMM50, ACAD8, PCK2, ACAD9, DCI, DUT |
| transit peptide | 9 | 2.514 | 0.646 | ACOT9, NDUFB5, MRS2, TIMM50, ACAD8, PCK2, ACAD9, DCI, DUT |
| GO:0016310~ phosphorylation | 7 | 1.955 | 0.998 | NDUFS5, NDUFB5, NDUFA2, NDUFA3, NDUFA6, IFNG, ATP6V0A2 |
| GO:0006793~ phosphorus metabolic process | 9 | 2.514 | 0.999 | NDUFS5, NDUFB5, NDUFA2, NDUFA3, SLC20A1, NDUFA6, IFNG, TIMM50, ATP6V0A2 |
| GO:0006796~ phosphate metabolic process | 9 | 2.514 | 0.999 | NDUFS5, NDUFB5, NDUFA2, NDUFA3, SLC20A1, NDUFA6, IFNG, TIMM50, ATP6V0A2 |

TABLE IIIF

Annotation Cluster 6 (Enrichment Score: 1.174)

| Term | Count | % | P value | Genes |
|---|---|---|---|---|
| EGF-like domain | 11 | 3.0726 | 0.0101 | TMEFF2, PRF1, F12, TNXB, CRB1, NELL1, FAT2, LRP6, FBLN7, CFC1, PROC |
| IPR006210: EGF-like | 10 | 2.793 | 0.0168 | TMEFF2, F12, TNXB, CRB1, NELL1, FAT2, LRP6, FBLN7, CFC1, PROC |
| SM00181:EGF | 10 | 2.793 | 0.0210 | TMEFF2, F12, TNXB, CRB1, NELL1, FAT2, LRP6, FBLN7, CFC1, PROC |
| domain: EGF-like 2 | 6 | 1.676 | 0.0233 | F12, TNXB, CRB1, FAT2, LRP6, PROC |
| IPR000742: EGF-like, type 3 | 9 | 2.514 | 0.0357 | TMEFF2, F12, TNXB, CRB1, NELL1, FAT2, LRP6, FBLN7, CFC1, PROC |
| IPR006209: EGF | 7 | 1.955 | 0.0374 | TMEFF2, F12, CRB1, FAT2, LRP6, FBLN7, PROC |
| IPR013032: EGF-like region, conserved site | 11 | 3.0726 | 0.0599 | TMEFF2, PRF1, F12, TNXB, CRB1, NELL1, FAT2, LRP6, FBLN7, CFC1, PROC |
| domain: EGF-like 1 | 6 | 1.676 | 0.0712 | F12, CRB1, NELL1, FAT2, LRP6, PROC |
| domain: EGF-like 3 | 4 | 1.117 | 0.160 | TNXB, CRB1, NELL1, LRP6 |
| IPR001881: EGF-like calcium-binding | 4 | 1.117 | 0.285 | CRB1, NELL1, FBLN7, PROC |
| IPR018097: EGF-like calcium-binding, conserved site | 4 | 1.117 | 0.285 | CRB1, NELL1, FBLN7, PROC |
| IPR000152: EGF-type aspartate/asparagine hydroxylation conserved site | 4 | 1.117 | 0.291 | CRB1, NELL1, FBLN7, PROC |
| SM00179: EGF_CA | 4 | 1.117 | 0.308 | CRB1, NELL1, FBLN7, PROC |

TABLE IIIG

Annotation Cluster 7 (Enrichment Score: 1.172)

| Term | Count | % | P value | Genes |
|---|---|---|---|---|
| domain: PDZ | 6 | 1.676 | 0.0528 | DVL2, SHROOM2, PREX1, SNTB1, LDB3, AHNAK |
| IPR001478: PDZ/DHR/GLGF | 7 | 1.955 | 0.0703 | DVL2, SHROOM2, PREX1, SNTB1, LDB3, PDZRN3, AHNAK |
| SM00228: PDZ | 7 | 1.955 | 0.0822 | DVL2, SHROOM2, PREX1, SNTB1, LDB3, PDZRN3, AHNAK |

TABLE IIIH

Annotation Cluster 8 (Enrichment Score: 1.058)

| Term | Count | % | P value | Genes |
|---|---|---|---|---|
| IPR004046: Glutathione S-transferase, C-term. | 3 | 0.838 | 0.0618 | GSTM3, GSTA3, VARS |

TABLE IIIH-continued

Annotation Cluster 8 (Enrichment Score: 1.058)

| Term | Count | % | P value | Genes |
|---|---|---|---|---|
| IPR004045: Glutathione S-transferase, N-term. | 3 | 0.8383 | 0.0671 | GSTM3, GSTA3, VARS |
| IPR017933: Glutathione S-transferase/chloride channel, C-term. | 3 | 0.838 | 0.114 | GSTM3, GSTA3, VARS |
| domain: GST C-term. | 3 | 0.838 | 0.123 | GSTM3, GSTA3, VARS |

TABLE IIII

Annotation Cluster 9 (Enrichment Score: 1.032)

| Term | Count | % | P value | Genes |
|---|---|---|---|---|
| GO:0005615~ extracellular space | 24 | 6.704 | 0.00555 | LALBA, F12, TNXB, PZP, CMTM2, TNFSF4, CXCL2, CST3, IGF1, CCL5, CCL4, METRN, CPAMD8, PRSS2, SOSTDC1, SEMA3F, IFNA4, APOC3, IFNG, CFH, PEBP1, IFNA8, CFI, SEPP1 |
| GO:0044421~ extracellular region part | 30 | 8.380 | 0.00828 | LALBA, PZP, CXCL2, CCL5, CCL4, NOV, METRN, PRSS2, SEMA3F, SOSTDC1, APOC3, IFNA4, IFNG, CFH, CFI, SEPP1, IFNA8, F12, FLRT1, TNXB, TNFSF4, CMTM2, COL13A1, CST3, IGF1, ADAMTS6, WNT7B, CPAMD8, FBLN7, PEBP1 |
| GO:0005576~ extracellular region | 48 | 13.408 | 0.0689 | LALBA, PRF1, PZP, PDGFB, NELL1, CXCL2, CCL5, CCL4, NOV, F13B, METRN, FAM150A, CRB1, CRISPLD1, PRSS2, SOSTDC1, SEMA3F, IFNG, IFNA4, APOC3, CFH, IFNA8, SEPP1, CFI, C140RF93, CD200R1, TMEFF2, F12, FLRT1, C2CD2, TNXB, CMTM2, TNFSF4, COL13A1, CST3, IGF1, PROC, LYZL1, ADAMTS6, WNT7B, CPAMD8, CCDC70, SRCRB4D, KRTAP1-1, FBLN7, PEBP1, SCGB2A2, NPPA |
| Secreted | 40 | 11.173 | 0.0771 | LALBA, XDH, PRF1, PZP, PDGFB, NELL1, CXCL2, CCL5, CCL4, NOV, METRN, FAM150A, CRB1, CRISPLD1, PRSS2, SEMA3F, SOSTDC1, IFNA4, APOC3, IFNG, CFH, IFNA8, CFI, SEPP1, C140RF93, CD200R1, TMEFF2, F12, C2CD2, TNXB, CST3, IGF1, LYZL1, ADAMTS6, WNT7B, CPAMD8, CCDC70, SRCRB4D, FBLN7, NPPA |
| disulfide bond | 64 | 17.877 | 0.0909 | PZP, PDGFB, OR2J3, NELL1, HEXA, NOV, UNC5B, SOSTDC1, SEMA3F, CEACAM7, CFH, CFI, CD200R1, TMEFF2, F12, OR4A47, OR4M2, CST3, OR10J5, MAN1A1, EDAR, CFC1, TIMM8B, PROC, HCST, LYZL1, ADAMTS6, SRCRB4D, MFAP3, BTN3A3, NPPA, LALBA, XDH, PRF1, CXCL2, NPY6R, CCL5, CCL4, PKD1L2, F13B, OR10G8, CRB1, CRISPLD1, PRSS2, OR52N1, LY6H, FAT2, IFNA4, PKD1, IFNA8, HTR3C, PLP1, NDUFA2, TNFSF4, TNXB, B4GALT2, COL13A1, IGF1, OR11H1, LAMP1, OR51M1, FBLN7, LRP6, SCN4B |
| disulfide bond | 61 | 17.0391 | 0.126 | PDGFB, OR2J3, NELL1, HEXA, NOV, UNC5B, SOSTDC1, SEMA3F, CEACAM7, CFH, CFI, CD200R1, TMEFF2, F12, OR4A47, OR4M2, CST3, OR10J5, MAN1A1, EDAR, CFC1, TIMM8B, PROC, LYZL1, ADAMTS6, SRCRB4D, MFAP3, BTN3A3, NPPA, LALBA, XDH, PRF1, CXCL2, NPY6R, CCL5, CCL4, PKD1L2, F13B, OR10G8, CRB1, CRISPLD1, PRSS2, OR52N1, LY6H, FAT2, IFNA4, PKD1, IFNA8, HTR3C, PLP1, NDUFA2, TNFSF4, TNXB, B4GALT2, IGF1, OR11H1, LAMP1, OR51M1, FBLN7, LRP6, SCN4B |

TABLE IIII-continued

Annotation Cluster 9 (Enrichment Score: 1.032)

| Term | Count | % | P value | Genes |
|---|---|---|---|---|
| signal | 68 | 18.994 | 0.157 | PZP, PDGFB, NELL1, HEXA, APCDD1, ASAH1, NOV, METRN, FAM150A, UNC5B, SOSTDC1, SEMA3F, IFNG, CEACAM7, CFH, SEPP1, CFI, PILRB, C14ORF93, CD200R1, TMEFF2, F12, C2CD2, PDPN, CST3, EDAR, CFC1, PROC, HCST, LYZL1, ADAMTS6, CCDC3, PLEKHH3, CPAMD8, SRCRB4D, MFAP3, BTN3A3, SCGB2A2, NPPA, FKBP2, LALBA, PRF1, CXCL2, CCL5, CCL4, PKD1L2, F13B, CRB1, CRISPLD1, PRSS2, LY6H, APOC3, FAT2, IFNA4, PKD1, IFNA8, LRFN5, UGT2B28, HTR3C, FLRT1, TNXB, IGF1, LAMP1, WNT7B, CCDC70, FBLN7, LRP6, SCN4B |
| signal peptide | 68 | 18.994 | 0.170 | PZP, PDGFB, NELL1, HEXA, APCDD1, ASAH1, NOV, METRN, FAM150A, UNC5B, SOSTDC1, SEMA3F, IFNG, CEACAM7, CFH, SEPP1, CFI, PILRB, C14ORF93, CD200R1, TMEFF2, F12, C2CD2, PDPN, CST3, EDAR, CFC1, PROC, HCST, LYZL1, ADAMTS6, CCDC3, PLEKHH3, CPAMD8, SRCRB4D, MFAP3, BTN3A3, SCGB2A2, NPPA, FKBP2, LALBA, PRF1, CXCL2, CCL5, CCL4, PKD1L2, F13B, CRB1, CRISPLD1, PRSS2, LY6H, APOC3, FAT2, IFNA4, PKD1, IFNA8, LRFN5, UGT2B28, HTR3C, FLRT1, TNXB, IGF1, LAMP1, WNT7B, CCDC70, FBLN7, LRP6, SCN4B |
| glycoprotein | 75 | 20.950 | 0.760 | PZP, HEXA, NELL1, OR2J3, APCDD1, ASAH1, NOV, UNC5B, SOSTDC1, SEMA3F, IFNG, CFH, CEACAM7, CH5T14, SEPP1, CFI, PILRB, CD200R1, TMEFF2, F12, DUOXA2, SLCO4A1, PDPN, SLC22A23, OR4A47, OR4M2, OR10J5, MAN1A1, EDAR, CFC1, PROC, HCST, LYZL1, ADAMTS6, CPAMD8, CD82, MFAP3, BTN3A3, SCGB2A2, FAIM2, XDH, LALBA, PRF1, GCNT2, OR5D16, NPY6R, CCL5, PKD1L2, F13B, OR10G8, CRB1, OR52N1, LY6H, APOC3, FAT2, PKD1, LRFN5, UGT2B28, FLRT1, TNFSF4, TNXB, B4GALT2, COL13A1, RHBDF1, OR11H1, B3GAT2, OR5T1, LAMP1, OR51M1, WNT7B, FBLN7, LRP6, SCN4B, SLC18A1, SLC14A2 |
| glycosylation site: N-linked (GlcNAc...) | 70 | 19.553 | 0.838 | PZP, HEXA, NELL1, OR2J3, APCDD1, ASAH1, NOV, UNC5B, SOSTDC1, SEMA3F, IFNG, CEACAM7, CFH, CHST14, SEPP1, CFI, PILRB, CD200R1, TMEFF2, F12, DUOXA2, SLCO4A1, SLC22A23, OR4A47, OR4M2, OR10J5, MAN1A1, EDAR, CFC1, PROC, LYZL1, ADAMTS6, CPAMD8, CD82, MFAP3, BTN3A3, SCGB2A2, FAIM2, XDH, LALBA, PRF1, GCNT2, OR5D16, NPY6R, PKD1L2, F13B, OR10G8, CRB1, OR52N1, LY6H, FAT2, PKD1, LRFN5, UGT2B28, FLRT1, TNFSF4, TNXB, B4GALT2, RHBDF1, OR11H1, B3GAT2, OR5T1, LAMP1, OR51M1, WNT7B, FBLN7, LRP6, SCN4B, SLC18A1, SLC14A2 |

TABLE IIIJ

Annotation Cluster 10 (Enrichment Score: 1.009)

| Term | Count | % | P value | Genes |
|---|---|---|---|---|
| GO:0030193~ regulation of blood coagulation | 4 | 1.117 | 0.0317 | F12, PDGFB, PDPN, PROC |
| GO:0050818~ regulation of coagulation | 4 | 1.117 | 0.0442 | F12, PDGFB, PDPN, PROC |

TABLE IIIJ-continued

Annotation Cluster 10 (Enrichment Score: 1.009)

| Term | Count | % | P value | Genes |
|---|---|---|---|---|
| GO:0030195~ negative regulation of blood coagulation | 3 | 0.838 | 0.0719 | F12, PDGFB, PROC |
| GO:0050819~ negative regulation of coagulation | 3 | 0.838 | 0.0890 | F12, PDGFB, PROC |
| GO:0051241~ negative regulation of multicellular organismal process | 7 | 1.955 | 0.0981 | ATXN2, F12, PDGFB, IFNG, APOC3, CST3, PROC |
| GO:0032101~ regulation of response to external stimulus | 6 | 1.676 | 0.194 | F12, SBN02, PDGFB, PDPN, CCL5, PROC |
| GO:0042060~ wound healing | 5 | 1.397 | 0.505 | F13B, F12, PDGFB, IGF1, PROC |

TABLE IIIK

Annotation Cluster 11 (Enrichment Score: 0.983)

| Term | Count | % | P value | Genes |
|---|---|---|---|---|
| ectodermal dysplasia | 5 | 1.397 | 8.77E-04 | KRT6B, KRT14, EDAR, GJB6, EDARADD |
| GO:0042475~ odontogenesis of dentine- containing tooth | 4 | 1.117 | 0.0390 | SOSTDC1, EDAR, GLI2, EDARADD |
| GO:0042476~ odontogenesis | 4 | 1.117 | 0.0860 | SOSTDC1, EDAR, GLI2, EDARADD |
| GO:0007398~ ectoderm development | 7 | 1.955 | 0.186 | KRT6B, TGM1, KRT14, KRT2, EDAR, GLI2, EDARADD |
| GO:0008544~ epidermis development | 6 | 1.676 | 0.282 | TGM1, KRT14, KRT2, EDAR, GLI2, EDARADD |
| GO:0009913~ epidermal cell differentiation | 3 | 0.838 | 0.406 | TGM1, KRT2, GLI2 |
| GO:0060429~ epithelium development | 6 | 1.676 | 0.443 | DVL2, GSTM3, TGM1, KRT14, KRT2, GLI2 |
| GO:0030855~ epithelial cell differentiation | 4 | 1.117 | 0.495 | GSTM3, TGM1, KRT14, KRT2 |

TABLE IIIL

Annotation Cluster 12 (Enrichment Score: 0.898)

| Term | Count | % | P value | Genes |
|---|---|---|---|---|
| IPR000591: Pleckstrin/G-protein, interacting region | 3 | 0.838 | 0.0618 | DVL2, PLEK2, PREX1 |
| SM00049: DEP | 3 | 0.838 | 0.0667 | DVL2, PLEK2, PREX1 |
| IPR011991: Winged helix repressor DNA-binding | 5 | 1.397 | 0.492 | DVL2, E2F3, FOXI2, PLEK2, PREX1 |

TABLE IIIM

Annotation Cluster 13 (Enrichment Score: 0.885)

| Term | Count | % | P value | Genes |
|---|---|---|---|---|
| domain: B30.2/SPRY | 5 | 1.397 | 0.0648 | TRIM16L, LOC283116, SPSB2, BTN3A3, SPRYD5 |
| IPR003877: SPla/RYanodine receptor SPRY | 5 | 1.397 | 0.0804 | TRIM16L, LOC283116, SPSB2, BTN3A3, SPRYD5 |
| IPR001870: B302 (SPRY)-like | 5 | 1.3975 | 0.0888 | TRIM16L, LOC283116, SPSB2, BTN3A3, SPRYD5 |
| IPR003879: butyrophylin-like | 4 | 1.117 | 0.119 | TRIM16L, LOC283116, BTN3A3, SPRYD5 |
| IPR018355: SPla/RYanodine receptor subgroup | 3 | 0.838 | 0.289 | TRIM16L, SPSB2, BTN3A3 |
| SM00449: SPRY | 3 | 0.838 | 0.307 | TRIM16L, SPSB2, BTN3A3 |

TABLE IIIN

Annotation Cluster 14 (Enrichment Score: 0.847)

| Term | Count | % | P value | Genes |
|---|---|---|---|---|
| domain: Death | 3 | 0.838 | 0.136 | UNC5B, EDAR, EDARADD |
| IPR000488: Death | 3 | 0.838 | 0.140 | UNC5B, EDAR, EDARADD |
| SM00005: DEATH | 3 | 0.838 | 0.151 | UNC5B, EDAR, EDARADD |

TABLE IIIO

Annotation Cluster 15 (Enrichment Score: 0.824)

| Term | Count | % | P value | Genes |
|---|---|---|---|---|
| cytokine | 8 | 2.235 | 0.0493 | TNFSF4, CMTM2, CXCL2, IFNG, IFNA4, IFNA8, CCL5, CCL4 |
| GO:0006952~ defense response | 19 | 5.307 | 0.0527 | LALBA, F12, PRF1, TNFSF4, CEBPE, PDPN, NFRKB, CXCL2, CST3, SOCS6, CCL5, VARS, CCL4, VDAC1, IFNA4, IFNG, CFH, CFI, IFNA8 |
| GO:0005125~ cytokine activity | 8 | 2.235 | 0.0803 | TNFSF4, CMTM2, CXCL2, IFNG, IFNA4, IFNA8, CCL5, CCL4 |
| GO:0009611~ response to wounding | 14 | 3.911 | 0.219 | F12, TNFSF4, PDGFB, PDPN, NFRKB, CXCL2, IGF1, CCL5, CCL4, PROC, F13B, CFH, PEBP1, CFI |
| GO:0006954~ inflammatory response | 9 | 2.514 | 0.289 | F12, TNFSF4, PDPN, NFRKB, CXCL2, CFH, CFI, CCL5, CCL4 |
| GO:0006955~ immune response | 11 | 3.0726 | 0.863 | F12, SBNO2, TNFSF4, CXCL2, IFNG, CFH, CFI, CCL5, VAV1, CCL4, ATP6V0A2 |

TABLE IIIP

Annotation Cluster 16 (Enrichment Score: 0.820)

| Term | Count | % | P value | Genes |
|---|---|---|---|---|
| GO:0007626~ locomotory behavior | 12 | 3.352 | 0.0175 | ATXN1, SNCG, CMTM2, PDGFB, HEXA, SEMA3F, CXCL2, IFNG, CACNB4, SEPP1, CCL5, CCL4 |

TABLE IIIP-continued

Annotation Cluster 16 (Enrichment Score: 0.820)

| Term | Count | % | P value | Genes |
|---|---|---|---|---|
| antiviral | 3 | 0.838 | 0.0263 | IFNG, IFNA4, IFNA8 |
| cytokine | 8 | 2.235 | 0.0493 | TNFSF4, CMTM2, CXCL2, IFNG, IFNA4, IFNA8, CCL5, CCL4 |
| inflammation | 3 | 0.838 | 0.0760 | CXCL2, CCL5, CCL4 |
| GO:0005125~ cytokine activity | 8 | 2.235 | 0.0803 | TNFSF4, CMTM2, CXCL2, IFNG, IFNA4, IFNA8, CCL5, CCL4 |
| GO:0006935~ chemotaxis | 7 | 1.955 | 0.0897 | CMTM2, PDGFB, SEMA3F, CXCL2, IFNG, CCL5, CCL4 |
| GO:0042330~ taxis | 7 | 1.955 | 0.0897 | CMTM2, PDGFB, SEMA3F, CXCL2, IFNG, CCL5, CCL4 |
| GO:0007610~ behavior | 14 | 3.911 | 0.121 | SNCG, CMTM2, PDGFB, HEXA, CXCL2, CACNB4, CCL5, CCL4, VDAC1, ATXN1, SEMA3F, IFNG, PEBP1, SEPP1 |
| hsa04623: Cytosolic DNA-sensing pathway | 4 | 1.117 | 0.130 | IFNA4, IFNA8, CCL5, CCL4 |
| chemotaxis | 4 | 1.117 | 0.145 | CMTM2, CXCL2, CCL5, CCL4 |
| GO:0009615~ response to virus | 5 | 1.397 | 0.160 | IFNG, IFNA4, IFNA8, CCL5, CCL4 |
| hsa04650: Natural killer cell mediated cytotoxicity | 6 | 1.676 | 0.186 | PRF1, IFNG, IFNA4, IFNA8, VAV1, HCST |
| IPR001811: Small chemokine, interleukin-8-like | 3 | 0.838 | 0.189 | CXCL2, CCL5, CCL4 |
| hsa04140: Regulation of autophagy | 3 | 0.838 | 0.189 | IFNG, IFNA4, IFNA8 |
| pharmaceutical | 3 | 0.838 | 0.192 | PDGFB, CXCL2, IFNG |
| 5M00199: SCY | 3 | 0.838 | 0.202 | CXCL2, CCL5, CCL4 |
| GO:0008009~ chemokine activity | 3 | 0.838 | 0.218 | CXCL2, CCL5, CCL4 |
| IPR012351: Four-helical cytokine, core | 3 | 0.838 | 0.2243 | IFNG, IFNA4, IFNA8 |
| GO:0042379~ chemokine receptor binding | 3 | 0.838 | 0.239 | CXCL2, CCL5, CCL4 |
| hsa04060: Cytokine-cytokine receptor interaction | 9 | 2.514 | 0.247 | TNFSF4, PDGFB, CXCL2, IFNG, IFNA4, IFNA8, EDAR, CCL5, CCL4 |
| antiviral defense | 3 | 0.838 | 0.314 | IFNG, IFNA4, IFNA8 |
| hsa04620: Toll-like receptor signaling pathway | 4 | 1.117 | 0.407 | IFNA4, IFNA8, CCL5, CCL4 |
| inflammatory response | 3 | 0.838 | 0.413 | CXCL2, CCL5, CCL4 |
| hsa04062: Chemokine signaling pathway | 6 | 1.676 | 0.424 | PREX1, CXCL2, GNG4, CCL5, VAV1, CCL4 |
| hsa04630: Jak-STAT signaling pathway | 5 | 1.397 | 0.474 | CCND2, IFNG, IFNA4, STAM, IFNA8 |

TABLE IIIQ

Annotation Cluster 17 (Enrichment Score: 0.816)

| Term | Count | % | P value | Genes |
|---|---|---|---|---|
| domain: EGF-like 1 | 6 | 1.676 | 0.0712 | F12, CRB1, NELL1, FAT2, LRP6, PROC |
| IPR001791: Laminin G | 3 | 0.838 | 0.217 | CRB1, NELL1, FAT2 |
| SM00282: LamG | 3 | 0.838 | 0.231 | CRB1, NELL1, FAT2 |

TABLE IIIR

Annotation Cluster 18 (Enrichment Score: 0.789)

| Term | Count | % | P value | Genes |
|---|---|---|---|---|
| GO:0048705~ skeletal system morphogenesis | 6 | 1.676 | 0.0657 | ZFAND5, THRA, COL13A1, PRRX1, PKD1, WWOX |
| GO:0001501~ skeletal system development | 11 | 3.0726 | 0.0884 | ZFAND5, THRA, COL13A1, HEXA, TRPS1, HOXD12, PRRX1, IGF1, PKD1, GLI2, WWOX |
| GO:0001503~ ossification | 5 | 1.397 | 0.182 | THRA, COL13A1, IGF1, GLI2, WWOX |
| GO:0001649~ osteoblast differentiation | 3 | 0.838 | 0.194 | IGF1, GLI2, WWOX |
| GO:00603~ bone development | 5 | 1.397 | 0.214 | THRA, COL13A1, IGF1, GLI2, WWOX |
| GO:0001763~ morphogenesis of a branching structure | 3 | 0.838 | 0.420 | COL13A1, IGF1, GLI2 |

TABLE IIIS

Annotation Cluster 19 (Enrichment Score: 0.788)

| Term | Count | % | P value | Genes |
|---|---|---|---|---|
| GO:0046930~ pore complex | 6 | 1.676 | 0.0342 | MAD2L1, RAE1, KPNA5, RANGAP1, KPNA3, VDAC1 |

TABLE IIIS-continued

Annotation Cluster 19 (Enrichment Score: 0.788)

| Term | Count | % | P value | Genes |
|---|---|---|---|---|
| GO:0005643~ nuclear pore | 5 | 1.397 | 0.0627 | MAD2L1, RAE1, KPNA5, RANGAP1, KPNA3 |
| GO:0005635~ nuclear envelope | 6 | 1.676 | 0.3524 | MAD2L1, HTATIP2, RAE1, KPNA5, RANGAP1, KPNA3 |
| GO:0012505- endomembrane system | 11 | 3.0726 | 0.932 | GAD2, MAD2L1, HTATIP2, DUOXA2, RAE1, KPNA5, RANGAP1, MAN1A1, KPNA3, RAB11FIP1, SC4MOL |

TABLE IIIT

Annotation Cluster 20 (Enrichment Score: 0.777)

| Term | Count | % | P value | Genes |
|---|---|---|---|---|
| domain: SOCS box | 3 | 0.838 | 0.155 | SPSB2, SOCS6, ASB7 |
| IPR001496: SOCS protein, C-term. | 3 | 0.838 | 0.168 | SPSB2, SOCS6, ASB7 |
| SM00253: SOCS | 3 | 0.838 | 0.179 | SPSB2, SOCS6, ASB7 |

Figure 2C:
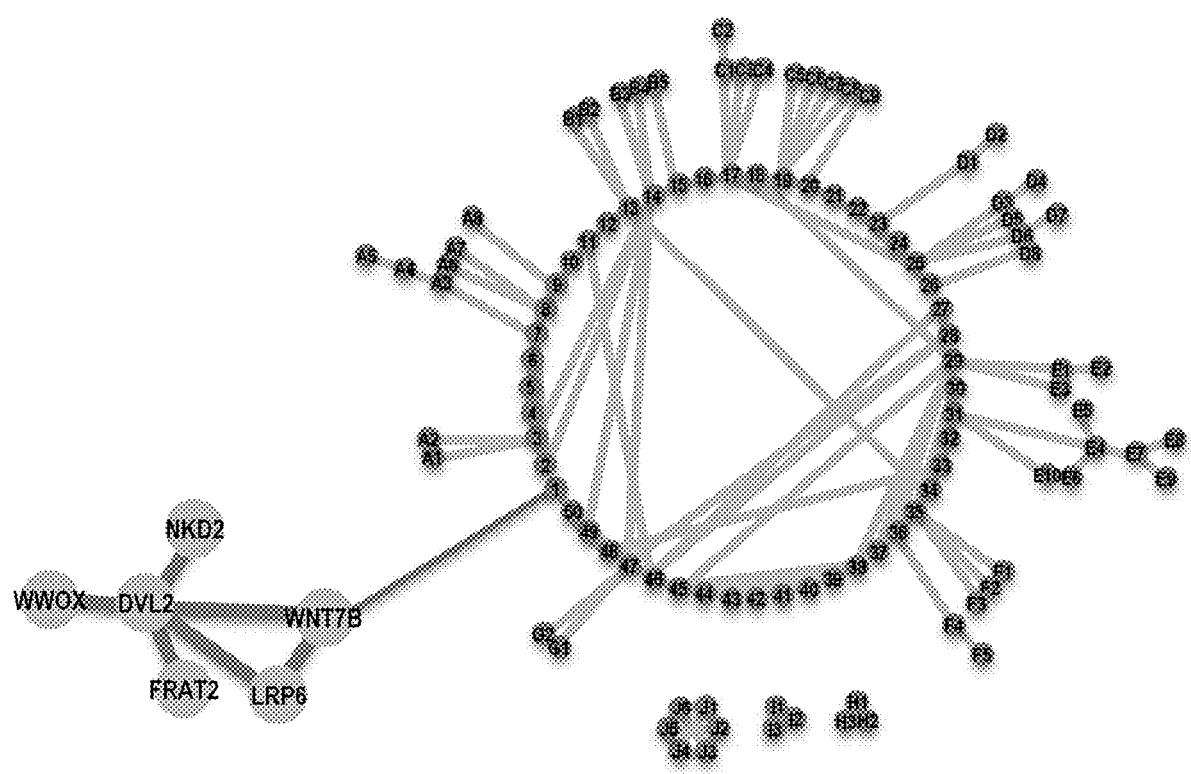

Lastly, the hit list was subjected to the protein-protein interaction database STRING, to identify proteins known or predicted to interact within the list (see, e.g., Franceschini A et al., "STRING v9.1: protein-protein interaction networks, with increased coverage and integration," *Nucleic Acids Res.* 2013; 41(Database issue):D808-15). As shown in FIG. 2C, amongst the most represented cluster of interacting proteins are those related to the Wnt pathway.

Figure 3A:
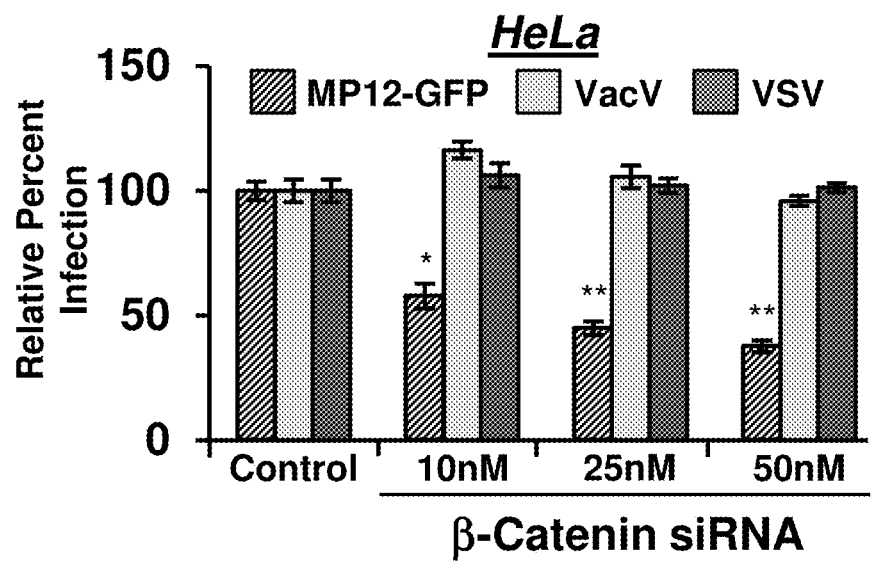
FIG. 3A-3D shows that the canonical Wnt signaling pathway plays a significant role in RVFV infection. Provided are graphs showing relative percent infection of HeLa cells (FIG. 3A) and 293T cells (FIG. 3B) that were transfected with siRNAs targeting β-catenin or 50 nM of control siRNA, then infected with the GFP reporter viruses (MP12-GFP, VacV, or VSV at MOI=1). The percentage of infection was determined by taking control and infected samples as 100%. Shown are the means (±S.D.) for three independent experiments performed in triplicate (**, P<0.01; *, P<0.05). Also provided are Western blots for whole cell lysates of transfected HeLa cells (FIG. 3C) or 293T cells (FIG. 3D) that were washed and lysed at 60 hpt. The relative reduction index (RI) was measured as described herein. The data represent one of three experiments with similar results.
Figure 3B:
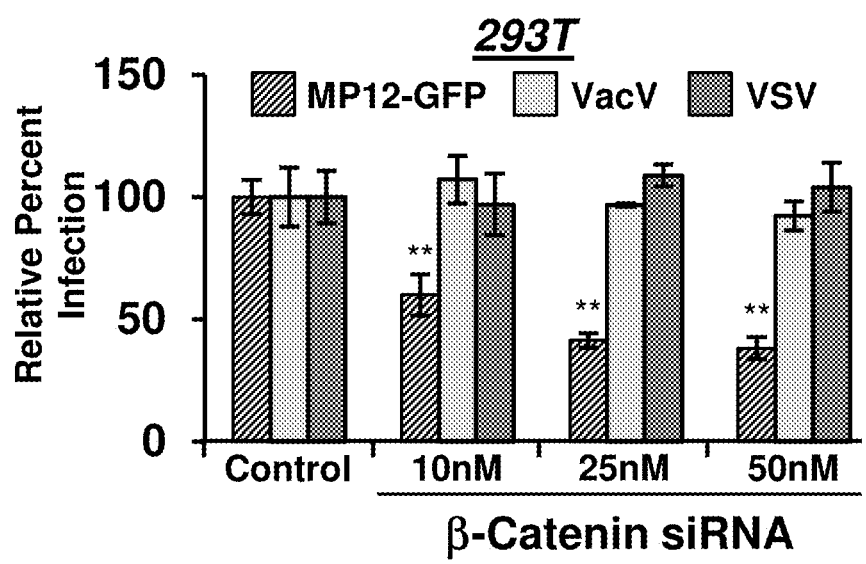
Figure 3C:
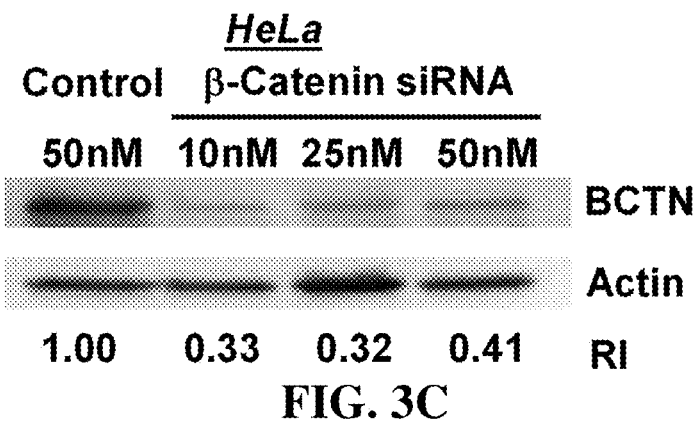
Figure 3D:
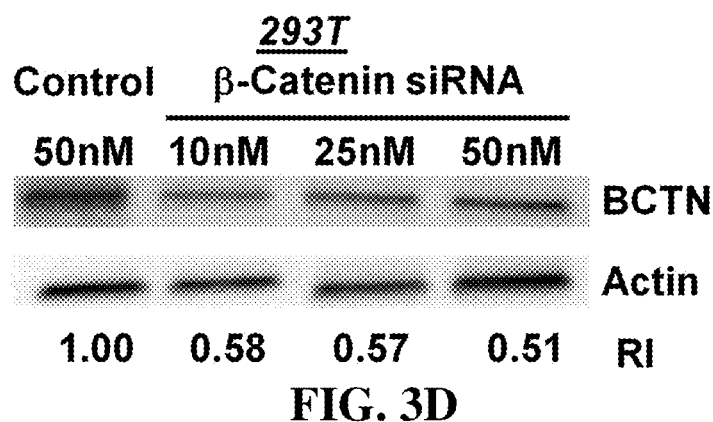

To verify the role of Wnt signaling in RVFV infection and to distinguish between canonical Wnt signaling involving β-catenin and β-catenin-independent non-canonical Wnt pathways, we transfected HeLa cells with increasing concentrations of siRNA targeting β-catenin, and these cells were mock-infected or infected with RVFV MP12-GFP, Vaccinia virus expressing GFP (VacV), or Vesicular Stomatitis virus expressing GFP (VSV) at an MOI of 1. Infection with RVFV MP12-GFP was reduced in a dose-dependent manner in siRNA-transfected HeLa cells (FIG. 3A) and 293T cells (FIG. 3B). The decrease in RVFV MP12-GFP infection correlated with the decreased steady-state levels of β-catenin at 60 hours post-transfection (hpt), as detected by immunoblotting (FIG. 3C-3D). Although β-catenin was not identified as a hit in our screen, we found that the best knockdown of β-catenin was observed at 60 hours, and there was very little knockdown at 48 hours (when cells were infected for the screen). Accordingly, RVFV MP12-GFP infection was reduced 60 hpt with β-catenin siRNA (FIGS. 3C-3D), and not at 48 hpt (data not shown).

Infection of HeLa cells (FIG. 3A) or 293T cells (FIG. 3B) with VacV or VSV was unaffected by downregulation of β-catenin. Interestingly, each of these viruses replicate in the cell cytoplasm yet only RVFV MP12-GFP was inhibited by a reduction in the canonical Wnt signaling protein β-catenin, thereby suggesting a specific role for Wnt/β-catenin signaling in RVFV infection.

Example 4: RVFV Induces Wnt/β-Catenin Signaling and Pre-Activation of Wnt Signaling Enhances RVFV Infection To further investigate the role of Wnt/β-catenin signaling in RVFV infection, the TCF/LEF luciferase (luc) reporter construct TOPflash (TF) was used to determine whether RVFV infection induces β-catenin-dependent transcriptional activity. 293T cells were transiently transfected with TF for 18 hours and subsequently infected with the non-recombinant RVFV strain MP12 (RVFV MP12) or RVFV MP12-GFP at an MOI of 1. As a positive control, cells were also separately treated with the canonical Wnt3A ligand. The cells were then analyzed for luc expression between 2 to 7 hours post-infection (hpi) or post-treatment (hpt). It has been previously demonstrated that RVFV proteins begin to accumulate 2 hpi and steadily increase within this measurement time frame (see, e.g., Ikegami T et al., *PLoS Pathog.* 2009; 5(2):e1000287 (17 pp.)).

Figure 4A:
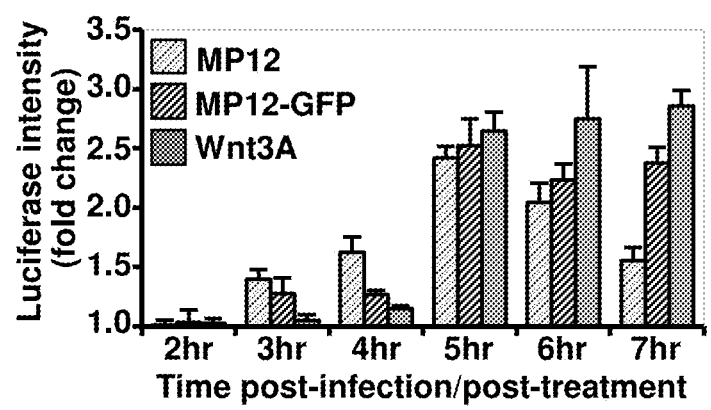

As shown in FIG. 4A, RVFV MP12 and RVFV MP12-GFP-induced β-catenin reporter activity to levels similar to Wnt3A stimulation at 5 hpi. The reporter activity remained elevated after 6 and 7 hours of treatment with Wnt3A or infection with RVFV MP12-GFP, whereas β-catenin reporter activity peaked at 5 hpi and decreased thereafter in cells infected with RVFV MP12. Unlike RVFV MP12-GFP, RVFV MP12 contains the nonstructural protein NSs. Since NSs is known to downregulate cellular transcription, NSs is likely responsible for decreased β-catenin/TCF/LEF complex reporter activity in late stages of infection. However, activation is not dependent on NSs since RVFV MP12 and RVFV MP12-GFP (ΔNSs) infection similarly induced β-catenin dependent transcriptional activity.

Figure 4B:
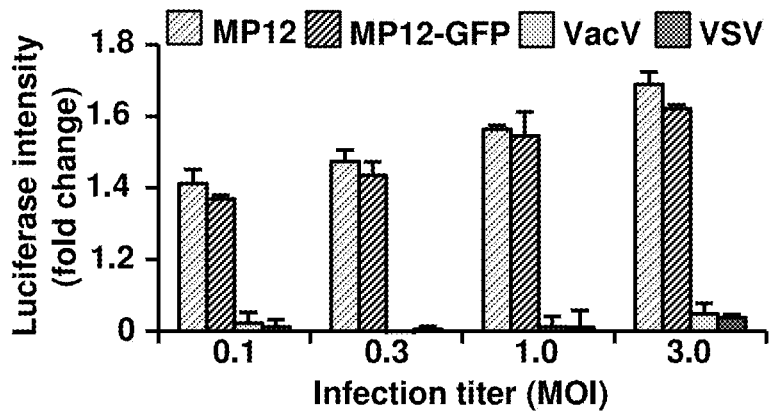

RVFV MP12 and RVFV MP12-GFP infections were also shown to similarly promote β-catenin reporter activation across a range of infectious doses measured at 5 hpi (FIG. 4B). In contrast to RVFV MP12 and RVFV MP12-GFP, VSV and VacV did not activate luc expression through the TCF/LEF promoter using equivalent infectious titers, to RVFV MP12 and RVFV MP12-GFP (FIG. 4B). Therefore, RVFV seems to specifically induce Wnt signaling.

Figure 4C:
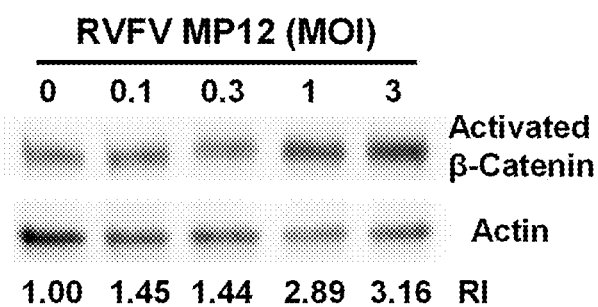

Another way to measure Wnt/β-catenin activation is through the analysis of β-catenin phosphorylation (see, e.g., Hadjihannas M V et al., *EMBO Rep.* 2010; 11(4):317-24). Again, in the OFF state of canonical Wnt signaling, CK1 phosphorylates β-catenin specifically at Ser45. This phosphorylation event primes β-catenin for subsequent phosphorylation by GSK-3 at Ser33, Ser37, and Thr41; and phosphorylated β-catenin is then targeted for ubiquitination and proteasomal degradation. In the ON state, there is a rise in the stabilized (non-phosphorylated) form of β-catenin (see, e.g., Clevers H et al., *Cell* 2012; 149(6):1192-205; and Li V S et al., *Cell* 2012; 149(6):1245-56). Therefore, using an antibody designed to specifically detect non-phosphorylated sites Ser33/37/Thr41 of β-catenin, we probed 293T cell lysates after infection with RVFV MP12 at a range of infectious doses for functionally active β-catenin (see, e.g., Klaus A et al., *Nat. Rev. Cancer* 2008; 8(5):387-98; and Clevers H et al., *Cell* 2012; 149(6):1192-205). As shown in FIG. 4C, RVFV MP12 infection of cells with an MOI of 1 or 3 for 4.5 hours induced about 3-fold increase in levels of activated β-catenin.

Figure 4D:
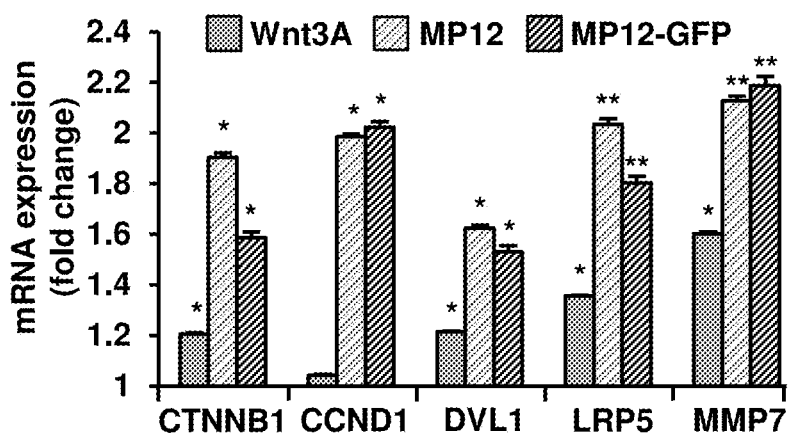

Next, the expression of endogenous Wnt/β-catenin target genes was examined in RVFV MP12 or RVFV MP12-GFP-infected cells. As a control, 50 ng/ml of Wnt3A was used to treat the cell cultures and induce expression of β-catenin regulated genes. Quantitative real-time RT-PCR (qRT-PCR) analysis was used to measure the mRNA expression levels of β-catenin, cyclin D1, Dvl, LRP5, or matrix metalloproteinase-7 (MMP7) after infection with RVFV MP12 or RVFV MP12-GFP (MOI=1) or after treatment with Wnt3A in A549 cells. The GFP reporter signal from RVFV MP12-GFP was readily observed between 5-6 hpi in this cell type, ensuring that viral mRNA transcription and translation occurred within this measurement time frame (see, e.g., Harmon B et al., "Identification of critical amino acids within the nucleoprotein of Tacaribe virus important for anti-interferon activity," *J. Biol. Chem.* 2013; 288(12):8702-11; and Islam M K et al., "High-throughput screening using a whole-cell virus replication reporter gene assay to identify inhibitory compounds against Rift Valley fever virus infection," *J. Biomol. Screen.* 2016; 21(4):354-62). RVFV MP12 and RVFV MP12-GFP infection led to significant upregulation of expression of all five genes, compared to mock-infected cells (FIG. 4D).

Figure 4E:
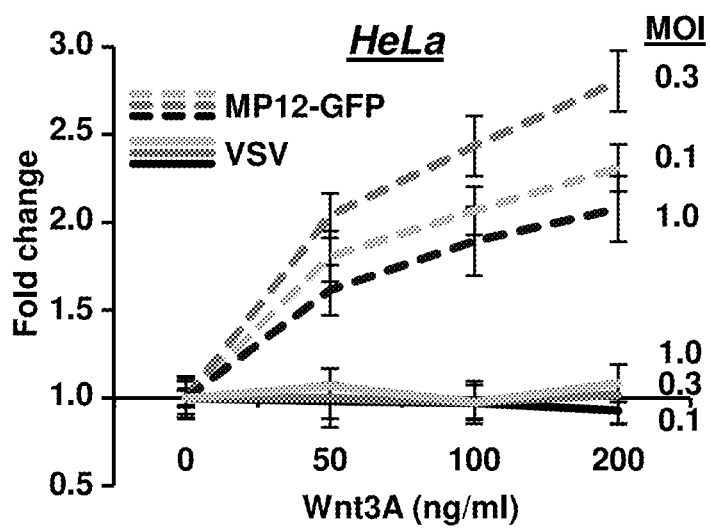
Figure 4F:
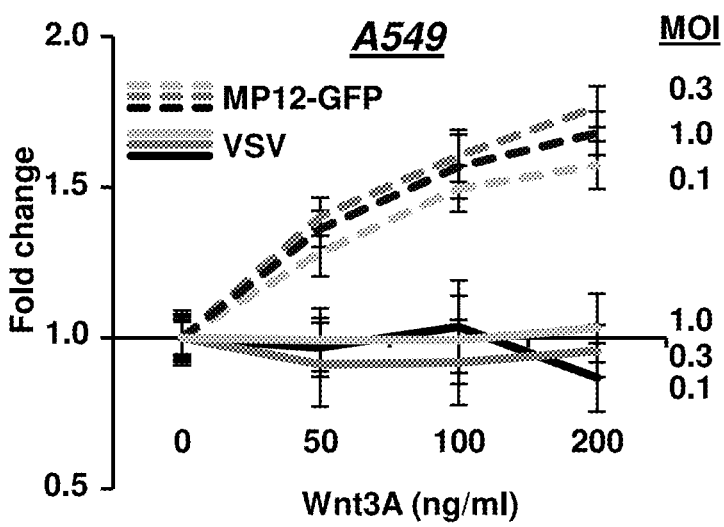
Figures 4G, 4H:
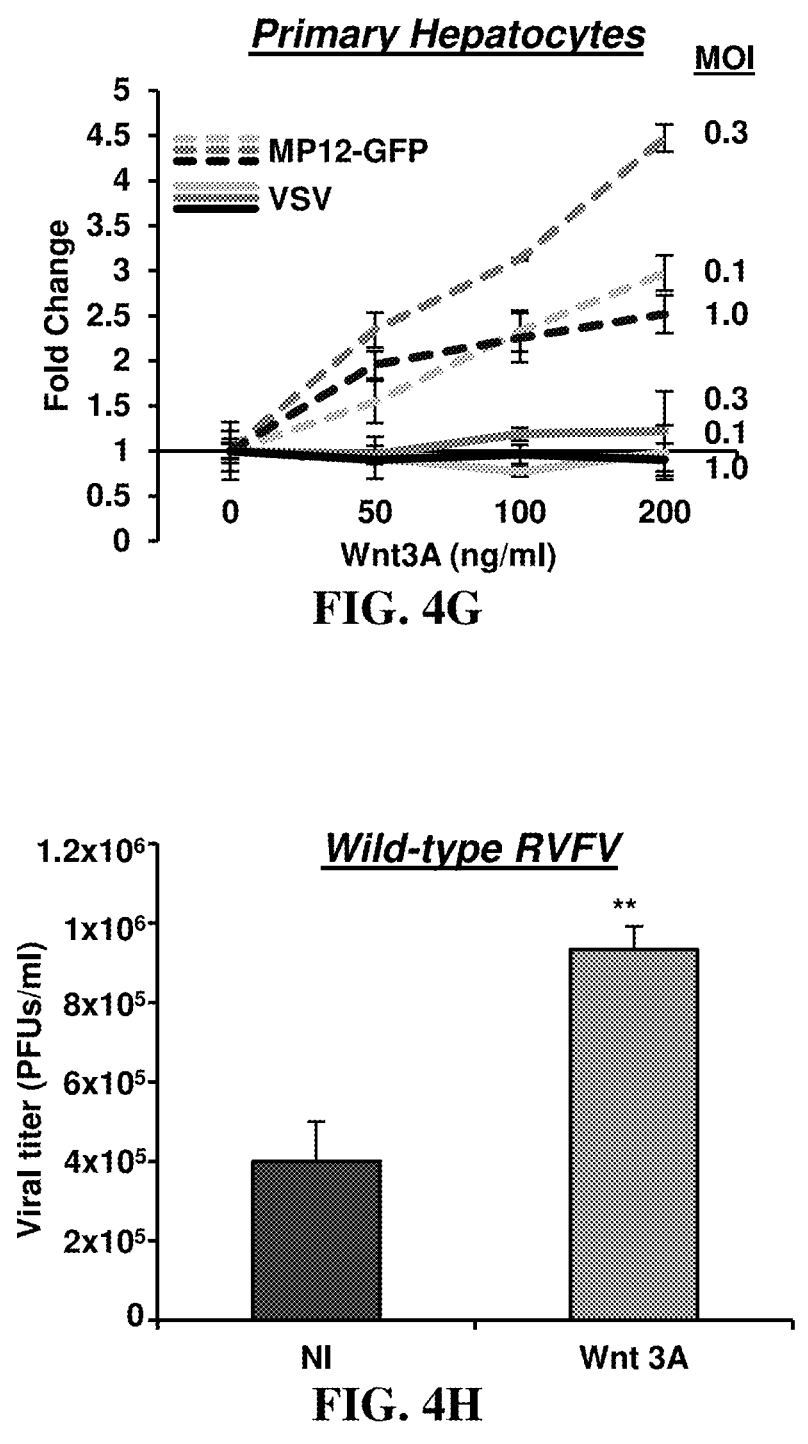

To determine if Wnt signaling positively regulates RVFV infection, we treated HeLa cells (FIG. 4E) and A549 cells (FIG. 4F) with increasing concentrations of Wnt3A prior to infection. In both HeLa and A549 cells, RVFV MP12-GFP viral infection was significantly enhanced compared to VSV when various infectious doses were used. To verify these results in the context of primary cell infection, primary hepatocytes were similarly treated with Wnt3A prior to infection with RVFV MP12-GFP or VSV (FIG. 4G). Hepatocytes are a prime in vivo target of RVFV infection in several animal models and are implicated in the more severe consequences of human RVFV infection that can lead to fatal hepatitis with hemorrhagic fever (see, e.g., Ross T M et al., "Animal models of Rift Valley fever virus infection," *Virus Res.* 2012; 163(2):417-23). We found that stimulation of primary hepatocytes with Wnt3A induced a greater than 4.5 fold increase in RVFV MP12-GFP (MOI=0.3) infection, while VSV infection remained unchanged using similar concentrations and infection conditions (FIG. 4G).

Finally, in order to determine whether or not pre-activation of Wnt signaling would enhance infection with fully virulent wild-type RVFV, HeLa cells were pretreated with Wnt3A for 20 hours prior to mock infection or infection with wild-type RVFV strain ZH-501 (MOI=0.1), and the extent of infection was quantified by plaque assay of the supernatants collected from virus-infected cells. Wild-type RVFV infection was enhanced in Wnt3A treated cells in comparison to untreated cells as demonstrated by a significant increase in the number of plaques (FIG. 4H). All together, these results demonstrate that RVFV infection induces Wnt/β-catenin transcriptional activity and that pre-activation of the Wnt pathway enhances RVFV infection. The results with wild-type RVFV and RVFV MP12 parallel those seen with RVFV MP12-GFP (ΔNSs), further strengthening the case for NSs-independent activation of the Wnt signaling pathway.

Example 5: Inhibitors of Wnt/β-Catenin Signaling Downstream of Membrane Receptor Complex Blocked RVFV Infection at a Post-Entry Step Wnt/β-catenin is a major signaling pathway with significant implications in a broad range of diseases including degenerative diseases, metabolic diseases, and cancer. As such, the Wnt/β-catenin signaling pathway has been a prime target for pharmacological research and development. Multiple antagonists and small molecule inhibitors have been identified that block at various points along the Wnt pathway, including those that target the membrane receptor complex, those that stabilize the DC, and those that interfere with activated β-catenin.

Figure 5A:
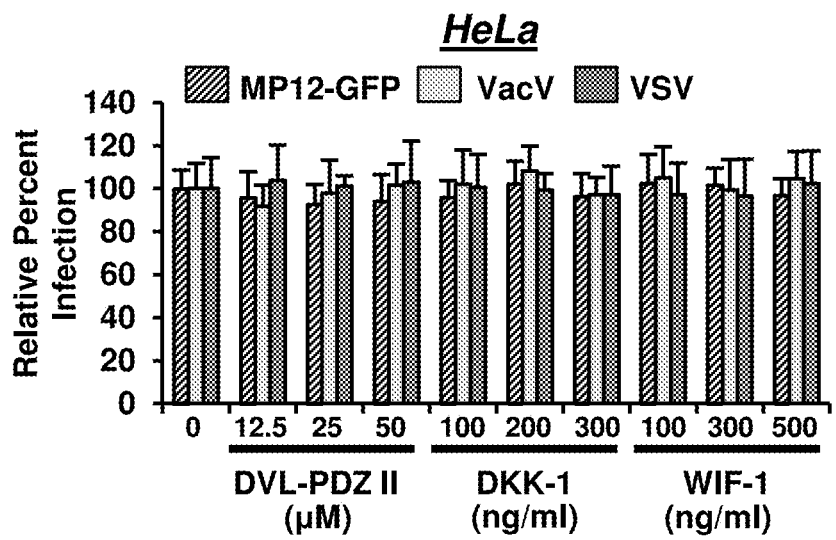

The recombinant proteins DKK-1, WIF-1, and the small molecule inhibitor Dvl-PDZ Domain inhibitor II (Dvl-PDZ II) block signaling from the Wnt receptor complex to the DC, so the DC remains intact and β-catenin is degraded. DKK-1 functions as an antagonist of canonical Wnt signaling by binding to co-receptors LRP5/6, preventing interaction of LRP5/6 with Wnt-FZD complexes. WIF-1 is a secreted protein that binds to Wnt ligands and inhibits their activity, while Dvl-PDZ II is a compound that targets the PDZ domain of Dvl to disrupt the interaction of Dvl with the FZD receptor, preventing sequestration of axin (see, e.g., Grandy D et al., "Discovery and characterization of a small molecule inhibitor of the PDZ domain of disheveled," *J. Biol. Chem.* 2009; 284(24):16256-63). Shown in FIG. 5A, treatment of HeLa cells with increasing concentrations of DKK-1, WIF-1 and Dvl-PDZ II was unable to reduce infection of RVFV MP12-GFP, VacV, or VSV. Similar results were seen in A549 cells (FIG. 6A).

Figure 5B:
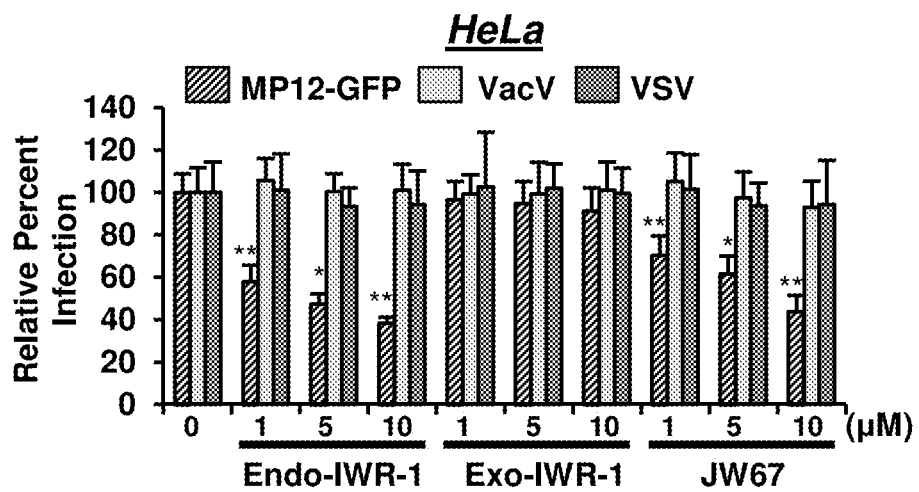
Figure 6B:
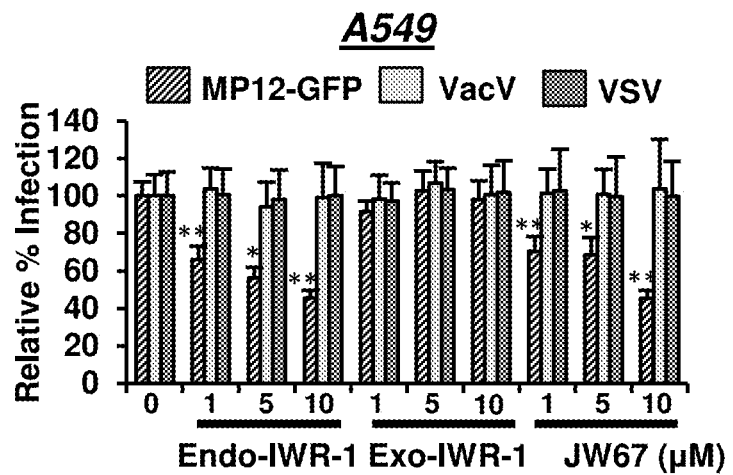

To determine the role of the DC in RVFV infection, cells were treated with Endo-IWR-1, Exo-IWR-1, and JW67. The tankyrase inhibitors (JW67 and Endo-IWR-1) prevent ADP-ribosylation-dependent axin degradation, resulting in stabilization of the DC and phosphorylation of β-catenin. Exo-IWR-1 is an inactive stereoisomer of Endo-IWR-1. Treatment of cells with these inhibitors reduced RVFV MP12-GFP infection in a dose-dependent manner, with a greater than 50% decrease in RVFV MP12-GFP infection (FIG. 5B). As expected, Exo-IWR-1 treatment did not inhibit RVFV MP12-GFP, and none of the inhibitors that stabilized the DC affected VacV or VSV infection, indicating the specificity of Endo-IWR-1 and JW67. Similar results were seen in A549 cells (FIG. 6B).

Figure 5C:
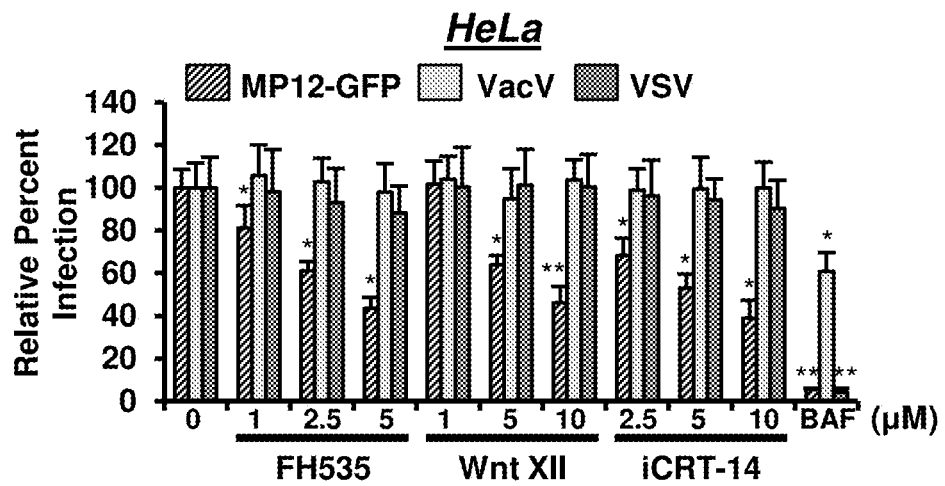
Figure 5D:
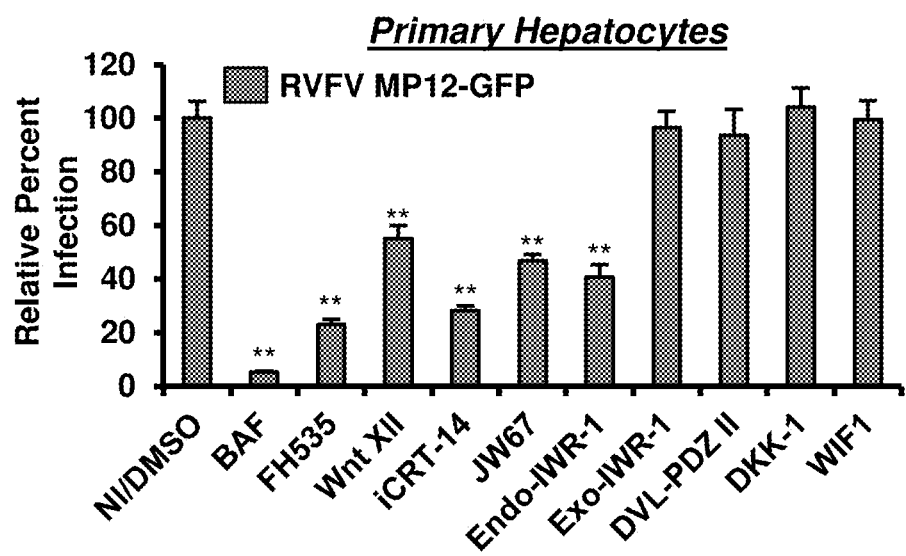
Figures 5E, 6A:
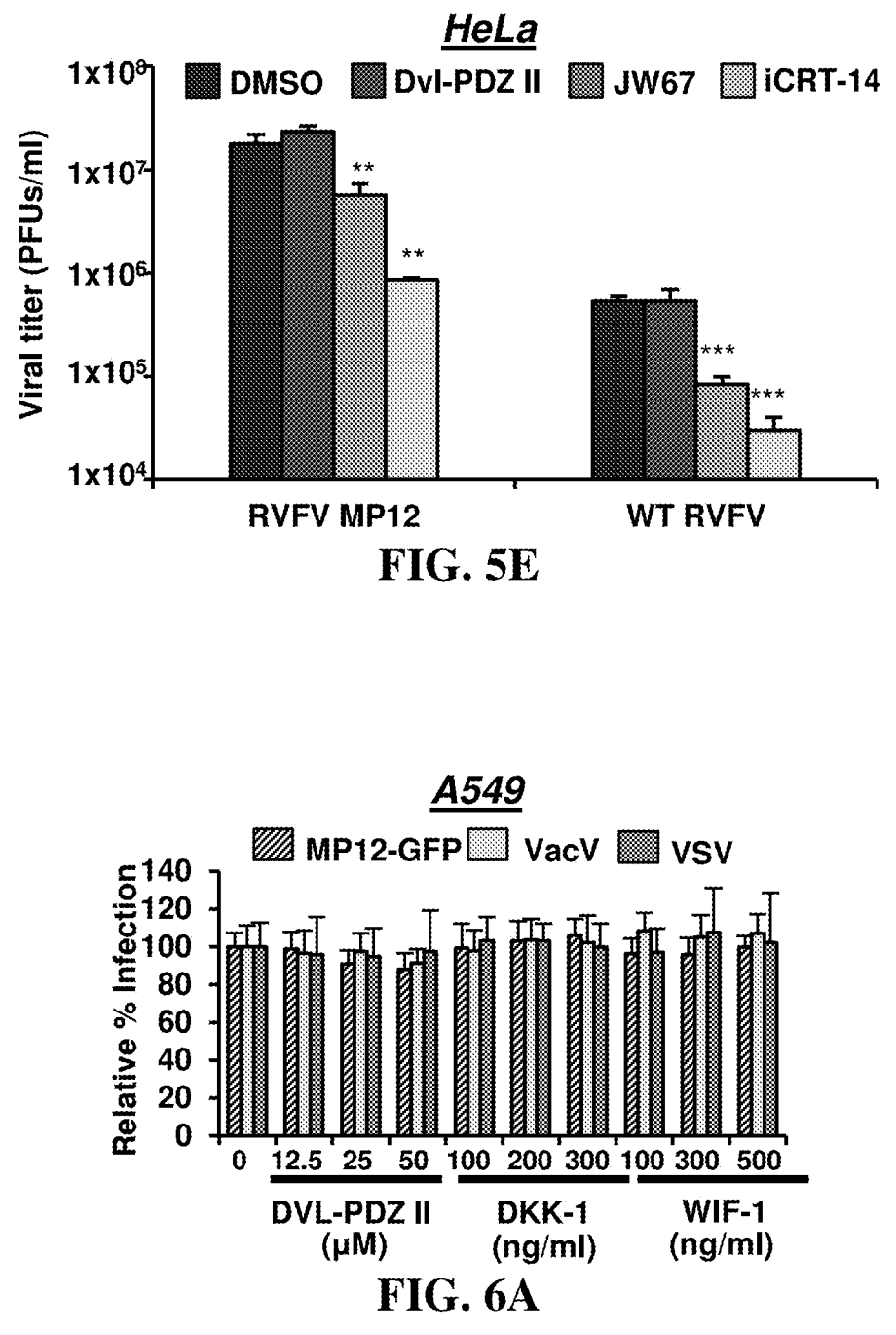
Figure 6C:
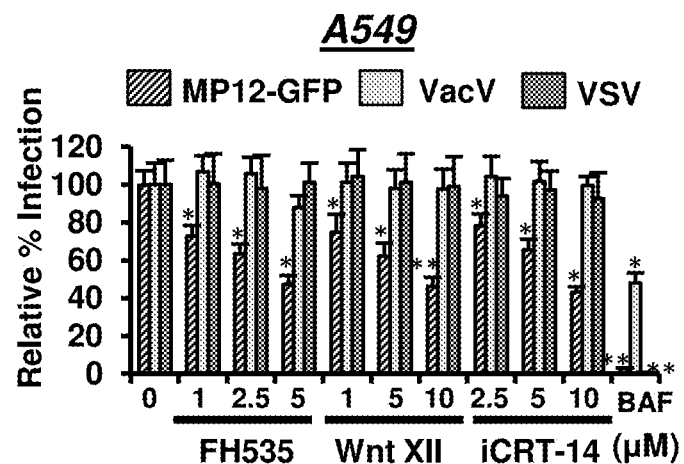

Additionally, small molecule inhibitors that interfere with the interaction of β-catenin with Tcf/Lef transcription factors (FH535, Wnt Pathway Inhibitor XII (Wnt XII), and iCRT-14) reduced RVFV MP12-GFP infection but did not diminish VacV or VSV infections in HeLa cells (FIG. 5C) and in A549 cells (FIG. 6C). The same Wnt signaling inhibitors that blocked infection in cell lines also reduced RVFV MP12-GFP infection in in vivo relevant primary hepatocytes (FIG. 5D).

Using the fluorescence-based plate reader assay that measures GFP fluorescence and cell viability, we were able to control for the specificity and efficacy of the small-molecule inhibitors by including VacV and VSV infection to exclude nonspecific effects. To look more directly at the effect of the Wnt inhibitors on viral growth, we measured viral titers of both wild-type RVFV and RVFV MP12 in the presence of inhibitors. When HeLa cells were treated with the Wnt inhibitors iCRT-14 and JW67, there was a significant decrease in RVFV MP12 and wild-type RVFV viral titers as measured by plaque assay (FIG. 5E). However, no change in viral titer was observed when cells were treated with the Wnt receptor antagonist Dvl-PDZ II (FIG. 5E, dark gray bar), as was observed with RVFV MP12-GFP.

Similar observations were made when flow cytometry was used to measure the percentage of inhibitor-treated cells infected with RVFV MP12 or RVFV MP12-GFP. Inhibitors that blocked Wnt signaling upstream of the DC had no effect on infection in HeLa cells (FIG. 7A) or in 293T cells (FIG. 7B-7C), while inhibitors that stabilized the DC or antagonized β-catenin interactions with transcription factors significantly reduced the percentage of cells infected with RVFV MP12 or RVFV MP12-GFP.

Figure 8A:
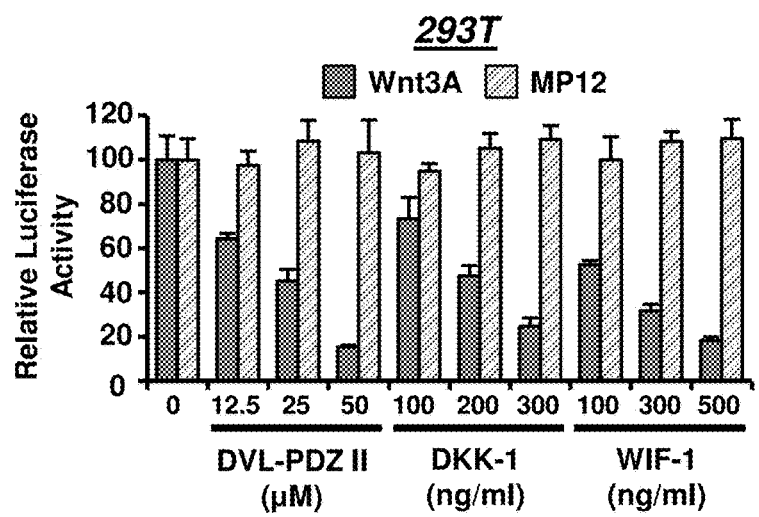
FIG. 8A-8C shows that RVFV-induced β-catenin transcriptional activity is blocked by inhibitors that act downstream of the membrane receptor complex. Provided are data for 293T cells that were transfected with TF and pcDNA3.1-GFP and treated with inhibitors that block at the Wnt receptor complex (FIG. 8A), inhibitors of the β-catenin destruction complex (DC) (FIG. 8B, in which Exo-IWR-1 is control), and inhibitors of activated β-catenin and nuclear import (FIG. 8C). At 18 hpt, cells were treated with the indicated inhibitors for 1 h. The inhibitors were also present during the 4.5 h incubation with RVFV MP12 (MOI=3) or 20 h incubation with Wnt3A (100 ng/ml). Luciferase activity was measured and normalized to GFP expression; and relative luciferase activity was determined by taking untreated (NI) or DMSO-treated and infected samples as 100%. Three independent experiments were performed in triplicate. Data are presented as mean±S.D.

To validate the efficacy and specificity of these Wnt membrane complex inhibitors at the concentrations used to characterize infection, DKK-1, WIF-1, and Dvl-PDZ II were used to treat 293T cells transfected with TF and stimulated with Wnt3A for 20 hours (gray bars) or RVFV MP12 for 5 hours (diagonal shaded bars) (FIG. 8A). Treatment of 293T cells with these inhibitors resulted in a dose-dependent reduction of Wnt3A-induced β-catenin luc reporter expression. Wnt membrane complex inhibitors had no effect on RVFV MP12-induced β-catenin transcriptional activity (FIG. 8A).

Figure 8B:
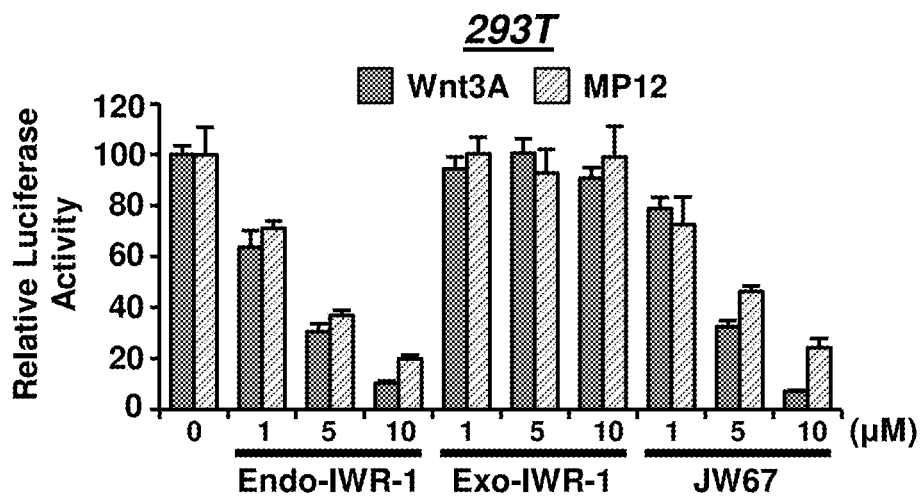
Figure 8C:
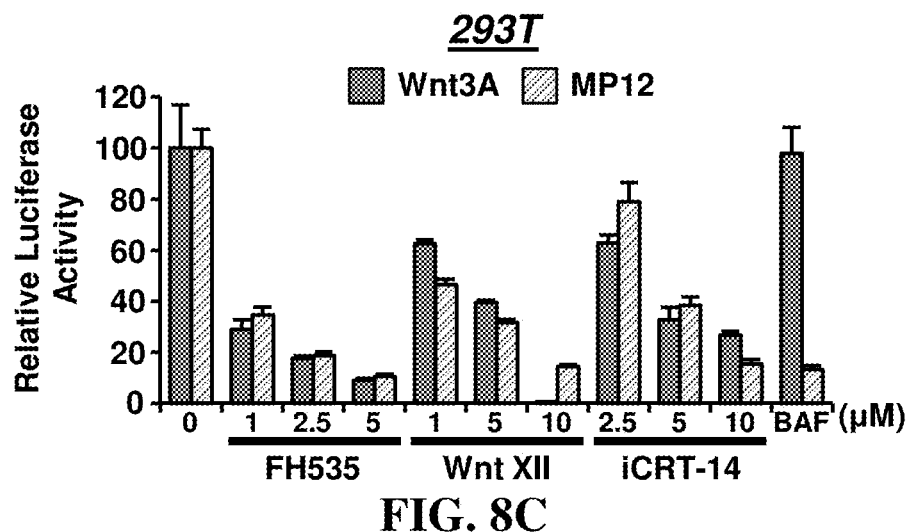

In contrast, Wnt inhibitors that stabilized the DC (Endo-IWR-1 or JW67) and that interfered with the interaction of β-catenin with Tcf/Lef transcription factors (FH535, Wnt XII, or iCRT-14) inhibited RVFV MP12-induced and Wnt3A-induced β-catenin reporter activity in 293T cells in a dose-dependent manner (FIG. 8B-8C). The dose-dependent decrease in RVFV MP12-induced β-catenin reporter activity observed with these inhibitors correlated with their effect on RVFV replication, suggesting that the effect of these inhibitors on infection was specific to inhibition of Wnt/β-catenin signaling. These data indicate that the mechanism of RVFV-induced activation is downstream of the Wnt receptor complex, but can be blocked by inhibitors that stabilize the DC and/or inhibitors that interfere with β-catenin-dependent transcriptional activation. Interestingly, Bafilomycin A (BAF), an inhibitor of pH-dependent endocytosis, blocked RVFV MP12-induced β-catenin reporter activity, suggesting that RVFV-mediated induction occurs after virus entry (FIG. 8C).

To determine what stage of RVFV infection was dependent on Wnt/β-catenin signaling, we performed time-of-addition experiments. In our previous studies, we found that binding and entry of RVFV MP12-GFP takes approximately one hour in HeLa cells because treatment with inhibitors of endosomal acidification such as ammonium chloride ($NH_4Cl$) 1 hpi no longer blocked infection (see, e.g., Harmon B et al., *J. Virol.* 2012; 86(23):12954-70; Filone C M et al., "Rift Valley fever virus infection of human cells and insect hosts is promoted by protein kinase C epsilon," *PLoS One* 2010; 5(11):e15483 (12 pp.); and Filone C M et al., "Development and characterization of a Rift Valley fever virus cell-cell fusion assay using alphavirus replicon vectors," *Virology* 2006; 356(1-2): 155-64). Therefore, agents that target a post-entry stage should still inhibit infection when treatments are added 1 hpi.

Figure 9A:
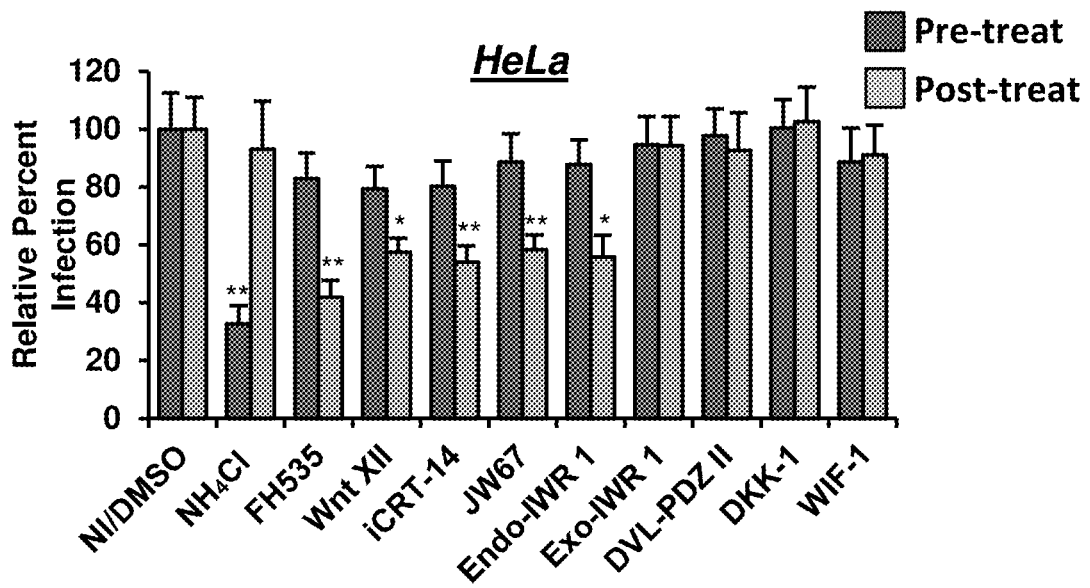
FIG. 9A-9B shows that Wnt signaling inhibitors block RVFV infection at a post-entry step. Provided are data for HeLa cells (FIG. 9A) and A549 cells (FIG. 9B), which were pretreated with no inhibitor (NI)/50 µM DMSO, 50 mM NH₄Cl, 5 µM FH535, 10 µM Wnt XII, 10 µM iCRT-14, 10 µM JW67, 10 µM Endo-IWR-1, 10 µM Exo-IWR-1, 50 µM Dvl-PDZ II, 300 ng/ml of DKK-1, or 500 ng/ml of WIF-1 for 1 h prior to and during the 3 h infection with RVFV MP12-GFP (MOI=1). Inhibitors were removed after the 3 h incubation, and cells were incubated in complete medium alone overnight (pre-treat, dark gray bars). For post-treatment condition, untreated cells were incubated with RVFV MP12-GFP (MOI=1) for 1 h, washed with PBS to remove unbound virus, and then incubated with inhibitors in complete medium overnight (light gray bars). The percentage of infection was determined by taking NI/DMSO-treated and infected samples as 100% infected. Three independent experiments were performed in triplicate. Data are presented as mean±S.D. (**, P<0.01; *, P<0.05).
Figure 9B:
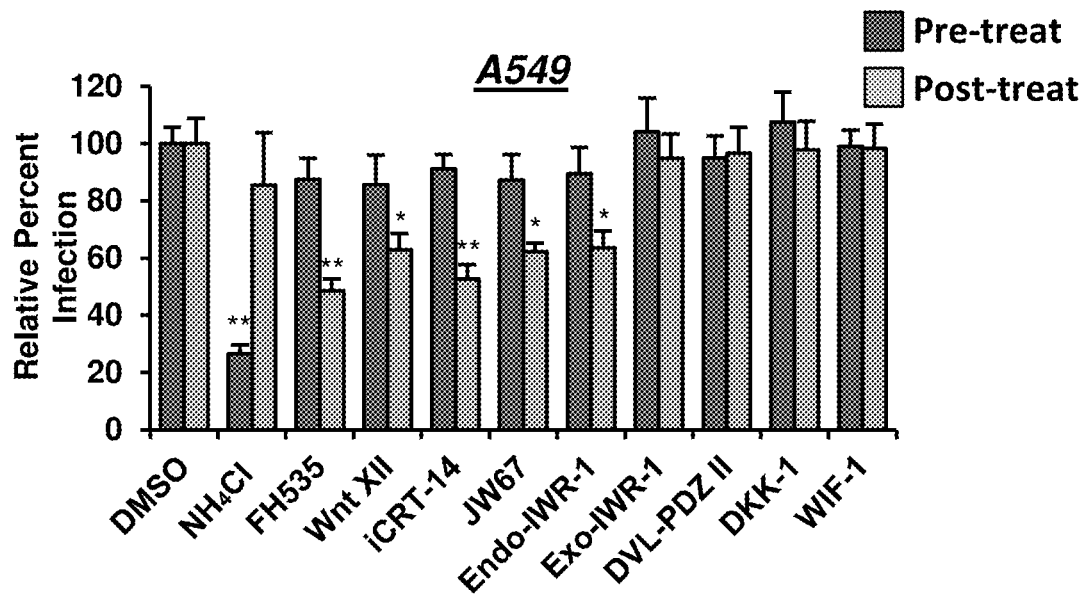

Those inhibitors that stabilize the DC (Endo-IWR-1 and JW67) and those that interfere with activated β-catenin (FH535, Wnt XII and iCRT-14) were shown to significantly inhibit RVFV MP12-GFP infection in HeLa cells (FIG. 9A) or in A549 cells (FIG. 9B) when they were added 1 hpi and were present during the entire infection cycle. These inhibitors had little to no effect on infection when they were present 1 hour prior to and during initial infection but were removed after 3 hours. As expected, inhibitors that antagonize the Wnt membrane receptor complex (DKK-1, WIF-1, Dvl-PDZ II) and the control Exo-IWR-1 had no effect on RVFV MP12-GFP infection when cells were either pre-treated or treated 1 hpi. In all, these data demonstrated that inhibitors that block Wnt signaling downstream of the membrane receptor complex inhibit RVFV infection at a post-entry step.

Figures 10A, 10B:
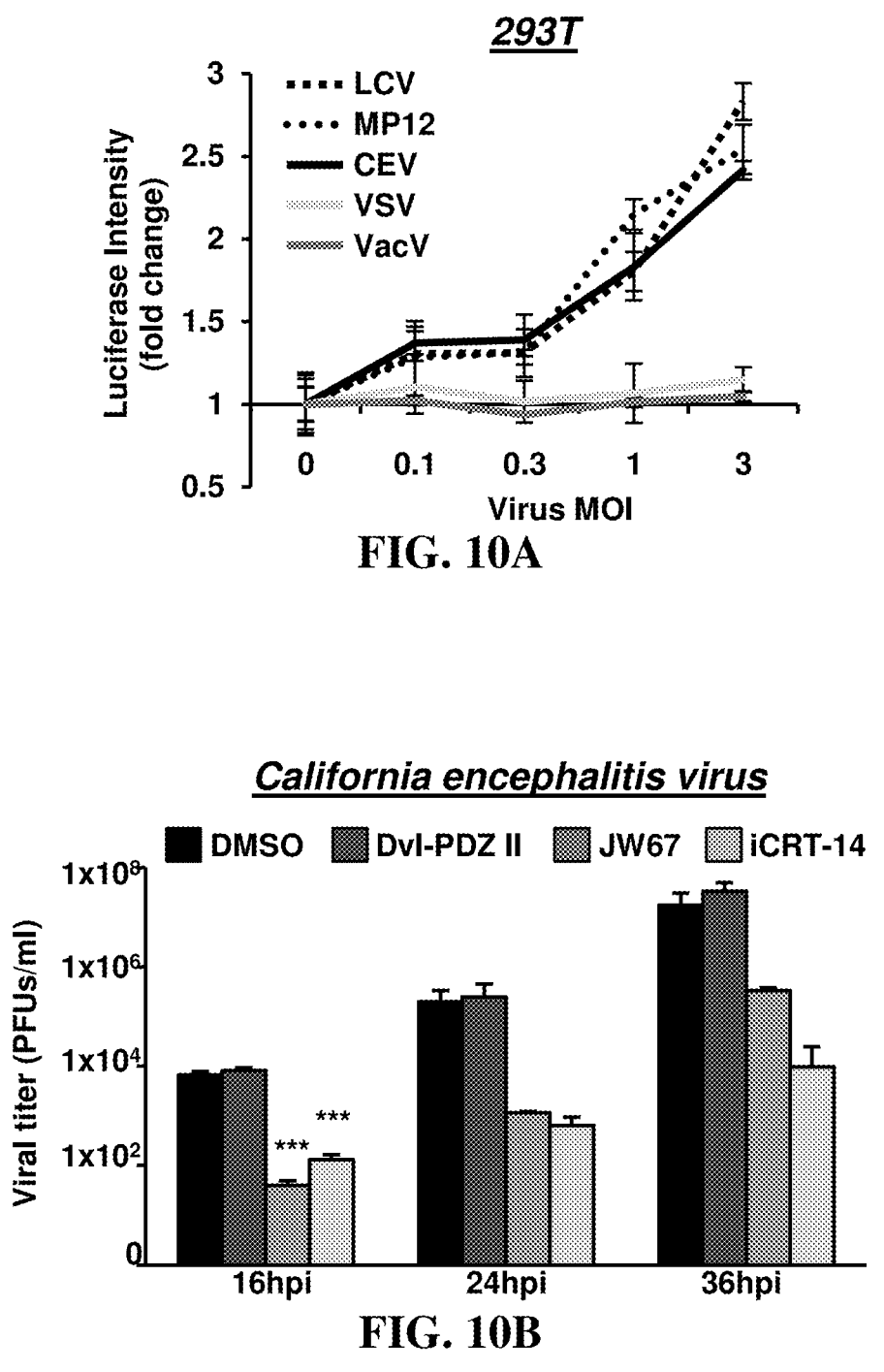
Figures 10C, 11:
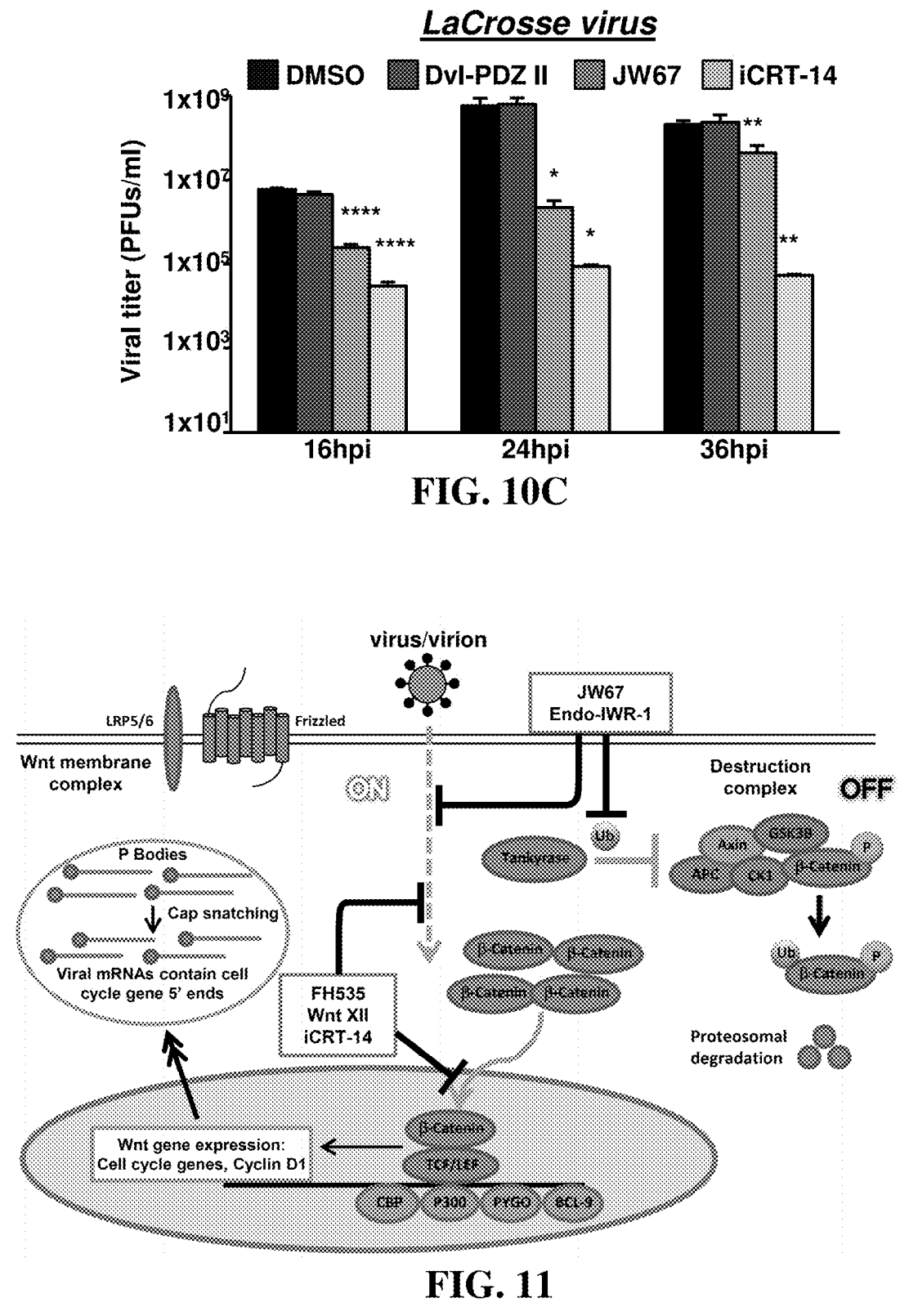

Example 6: Distantly Related Bunyaviruses Induce Wnt/β-Catenin Signaling Upon Infection and are Impeded by Wnt Signaling Inhibitors Although RVFV, VSV, and VacV all replicate in the cytoplasm, they do so through distinct mechanisms. Hallmark features of virus replication are typically conserved within virus families. To examine whether distantly related bunyaviruses also induce Wnt/β-catenin signaling upon infection, we performed β-catenin luc reporter experiments in 293T cells transiently transfected with TF for 18 hours and subsequently infected with California Encephalitis virus (CEV) or La Crosse virus (LCV). In FIG. 10A, infections with CEV or LCV were shown to promote β-catenin reporter activation across a range of infectious doses to levels comparable to RVFV MP12-infected cells, while VSV and VacV infections did not induce Wnt/β-catenin signaling. Furthermore, inhibitors of Wnt/β-catenin signaling that reduced RVFV MP12-GFP, RVFV MP12, and wild-type RVFV infection (FIGS. 5A-5E and FIGS. 7A-7C), also reduced CEV and LCV infections as measured by plaque assay in HeLa cells (FIG. 10B-10C). Greater than a 50% reduction in CEV and LCV infections was exhibited when HeLa cells were treated with 50 μM JW67 or iCRT-14, whereas treatment of cells with 50 μM Dvl-PDZ II had no effect on viral titers, replicating what is seen with RVFV. These results indicated a conserved bunyaviral replication mechanism involving Wnt signaling.

Example 7: Systems Approaches to Understanding and Controlling the Wnt Signaling Pathway High-throughput genome-wide RNAi is a powerful tool for functional genomics with the capacity to comprehensively analyze host-pathogen interactions (see, e.g., Schudel B R et al., "Microfluidic platforms for RNA interference screening of virus-host interactions," *Lab Chip* 2013; 13(5): 811-7; and Cherry S, "What have RNAi screens taught us about viral-host interactions?," *Curr. Opin. Microbiol.* 2009; 12(4):446-52). The promise of this systems approach is not only to gain a better understanding of virus-host interactions but also for the discovery of new therapeutic targets. This technology is not without inherent problems and pitfalls, such as off-target effects and insufficient knockdown that may lead to false positives/negative results. Nonetheless, analysis of the gene list as ranked functional clusters has been a successful method in gaining reproducibility between screens and providing direction for detailed cell biology investigations (see, e.g., Bushman F D et al., "Host cell factors in HIV replication: meta-analysis of genome-wide studies," *PLoS Pathog.* 2009; 5(5):e1000437 (12 pp.); and Mercer J et al., "RNAi screening reveals proteasome- and Cullin3-dependent stages in vaccinia virus infection," *Cell Rep.* 2012; 2(4):1036-47). Therefore, to support the value of our final gene hit list, we validated our RNAi screening results through a thorough examination of the top ranking cellular pathways analyzed by various bioinformatics methods, instead of the validation of individual gene hits.

We used a panoply of Wnt/β-catenin signaling activation assays to demonstrate that RVFV activates the canonical Wnt signaling pathway. We demonstrated that a RVFV infection activates Wnt signaling in multiple cell types optimally at 5 hpi using a β-catenin reporter assay, increases the level of active β-catenin protein by about 3-fold as compared to mock infected controls (FIG. 4C), and increases mRNA expression of Wnt/β-catenin responsive genes such as cyclin D1 (CCND1) by about 2 fold as compared to controls (FIG. 4D). Using cellular perturbation assays, we showed that RNAi-induced silencing of β-catenin expression reduced RVFV infection in multiple cell types (FIGS. 3A-3B) and that chemical inhibition of Wnt signaling at or downstream of the DC reduced RVFV infection at a post-entry step (FIGS. 5A-5E and FIGS. 9A-9B). Our data demonstrating that diverse bunyaviruses induced β-catenin reporter activity and that fully virulent wild-type RVFV, as well as attenuated strains of RVFV, LCV, and CEV, required activation of Wnt/β-catenin for productive infection suggests that activation of canonical Wnt signaling impacts replication of bunyaviruses as a family (FIG. 10A-10C).

Wnt/β-catenin signaling controls many aspects of cell behavior throughout development and in adults. One of its best-known and cancer-relevant functions is to stimulate cell proliferation. A growing body of work suggests that the cell cycle and Wnt signaling pathways are directly linked (see, e.g., Davidson G et al., "Emerging links between CDK cell cycle regulators and Wnt signaling," *Trends Cell. Biol.* 2010; 20(8):453-60). Interestingly, a recent study by Hopkins K C et al., (*Genes Dev.* 2013; 27(13):1511-25) revealed a preference for particular stages of the cell cycle for RVFV replication, as cells arrested in late S/early G2 phase, but not at G1 phase, enhanced RVFV replication. While it has not been previously reported that RVFV infection can influence shifts to preferred cell cycle stages, the Hopkins et al. study indicated that certain cell cycle stages are particularly abundant in host mRNAs available to prime bunyaviral gene transcription through a cap snatching mechanism (see, e.g., Hopkins K et al., "Bunyaviral cap-snatching vs. decapping: recycling cell cycle mRNAs," *Cell Cycle* 2013; 12(24): 3711-2). Bunyaviruses and other segmented negative stranded RNA viruses (arenaviruses and orthomyxoviruses) cleave off the 5'-end of cellular mRNAs that includes the 5'-7mG cap and 10-18 nucleotides of host mRNAs and use this fragment as a primer for viral mRNA synthesis. When the 5'-ends of RVFV mRNAs were sequenced, it was demonstrated that RVFV selectively snatches cell cycle related cellular mRNAs.

Linking these studies together with our results, it is possible that bunyaviruses activate the Wnt signaling pathway in order to induce both cell cycle shifts and abundant endogenous pools of cell cycle related mRNAs available for priming bunyaviral gene transcription (FIG. 11). It is also interesting to note that cell cycle and cyclin related genes were among the top functional clusters identified using bioinformatics analysis of our genome-wide RNAi screening results (Tables I, II, and IIIA-IIIT). This proposed mechanism also might help explain the negative results we found with VacV and VSV. Like many other DNA and RNA viruses that replicate in the cytoplasm, VacV and VSV both encode their own capping enzymes and therefore do not need to increase the pool of host mRNAs available for cap snatching.

It has been demonstrated that viral proteins can regulate Wnt/β-catenin signaling through direct and indirect interactions with mediators of the Wnt pathway. The HCV core protein activates Wnt/β-catenin signaling at the level of the receptor complex since a soluble Fzd molecule blocks core-stimulated cell growth (see, e.g., Liu J et al., "Hepatitis C virus core protein activates Wnt/β-catenin signaling through multiple regulation of upstream molecules in the SMMC-7721 cell line," *Arch. Virol.* 2011; 156(6):1013-23). KSHV encoded latency-associated nuclear antigen (LANA) prevents β-catenin phosphorylation and degradation by interacting with the DC kinase GSK-3 in the nucleus and preventing its export to the cytoplasm (see, e.g., Fujimuro M et al., "Regulation of the interaction between glycogen synthase kinase 3 and the Kaposi's sarcoma-associated herpesvirus latency-associated nuclear antigen," *J. Virol.* 2005; 79(16):10429-41). The HBV viral regulatory protein HBx suppresses GSK-3 activity via the activation of Src kinase (see, e.g., Cha M Y et al., "Hepatitis B virus X protein is essential for the activation of Wnt/β-catenin signaling in hepatoma cells," Hepatology 2004; 39(6):1683-93). Our results with RVFV MP12-mediated activation of Wnt/β-catenin signaling, as measured by the β-catenin reporter assay and upregulation of mRNA expression of Wnt/β-catenin responsive genes, showed that activation occurs early in infection (4-6 hpi) and is essentially turned off by 8 hpi (data not shown).

Since the RVFV nucleoprotein (N) is the most abundant viral protein early in cell infection and is involved in gene transcription, genome replication, cap-snatching, and translation (see, e.g., Le May N et al., "The N terminus of Rift Valley fever virus nucleoprotein is essential for dimerization," *J. Virol.* 2005; 79(18):11974-80; Cheng E et al., "Signatures of host mRNA 5' terminus for efficient hantavirus cap snatching," *J. Virol.* 2012; 86(10):10173-85; and Guu T S et al., "Bunyavirus: structure and replication," *Adv. Exp. Med. Biol.* 2012; 726:245-66), without wishing to be limited by mechanism, we hypothesize it may be a determinant of Wnt/β-catenin signaling activation during infection. In addition, the amino acid sequence of N is identical between RVFV MP12, RVFV MP12-GFP and wild-type RVFV, whereas the other viral protein transcribed early (during primary transcription) in infection, NSs, is not expressed in RVFV MP12-GFP, which was fully functional in Wnt/β-catenin signaling activation. Moreover, a recent study reported that the RVFV ZH-548 ΔNSs strain induced significant upregulation of mRNA expression of genes related to the Wnt/β-catenin signaling pathway, whereas at 8 hpi they did not observe the same upregulation with wild-type RVFV ZH-548 (see, e.g., Marcato V et al., "β-catenin upregulates the constitutive and virus-induced transcriptional capacity of the interferon beta promoter through T-cell factor binding sites," *Mol. Cell. Biol.* 2015; 36(1):13-29). Based on our results with RVFV MP12-GFP, RVFV MP12, and wild-type RVFV as well as the findings in Marcato et al., it is likely that NSs is not required for Wnt/β-catenin signaling activation but may be responsible for repressing this signal at 8 hpi, as a result of general transcriptional shutoff (see, e.g., Ikegami T et al., "The pathogenesis of Rift Valley fever," *Viruses* 2011; 3(5):493-519). While we found that inhibitors downstream of the Wnt membrane receptor complex reduce RVFV infection, we cannot distinguish between direct or indirect mechanisms of Wnt activation.

RVFV-mediated activation of β-catenin seems to occur downstream of receptor activation but is blocked by stabilization of the DC scaffolding protein. Besides binding to other viral proteins, RVFV N also binds to the 5'-ends of host mRNAs to initiate cap-snatching, and RVFV N localizes to processing (P) bodies where cellular RNA degradation machinery is compartmentalized. Further studies could resolve whether RVFV N binding events in P bodies, where cap snatching is thought to occur, or whether prior viral-host interaction events in regions where Wnt signaling components are localized is the trigger for Wnt signaling activation.

Large scale RNAi screening is a promising tool for comprehensive analysis of virus-host interactions and therapeutic target identification. To the latter point, several preclinical therapeutic agents specifically targeting the Wnt pathway have been described, and some have entered clinical trials for the treatment of a variety of cancers. PRI-724 from Prism Pharma disrupts the interaction between β-catenin and CREB-binding protein and is being studied for the treatment of solid tumors and myeloid malignancies in Phase I/II clinical trials (see, e.g., Lenz H J et al., "Safely targeting cancer stem cells via selective catenin coactivator antagonism," *Cancer Sci.* 2014; 105(9): 1087-92). Another cancer drug called OMP-54F28 (FZD8-Fc) is an antagonist of the Wnt pathway and results from a phase I trials were recently described (see, e.g., Le P N et al., "Targeting the Wnt pathway in human cancers: therapeutic targeting with a focus on OMP-54F28," *Pharmacol. Ther.* 2015; 146:1-11). Preclinical studies with tankyrase inhibitors JW55 (Tocris Bioscience) and XAV939 (Novartis Pharmaceuticals) demonstrated efficacy in cellular models of cancer survival (see, e.g., Waaler J et al., "A novel tankyrase inhibitor decreases canonical Wnt signaling in colon carcinoma cells and reduces tumor growth in conditional APC mutant mice," *Cancer Res.* 2012; 72(11):2822-32). In our study, the tankyrase inhibitors (Endo-IWR-1 and JW67) inhibited RVFV MP12-GFP infection by greater than 50% in RVFV disease-relevant primary human hepatocytes (FIG. 5D), and JW67 significantly reduced infection of cells with wild-type RVFV, LCV, and CEV. As current and new Wnt inhibitors begin to move through safety trials, there is potential for one of these to be FDA-approved, opening the door for an alternative use as an anti-RVFV therapeutic.

In all, we identified a role for canonical Wnt/β-catenin signaling during infection with diverse bunyaviruses. These studies supplement our knowledge of the fundamental mechanisms of bunyavirus gene transcription and replication and provide new avenues for countermeasure development against pathogenic bunyaviruses. We also provide the list of genome-wide RNAi screening results in order to supplement current databases of other viral-RNAi screening results and to provide future direction for detailed pathway investigation from other top ranked functional clusters not characterized herein.

OTHER EMBODIMENTS

All publications, patents, and patent applications, including U.S. Provisional Application No. 62/197,341, filed Jul. 27, 2015, mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of treating a viral infection in a subject, the method comprising:
   administering both a tankyrase inhibitor and a transcriptional activity inhibitor to the subject in an effective amount to treat the viral infection by inhibiting Wnt/β-catenin signaling after cellular entry by a virus, wherein the tankyrase inhibitor and the transcriptional activity inhibitor are administered after exposure to the virus causing the viral infection and administered at least one hour post-infection,
   wherein the viral infection comprises an infection from a bunyavirus,
   wherein the tankyrase inhibitor is selected from the group consisting of JW67 (trispiro[3H-indole-3,2'-[1.3]dioxane-5',5"-[1,3]dioxane-2",3'"-[3H]indole]-2,2'"(1H, 1'"H)-dione); JW55 (N-[4-[[4-(4-25 methoxyphenyl) oxan-4-yl]methylcarbamoyl]phenyl]furan-2-carboxamide); JW74 (4-[4-(4-methoxyphenyl)-5-[[[3-(4-methylphenyl)-1,2,4-oxadiazol-5-yl]methyl]thio]-4H-1,2,4-triazol-3-yl]-pyridine): Endo-IWR-1 (4-[(3aR,4S,7R,7aS)-1,3-dioxo-1,3,3a,4,7,7a-hexahydro-2H-4,7-methanoisoindol-2-yl]-N-(quinolin-8-yl) benzamide); and XAV939 (2-[4-(trifluoromethyl) phenyl]-1,5,7,8-tetrahydrothiopyrano[4,3-d]pyrimidin-4-one), or a salt thereof, and
   wherein the transcriptional activity inhibitor is selected from the group consisting of Wnt Pathway Inhibitor XII ((E)-4-(2,6-difluorostyryl)-N,N-dimethylanilin); FH535 (2,5-dichloro-N-(2-methyl-4-nitrophenyl)benzenesulfonamide); iCRT3 (2-[[[2-(4-ethylphenyl)-5-methyl-4-oxazolyl]methyl]thio]-N-(2-phenylethyl)acetamide); iCRT5 (4-[(5Z)-5-[(3,4-dimethoxyphenyl) methylidene]-4-oxo-2-sulfanylidene-1,3-thiazolidin-3-yl]butanoic acid); and iCRT14 (iCRT-14 or (5Z)-5-[(2, 5-dimethyl-1-pyridin-3-ylpyrrol-3-yl)methylidene]-3-phenyl-1,3-thiazolidine-2,4-dione), or a salt thereof.

2. The method of claim 1, wherein the viral infection comprises an infection from a segmented RNA virus.

3. The method of claim 1, wherein the viral infection comprises an infection from a Rift Valley fever virus, hantavirus, California encephalitis virus, Crimean-Congo hemorrhagic fever virus, or La Crosse virus.

4. The method of claim 1, wherein the viral infection comprises an infection from an arthropod-borne virus.

5. The method of claim 1, wherein the tankyrase inhibitor and the transcriptional activity inhibitor are administered about one hour after exposure to a virus causing the viral infection.

6. The method of claim 1, wherein the tankyrase inhibitor and the transcriptional activity inhibitor are administered is administered prior to eight hours post-infection.

7. The method of claim 1, wherein the tankyrase inhibitor and the transcriptional activity inhibitor are administered of from about four to six hours post-infection.

8. The method of claim 1, wherein the viral infection comprises an infection from a virus of a Phlebovirus genus.

9. The method of claim 1, wherein the subject is a human subject.

10. The method of claim 1, wherein the tankyrase inhibitor is JW67 and the transcriptional activity inhibitor is iCRT14.

11. A method of treating a viral infection in a subject, the method comprising:
    administering both a tankyrase inhibitor and a transcriptional activity inhibitor to the subject in an effective amount to treat the viral infection by inhibiting Wnt/β-catenin signaling after cellular entry by a virus, wherein the tankyrase inhibitor and the transcriptional activity inhibitor are administered after exposure to the virus causing the viral infection and administered at least one hour post-infection, and wherein the viral infection comprises an infection from a bunyavirus; and
    determining a decreased viral titer of the bunyavirus from a sample obtained from the subject after administering the tankyrase inhibitor and the transcriptional activity inhibitor,
    wherein the tankyrase inhibitor is selected from the group consisting of JW67 (trispiro[3H-indole-3,2'-[1,3]dioxane-5',5"-[1,3]dioxane-2",3'"-[3H]indole]-2,2'"(1H, 1'"H)-dione); JW55 (N-[4-[[4-(4-methoxyphenyl) oxan-4-yl]methylcarbamoyl]phenyl]furan-2-carboxamide); JW74 (4-[4-(4-methoxyphenyl)-5-[[[3-

(4-methylphenyl)-1,2,4-oxadiazol-5-yl]methyl]thio]-4H-1,2,4-triazol-3-yl]-pyridine): Endo-IWR-1 (4-[(3aR,4S,7R,7aS)-1,3-dioxo-1,3,3a,4,7,7a-hexahydro-2H-4,7-methanoisoindol-2-yl]-N-(quinolin-8-yl) benzamide); and XAV939 (2-[4-(trifluoromethyl) phenyl]-1,5,7,8-tetrahydrothiopyrano[4,3-d]pyrimidin-4-one), or a salt thereof, and wherein the transcriptional activity inhibitor is selected from the group consisting of Wnt Pathway Inhibitor XII ((E)-4-(2,6-difluorostyryl)-N,N-dimethylaniline); FH535 (2,5-dichloro-N-(2-methyl-4-nitrophenyl)benzenesulfonamide); iCRT3 (2-[[[2-(4-ethylphenyl)-5-methyl-4-oxazolyl]methyl]thio]-N-(2-phenylethyl)acetamide); iCRT5 (4-[(5Z)-5-[(3,4-dimethoxyphenyl) methylidene]-4-oxo-2-sulfanylidene 1,3-thiazolidin-3-yl]butanoic acid); and iCRT14 (iCRT-14 or (5Z)-5-[(2,5-dimethyl-1-pyridin-3-ylpyrrol-3-yl)methylidene]-3-phenyl-1,3-thiazolidine-2,4-dione), or a salt thereof.

12. The method of claim 11, wherein the tankyrase inhibitor is JW67 and the transcriptional activity inhibitor is iCRT14.

13. A method of treating a viral infection in a subject, the method comprising:

administering a formulation comprising both a tankyrase inhibitor and a transcriptional activity inhibitor to the subject in an effective amount to treat the viral infection by inhibiting Wnt/β-catenin signaling after cellular entry by a virus, wherein the formulation is administered after exposure to the virus causing the viral infection and administered at least one hour post-infection, wherein the viral infection comprises an infection from a bunyavirus, wherein the tankyrase inhibitor is selected from the group consisting of JW67 (trispiro[3H-indole-3,2'-[1,3]dioxane-5',5''-[1,3]dioxane-2'',3'''-[3H]indole]-2,2'''(1H, 1'''H)-dione); JW55 (N-[4-[[4-(4-25 methoxyphenyl) oxan-4-yl]methylcarbamoyl]phenyl]furan-2-carboxamide); JW74 (4-[4-(4-methoxyphenyl)-5-[[[3-(4-methylphenyl)-1,2,4-oxadiazol-5-yl]methyl]thio]-4H-1,2,4-triazol-3-yl]-pyridine): Endo-IWR-1 (4-[(3aR,4S,7R,7aS)-1,3-dioxo-1,3,3a,4,7,7a-hexahydro-2H-4,7-methanoisoindol-2-yl]-N-(quinolin-8-yl) benzamide); and XAV939 (2-[4-(trifluoromethyl) phenyl]-1,5,7,8-tetrahydrothiopyrano[4,3-d]pyrimidin-4-one), or a salt thereof, and wherein the transcriptional activity inhibitor is selected from the group consisting of Wnt Pathway Inhibitor XII ((E)-4-(2,6-difluorostyryl)-N,N-dimethylanilin); FH535 (2,5-dichloro-N-(2-methyl-4-nitrophenyl)benzenesulfonamide); iCRT3 (2-[[[2-(4-ethylphenyl)-5-methyl-4-oxazolyl]methyl]thio]-N-(2-phenylethyl)acetamide); iCRT5 (4-[(5Z)-5-[(3,4-dimethoxyphenyl) methylidene]-4-oxo-2-sulfanylidene-1,3-thiazolidin-3-yl]butanoic acid); and iCRT14 (iCRT-14 or (5Z)-5-[(2,5-dimethyl-1-pyridin-3-ylpyrrol-3-yl)methylidene]-3-phenyl-1,3-thiazolidine-2,4-dione), or a salt thereof.

14. The method of claim 13, wherein the tankyrase inhibitor is JW67 and the transcriptional activity inhibitor is iCRT14.

* * * * *